(12) United States Patent
Lee et al.

(10) Patent No.: US 11,208,685 B2
(45) Date of Patent: Dec. 28, 2021

(54) DIAGNOSTIC METHOD AND DEVICE PERFORMING THE SAME

(71) Applicant: NOUL CO., LTD., Gyeonggi-do (KR)

(72) Inventors: Dong Young Lee, Gyeonggi-do (KR); Chan Yang Lim, Gyeonggi-do (KR); Kyung Hwan Kim, Gyeonggi-do (KR); Young Min Shin, Gyeonggi-do (KR); Hyun Jeong Yang, Gyeonggi-do (KR)

(73) Assignee: NOUL CO., LTD., Yongin-si (KR)

( * ) Notice: Subject to any disclaimer, the term of this patent is extended or adjusted under 35 U.S.C. 154(b) by 743 days.

(21) Appl. No.: 16/079,485

(22) PCT Filed: Feb. 23, 2017

(86) PCT No.: PCT/KR2017/002032
§ 371 (c)(1),
(2) Date: Aug. 23, 2018

(87) PCT Pub. No.: WO2017/146508
PCT Pub. Date: Aug. 31, 2017

(65) Prior Publication Data
US 2019/0056298 A1  Feb. 21, 2019

Related U.S. Application Data

(60) Provisional application No. 62/298,959, filed on Feb. 23, 2016.

(30) Foreign Application Priority Data

Jun. 4, 2016 (KR) .......................... 10-2016-0069936
Jun. 4, 2016 (KR) .......................... 10-2016-0069937
(Continued)

(51) Int. Cl.
*G01N 1/00* (2006.01)
*C12Q 1/6844* (2018.01)
(Continued)

(52) U.S. Cl.
CPC .............. *C12Q 1/6844* (2013.01); *B01L 3/00* (2013.01); *C07K 16/3061* (2013.01);
(Continued)

(58) Field of Classification Search
None
See application file for complete search history.

(56) References Cited

U.S. PATENT DOCUMENTS 555,270 A   2/1896  Taylor
3,870,146 A  3/1975  Greenfield et al.
(Continued)

FOREIGN PATENT DOCUMENTS

CN   1034617 A   8/1989
CN   1207171 A   2/1999
(Continued)

OTHER PUBLICATIONS

Becton, Dickinson and Company, 2013, "BD™ EMB Agar (Eosin Methylene Blue Agar), Modified Intended Use," retreived from the internet: URL: https://legacy.bd.com/RESOURCE.ASPX?IDX=8973 [retreived on Apr. 2, 2020] (3 pages).
(Continued)

*Primary Examiner* — Jyoti Nagpaul
(74) *Attorney, Agent, or Firm* — Jones Day

(57) ABSTRACT

The present disclosure relates to a diagnostic method and a device performing the same. According to an aspect of the present disclosure, a diagnostic device is a diagnostic device that uses a test kit including a specimen plate having a specimen region in which a specimen is smeared and a patch plate configured to store a contact-type patch, which comes into contact with the specimen to stain the specimen, and the diagnostic device includes a body having a loading region in which the test kit is placed, a moving unit configured to move the patch plate and the specimen plate of the test kit
(Continued)

relative to each other so that the specimen placed in the test kit is smeared in the specimen region, and a contact unit configured to move a structure of the test kit such that the contact-type patch comes into contact with the smeared specimen so that the smeared specimen is stained.

20 Claims, 64 Drawing Sheets

(30) Foreign Application Priority Data

| | | | |
|---|---|---|---|
| Jun. 4, 2016 | (KR) | ........................ | 10-2016-0069938 |
| Jul. 27, 2016 | (KR) | ........................ | 10-2016-0095739 |
| Sep. 13, 2016 | (KR) | ........................ | 10-2016-0118462 |
| Nov. 1, 2016 | (KR) | ........................ | 10-2016-0144551 |

(51) Int. Cl.

| | |
|---|---|
| *G01N 1/30* | (2006.01) |
| *C12Q 1/6848* | (2018.01) |
| *G01N 33/50* | (2006.01) |
| *G01N 21/77* | (2006.01) |
| *G01N 33/558* | (2006.01) |
| *B01L 3/00* | (2006.01) |
| *G01N 15/06* | (2006.01) |
| *G01N 33/52* | (2006.01) |
| *G01N 33/574* | (2006.01) |
| *G01N 15/14* | (2006.01) |
| *G01N 33/49* | (2006.01) |
| *G01N 33/60* | (2006.01) |
| *C12Q 1/686* | (2018.01) |
| *C07K 16/30* | (2006.01) |
| *G01N 1/31* | (2006.01) |
| *C12Q 1/70* | (2006.01) |
| *G01N 33/483* | (2006.01) |
| *G06T 7/00* | (2017.01) |
| *G01N 33/53* | (2006.01) |
| *G01N 33/533* | (2006.01) |
| *B01L 7/00* | (2006.01) |
| *G01N 15/00* | (2006.01) |

(52) U.S. Cl.
CPC ............ *C12Q 1/686* (2013.01); *C12Q 1/6848* (2013.01); *C12Q 1/701* (2013.01); *G01N 1/30* (2013.01); *G01N 1/31* (2013.01); *G01N 1/312* (2013.01); *G01N 15/06* (2013.01); *G01N 15/14* (2013.01); *G01N 21/77* (2013.01); *G01N 33/4833* (2013.01); *G01N 33/49* (2013.01); *G01N 33/5082* (2013.01); *G01N 33/52* (2013.01); *G01N 33/533* (2013.01); *G01N 33/5304* (2013.01); *G01N 33/558* (2013.01); *G01N 33/574* (2013.01); *G01N 33/60* (2013.01); *G06T 7/0012* (2013.01); *G06T 7/0014* (2013.01); *B01L 3/505* (2013.01); *B01L 7/52* (2013.01); *G01N 2001/302* (2013.01); *G01N 2015/0065* (2013.01); *G01N 2015/0693* (2013.01); *G01N 2021/7723* (2013.01); *G01N 2021/7786* (2013.01)

(56) References Cited

U.S. PATENT DOCUMENTS

| | | | |
|---|---|---|---|
| 4,250,257 A | 2/1981 | Lee et al. | |
| 4,839,297 A | 6/1989 | Freitag et al. | |
| 4,938,593 A | 7/1990 | Morris et al. | |
| 5,143,714 A | 9/1992 | Cosgrove et al. | |
| 5,552,270 A | 9/1996 | Khrapko et al. | |
| 5,552,279 A | 9/1996 | Weisburg et al. | |
| 5,776,684 A | 7/1998 | Chirikjian et al. | |
| 5,779,982 A | 7/1998 | Aota et al. | |
| 5,928,879 A | 7/1999 | Dumler et al. | |
| 6,063,029 A | 5/2000 | Saita et al. | |
| 6,174,683 B1 | 1/2001 | Hahn et al. | |
| 7,261,800 B1 | 8/2007 | Nakazato | |
| 7,522,757 B2 | 4/2009 | Tsipouras et al. | |
| 7,767,414 B1 | 8/2010 | Smith et al. | |
| 8,293,487 B1 | 10/2012 | Zhang | |
| 8,305,579 B2 | 11/2012 | Treynor et al. | |
| 8,409,849 B2 | 4/2013 | Yamasaki | |
| 8,597,574 B2 | 12/2013 | Gumbrecht et al. | |
| 8,628,787 B2 | 1/2014 | Soldani et al. | |
| 8,809,027 B1 | 8/2014 | Lynch et al. | |
| 8,936,912 B2 | 1/2015 | Mitra et al. | |
| 10,234,447 B2 | 3/2019 | Manaresi et al. | |
| 10,254,286 B2 | 4/2019 | Pirie-Shepherd et al. | |
| 10,345,204 B2 | 7/2019 | Lee et al. | |
| 10,371,610 B2 | 8/2019 | Lee et al. | |
| 11,041,842 B2 | 6/2021 | Lee et al. | |
| 2002/0055126 A1 | 5/2002 | Schaffler et al. | |
| 2003/0083294 A1 | 5/2003 | Sullenger et al. | |
| 2003/0124619 A1 | 7/2003 | Weigl et al. | |
| 2003/0211507 A1 | 11/2003 | Hatch et al. | |
| 2004/0038306 A1 | 2/2004 | Agnew et al. | |
| 2004/0126826 A1 | 7/2004 | Yusuf et al. | |
| 2004/0175710 A1 | 9/2004 | Haushalter | |
| 2005/0139511 A1 | 6/2005 | Burns et al. | |
| 2005/0175987 A1 | 8/2005 | Jansen et al. | |
| 2005/0175997 A1 | 8/2005 | Ono et al. | |
| 2005/0202567 A1 | 9/2005 | Zanzucchi et al. | |
| 2005/0244976 A1 | 11/2005 | Gee et al. | |
| 2006/0088847 A1 | 4/2006 | Gu et al. | |
| 2006/0111331 A1 | 5/2006 | Eishingdrelo et al. | |
| 2006/0115905 A1 | 6/2006 | Hatch et al. | |
| 2006/0121474 A1 | 6/2006 | Kim et al. | |
| 2006/0172278 A1 | 8/2006 | Bonner et al. | |
| 2007/0051630 A1 | 3/2007 | Larsson et al. | |
| 2007/0087362 A1 | 4/2007 | Church et al. | |
| 2007/0117177 A1 | 5/2007 | Luo et al. | |
| 2007/0128073 A1 | 6/2007 | Tappen | |
| 2007/0224701 A1 | 9/2007 | Rosenstein | |
| 2008/0090267 A1 | 4/2008 | Komatsu et al. | |
| 2008/0138842 A1 | 6/2008 | Boehringer et al. | |
| 2008/0166745 A1 | 7/2008 | Khan et al. | |
| 2008/0182287 A1 | 7/2008 | Smith et al. | |
| 2008/0241890 A1 | 10/2008 | Gumbrecht et al. | |
| 2009/0098165 A1 | 4/2009 | Arulanandam et al. | |
| 2009/0220968 A1 | 9/2009 | Issadore et al. | |
| 2009/0226911 A1 | 9/2009 | Mauk et al. | |
| 2010/0047790 A1 | 2/2010 | Southern et al. | |
| 2010/0168390 A1 | 7/2010 | Brix et al. | |
| 2011/0041978 A1 | 2/2011 | Wallace et al. | |
| 2011/0070606 A1 | 3/2011 | Winkelman et al. | |
| 2011/0257666 A1 | 10/2011 | Ladet et al. | |
| 2012/0040397 A1 | 2/2012 | Luo et al. | |
| 2012/0064041 A1 | 3/2012 | Alexanian | |
| 2012/0171290 A1 | 7/2012 | Coursaget et al. | |
| 2013/0213811 A1 | 8/2013 | Kennedy et al. | |
| 2013/0288273 A1 | 10/2013 | Takagi et al. | |
| 2013/0296761 A1 | 11/2013 | Goto et al. | |
| 2013/0338016 A1 | 12/2013 | McDonough et al. | |
| 2014/0004527 A1 | 1/2014 | Oka et al. | |
| 2014/0038230 A1 | 2/2014 | Beck et al. | |
| 2014/0073063 A1 | 3/2014 | Lieber et al. | |
| 2014/0242607 A1 | 8/2014 | Sogabe et al. | |
| 2014/0273088 A1 | 9/2014 | Winther | |
| 2015/0080252 A1 | 3/2015 | Godwin et al. | |
| 2015/0139511 A1 | 5/2015 | Yoon et al. | |
| 2016/0265028 A1 | 9/2016 | Kim et al. | |
| 2019/0025281 A1 | 1/2019 | Lee et al. | |
| 2019/0048395 A1 | 2/2019 | Lee et al. | |
| 2019/0049349 A1 | 2/2019 | Lee et al. | |
| 2019/0049426 A1 | 2/2019 | Lee et al. | |
| 2019/0056296 A1 | 2/2019 | Lee et al. | |
| 2019/0064140 A1 | 2/2019 | Lee et al. | |
| 2019/0316995 A1 | 10/2019 | Lee et al. | |

(56) References Cited

U.S. PATENT DOCUMENTS

| | | |
|---|---|---|
| 2020/0011772 A1 | 1/2020 | Lee et al. |
| 2020/0240882 A1 | 7/2020 | Lee et al. |
| 2020/0249134 A1 | 8/2020 | Lee et al. |

FOREIGN PATENT DOCUMENTS

| | | |
|---|---|---|
| CN | 1363006 A | 8/2002 |
| CN | 1409110 A | 4/2003 |
| CN | 1561202 A | 1/2005 |
| CN | 1747703 A | 3/2006 |
| CN | 1971276 A | 5/2007 |
| CN | 101004377 A | 7/2007 |
| CN | 101225430 A | 7/2008 |
| CN | 101464237 A | 6/2009 |
| CN | 101598731 A | 12/2009 |
| CN | 101610847 A | 12/2009 |
| CN | 102245305 A | 11/2011 |
| CN | 102245755 A | 11/2011 |
| CN | 102272595 A | 12/2011 |
| CN | 102665917 A | 9/2012 |
| CN | 103038639 A | 4/2013 |
| CN | 103261872 A | 8/2013 |
| CN | 103328651 A | 9/2013 |
| CN | 103800040 A | 5/2014 |
| CN | 103808551 A | 5/2014 |
| CN | 104271191 A | 1/2015 |
| CN | 104349769 A | 2/2015 |
| CN | 104651473 A | 5/2015 |
| CN | 105122034 A | 12/2015 |
| CN | 105136795 A | 12/2015 |
| CN | 105259095 A | 1/2016 |
| EP | 2072993 A2 | 6/2009 |
| EP | 2206462 A1 | 4/2010 |
| EP | 2940474 A1 | 11/2015 |
| JP | S 63-281050 A | 11/1988 |
| JP | H 08-271390 A | 10/1996 |
| JP | S 52-89375 A | 7/1997 |
| JP | 2003344394 A | 12/2003 |
| JP | 2004077387 A | 3/2004 |
| JP | 2008518662 A | 6/2008 |
| JP | 2008164520 A | 7/2008 |
| JP | 2009518651 A | 5/2009 |
| JP | 2012515931 A | 7/2012 |
| JP | 5198399 B2 | 5/2013 |
| JP | 2013515235 A | 5/2013 |
| JP | 2013515955 A | 5/2013 |
| KR | 10-0601831 B1 | 7/2006 |
| KR | 10-2006-0112258 A | 10/2006 |
| KR | 10-2011-0084636 A | 7/2011 |
| KR | 10-2011-0136782 A | 12/2011 |
| KR | 10-2013-0138153 A | 12/2013 |
| KR | 10-2014-0082757 A | 7/2014 |
| KR | 10-2014-0100580 A | 8/2014 |
| KR | 10-2014-0103350 A | 8/2014 |
| KR | 10-1453796 B1 | 10/2014 |
| KR | 10-2015-0048964 A | 5/2015 |
| KR | 10-1540845 B1 | 7/2015 |
| WO | WO 2000077293 A1 | 12/2000 |
| WO | WO 2002072262 A1 | 3/2002 |
| WO | WO 2002072081 A1 | 9/2002 |
| WO | WO 2004024955 A1 | 3/2004 |
| WO | WO 2004071469 A2 | 8/2004 |
| WO | WO 2006050032 A2 | 5/2006 |
| WO | WO 2006050032 A3 | 5/2006 |
| WO | WO 2006053770 A1 | 5/2006 |
| WO | WO 2006108087 A2 | 10/2006 |
| WO | WO 2006108087 A3 | 10/2006 |
| WO | WO 2007067847 A2 | 6/2007 |
| WO | WO 2008075086 A1 | 6/2008 |
| WO | WO 201003 9627 A2 | 4/2010 |
| WO | WO 2010039627 A3 | 4/2010 |
| WO | WO 2010041088 A1 | 4/2010 |
| WO | WO 2010052543 A1 | 5/2010 |
| WO | WO 2010052543 A8 | 5/2010 |
| WO | WO 2010082820 A2 | 7/2010 |
| WO | WO 2010082820 A3 | 7/2010 |
| WO | WO 2011066449 A1 | 6/2011 |
| WO | WO 2011076705 A1 | 6/2011 |
| WO | WO 2011080539 A1 | 7/2011 |
| WO | WO 2011143075 A2 | 11/2011 |
| WO | WO 2011143075 A3 | 11/2011 |
| WO | WO 2012003579 A1 | 1/2012 |
| WO | WO 2012030313 A1 | 3/2012 |
| WO | WO 2012048154 A1 | 4/2012 |
| WO | WO 2012072980 A1 | 6/2012 |
| WO | WO 2012137506 A1 | 10/2012 |
| WO | WO 2013095896 A1 | 12/2012 |
| WO | WO 2013086015 A1 | 6/2013 |
| WO | WO 2013103712 A1 | 7/2013 |
| WO | WO 2013111054 A1 | 8/2013 |
| WO | WO 2013169924 A1 | 11/2013 |
| WO | WO 2014041093 A1 | 3/2014 |
| WO | WO 2014146062 A2 | 9/2014 |
| WO | WO 2014146062 A3 | 9/2014 |
| WO | WO 2015137595 A1 | 9/2015 |
| WO | WO 2017048871 A1 | 3/2017 |

OTHER PUBLICATIONS

Cardinal Health, 2013, "Histology vol. II: Laboratory products for your Histology needs," retrived from the Internet: URL:http://www.henryschein.com/assets/medical/2883001.pdf [retreived on Apr. 2, 2020] (95 pages).

Deiss et al., 2014, "Antimicrobial susceptibility assays in paper-based portable culture devices," Lab on a Chip, 14(1):167-171.

Dictionary.com, definition of "mesh," retrieved from internet: https://www.dictionary.com/browse/mesh?s=t on Feb. 3, 2020 (6 pages).

English translation of the International Search Report and Written Opinion of International Patent Application No. PCT/KR2017/002026 (published as WO 2017/146502) dated May 29, 2017 (7 pages).

English translation of the International Search Report and Written Opinion of International Patent Application No. PCT/KR2017/002027 (published as WO 2017/146503) dated May 29, 2017 (8 pages).

English translation of the International Search Report and Written Opinion of International Patent Application No. PCT/KR2017/002028 (published as WO 2017/146504) dated Jul. 6, 2017 (9 pages).

English translation of the International Search Report and Written Opinion of International Patent Application No. PCT/KR2017/002029 (published as WO 2017/146505) dated May 29, 2017 (9 pages).

English translation of the International Search Report and Written Opinion of International Patent Application No. PCT/KR2017/002030 (published as WO 2017/146506) dated May 29, 2017 (9 pages).

English translation of the International Search Report and Written Opinion of International Patent Application No. PCT/KR2017/002031 (published as WO 2017/146507) dated May 29, 2017 (12 pages).

English translation of the International Search Report and Written Opinion of International Patent Application No. PCT/KR2017/002032 (published as WO 2017/146508) dated May 29, 2017 (11 pages).

Geckil et al., 2010, "Engineering hydrogels as extracellular matrix mimics," Nanomedicine (Lond), 5(3):469-484.

Horibata et al., 2015, "Utilization of the Soft Agar Colony Formation Assay to Identify Inhibitors of Tumorigenicity in Breast Cancer Cells," J Vis Exp., (99):e52727 (7 pages).

Hudzicki, 2009, "Kirby-Bauer Disk Diffusion Susceptibility Test Protocol," American Society for Microbiology, retreived from the internet: https://www.asm.org/getattachment/2594ce26-bd44-47f6-8287-0657aa9185ad/kirby-bauer-disk-diffusion-susceptibility-test-protocol-pdf.pdf, retreived on Jul. 23, 2019 (23 pages).

Liu et al., 2009, "Aptamer-nanoparticle strip biosensor for sensitive detection of cancer cells," Anal Chem., 81(24):10013-10018.

(56) References Cited

OTHER PUBLICATIONS

Massart et al., 2009, "Striatal GPR88 expression is confined to the whole projection neuron population and is regulated by dopaminergic and glutamatergic afferents," Eur J Neurosci., 30(3):397-414.
Matsuo et al., 2001, "A simple method for classification of cell death by use of thin layer collagen gel for the detection of apoptosis and/or necrosis after cancer chemotherapy," Jpn J Cancer Res., 92(7):813-819.
Notodihardjo et al., 2015, "Gelatin hydrogel impregnated with platelet-rich plasma releasate promotes angiogenesis and wound healing in murine model," J Artif Organs., 18(1):64-71.
Oss-Ronen et al., 2011, "Polymer-conjugated albumin and fibrinogen composite hydrogels as cell scaffolds designed for affinity-based drug delivery," Acta Biomater, 7(1):163-170.
Punyani et al., 2006, "Sustained release of iodine from a polymeric hydrogel device for water disinfection," Journal of Applied Polymer Science, 103(5):3334-3340.
Rand, 1996, "Crystal violet can be used to visualize DNA bands during gel electrophoresis and to improve cloning efficiency," Technical Tips Online, 1:23-24.
Romano et al., 2015, "Controlled antiseptic/eosin release from chitosan-based hydrogel modified fibrous substrates," Carbohydr Polym., 131:306-314.
Wakayama et al., 2013, "Design of a single-step immunoassay principle based on the combination of an enzyme-labeled antibody release coating and a hydrogel copolymerized with a fluorescent enzyme substrate in a microfluidic capillary device," Lab Chip, 13(22):4304-4307.
Wu et al., 2008, "Disposable reagentless electrochemical immunosensor array based on a biopolymer/sol-gel membrane for simultaneous measurement of several tumor markers," Clin Chem., 54(9):1481-1488.
Zhu et al., 2015, "Microbiology Experiment and Learning Guide—Experiment 6 In Vitro Antibacterial Test of Drug," Fourth Force Medical University Press, pp. 24-26 (in Chinese with English translation), 11 pages.
Zustiak et al., 2010, "Solute diffusion and interactions in cross-linked poly (ethylene glycol) hydrogels studied by Fluorescence Correlation Spectroscopy," Soft Matter, 6(15):3609-3618.
Beck, M., et al., "On-chip sample preparation by controlled release of antibodies for simple CD4 counting", Lab Chip, 2012, 12, 167, 7 pages.
Man et al., 2011, "Currently Used Markers for CTC Isolation—Advantages, Limitations and Impact on Cancer Prognosis," J Clinic Experiment Pathol, 1:1 (7 pages).

(a)

(b)

(c)

(a)          (b)          (c)

(a)

(b)

(a)

(b)

(a)

(b)

(a)

(b)

DIAGNOSTIC METHOD AND DEVICE PERFORMING THE SAME

CROSS-REFERENCES TO RELATED APPLICATIONS

This application is a U.S. national phase application, pursuant to 35 U.S.C. § 371, of PCT/KR2017/002032, filed Feb. 23, 2017, designating the United States, which claims the benefit of U.S. Provisional Application No. 62/298,959, filed Feb. 23, 2016, and claims priority to Korean Application No. 10-2016-0069936, filed Jun. 4, 2016, to Korean Application No. 10-2016-0069937, filed Jun. 4, 2016, to Korean Application No. 10-2016-0069938, filed Jun. 4, 2016, to Korean Application No. 10-2016-0095739, filed Jul. 27, 2016, to Korean Application No. 10-2016-0118462, filed Sep. 13, 2016, and to Korean Application No. 10-2016-0144551, filed Nov. 1, 2016. The entire contents of the aforementioned patent applications are incorporated herein by this reference.

TECHNICAL FIELD

The present disclosure relates to a diagnostic method and a device performing the same, and more particularly, to a diagnostic method in which smearing and staining of a specimen are performed and the stained specimen is diagnosed and a diagnostic device performing the same.

BACKGROUND ART

A blood smear examination is a testing method in which blood is smeared and stained and morphologies of blood cells are observed using a microscope. A blood smear examination is mostly used in testing for infections of parasitic diseases such as malaria, blood cancers including leukemia, or congenital abnormalities in blood cell morphology.

A rapid diagnostic test (RDT) and a blood smear examination are mostly used in tests for parasitic diseases such as malaria. In the case of the RDT, there is an advantage wherein a convenient, prompt test is performed using a relatively low-cost diagnostic kit, but there is a problem wherein a test result is quite inaccurate. Consequently, nowadays, a blood smear examination is recommended for a more accurate test.

A blood smear examination is a method of testing for a disease by dropping a patient's blood on a slide, smearing and staining the blood, and observing the stained blood using a microscope. Since processes of smearing or staining blood and observing it with a microscope must be manually performed by an operator in a conventional blood smear examination, there is a problem in that it is difficult to smoothly carry out the test since a state of the smeared blood may not be uniform or blood may be erroneously stained due to an error of a reaction condition in a staining process when an operator is unskilled. Accordingly, it is difficult to actually apply a blood smear examination to a test for a disease in underdeveloped countries, such as some countries in Africa which lack medical personnel.

SUMMARY

An aspect of the present disclosure is to provide a diagnostic method in which a test kit is controlled by a device for a specimen to be conveniently and more accurately diagnosed and a diagnostic device performing the same.

Aspects of the present disclosure are not limited to those mentioned above, and unmentioned aspects will be clearly understood from the present specification and the accompanying drawings by those of ordinary skill in the art to which the present disclosure pertains.

According to an aspect of the present disclosure, there is provided a diagnostic device that uses a test kit including a specimen plate having a specimen region in which a specimen is smeared and a patch plate configured to store a contact-type patch, which comes into contact with the specimen to stain the specimen, the diagnostic device including a body having a loading region in which the test kit is placed, a moving unit configured to move the patch plate and the specimen plate of the test kit relative to each other so that the specimen placed in the test kit is smeared in the specimen region, and a contact unit configured to move a structure of the test kit such that the contact-type patch comes into contact with the smeared specimen so that the smeared specimen is stained.

According to another aspect of the present disclosure, there is provided a diagnostic device that uses a test kit including a specimen plate having a specimen region in which a specimen is smeared and a patch plate configured to store a contact-type staining patch, which comes into contact with the specimen to stain the specimen, the diagnostic device including a moving unit configured to move a structure of the test kit, wherein the moving unit transmits power to one or more of the specimen plate and the patch plate through a power transmission member, and moves the specimen plate and the patch plate relative to each other such that a smearing unit of the patch plate moves in one direction along a longitudinal direction of the test kit so that the specimen is smeared in the specimen region.

According to yet another aspect of the present disclosure, there is provided a diagnostic device that uses a test kit including a specimen plate having a specimen region in which a specimen is smeared and a patch plate configured to store a contact-type patch, which comes into contact with the specimen to stain the specimen, the diagnostic device including a moving unit configured to move the specimen plate and the patch plate relative to each other so that the specimen is smeared in the specimen region, and a contact unit configured to stain the smeared specimen, wherein the contact unit transmits power to a structure of the test kit through a power transmission member and moves one or more of the specimen plate and the patch plate such that the contact-type patch comes into contact with the specimen region in which the specimen is smeared.

According to still another aspect of the present disclosure, there is provided a diagnostic device that uses a test kit including a specimen plate having a specimen region in which a specimen is smeared and a patch plate configured to store a contact-type patch, which comes into contact with the specimen to stain the specimen, the diagnostic device including a body having a loading region in which the test kit is placed, a moving unit configured to transmit power to a first mounting portion on which the patch plate of the test kit is mounted or a second mounting portion on which the specimen plate is mounted such that the patch plate and the specimen plate move relative to each other so that the specimen placed in the test kit is smeared in the specimen region, and a contact unit configured to move a structure of the test kit such that the contact-type patch comes into contact with the smeared specimen so that the smeared specimen is stained.

According to still another aspect of the present disclosure, there is provided a diagnostic method that uses a test kit including a specimen plate having a specimen region in which a specimen is smeared and a patch plate configured to store a contact-type staining patch, which comes into contact with the specimen to stain the specimen, the diagnostic method including loading the test kit having the specimen placed therein, transmitting power to a structure of the test kit such that the patch plate and the specimen plate move relative to each other so that the specimen placed in the loaded test kit is smeared, and transmitting power to an upper surface of the patch plate of the test kit for the contact-type patch to move and come into contact with the smeared specimen so that the smeared specimen is stained.

Solutions of the present disclosure are not limited to those mentioned above, and unmentioned solutions should be clearly understood by those of ordinary skill in the art to which the present disclosure pertains from the present specification and the accompanying drawings.

According to the present disclosure, a test kit is controlled by a device such that a diagnostic method for diagnosing a sample (specimen) can become convenient and more accurate.

Advantageous effects of the present disclosure are not limited to those mentioned above, and unmentioned advantageous effects should be clearly understood by those of ordinary skill in the art to which the present disclosure pertains from the present specification and the accompanying drawings.

Figure 52:
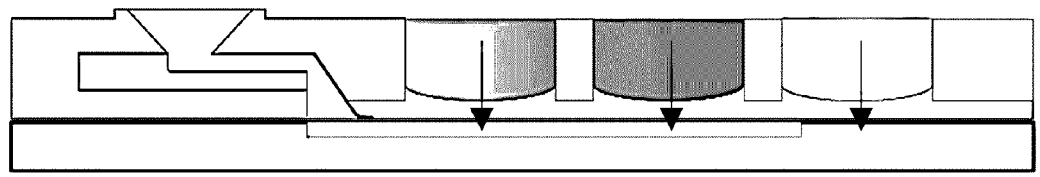
Figure 52:
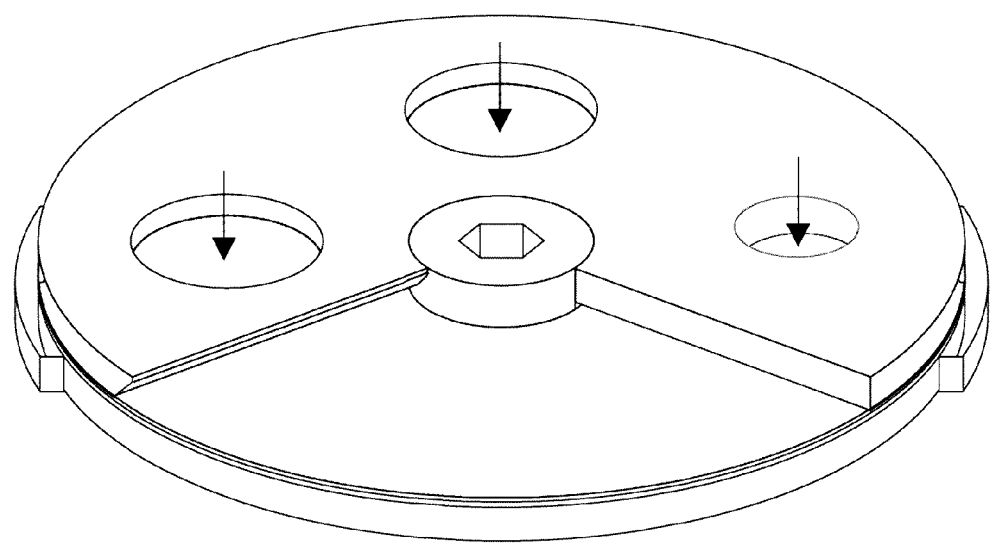

(a) and (b) of FIG. 52 are conceptual diagrams illustrating an example in which a structure of a test kit is moved by a contact operation of a contact unit according to an embodiment of the present disclosure.

Figure 53:
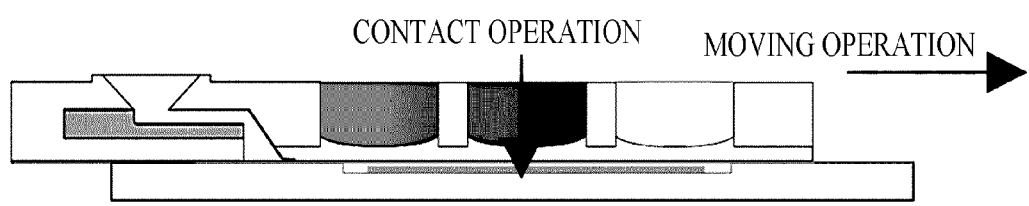

FIG. 53 is a conceptual diagram illustrating an example in which a staining operation of the present disclosure is performed according to an embodiment of the present disclosure.

Figure 54:
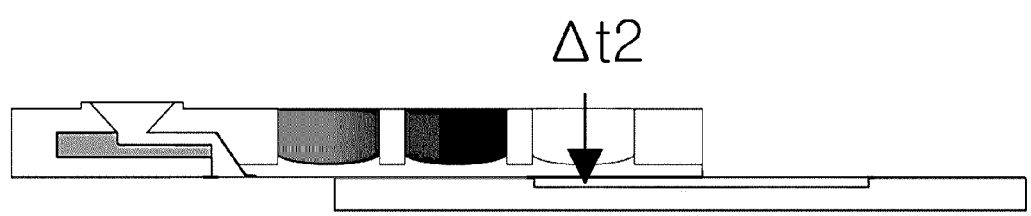
Figure 54:
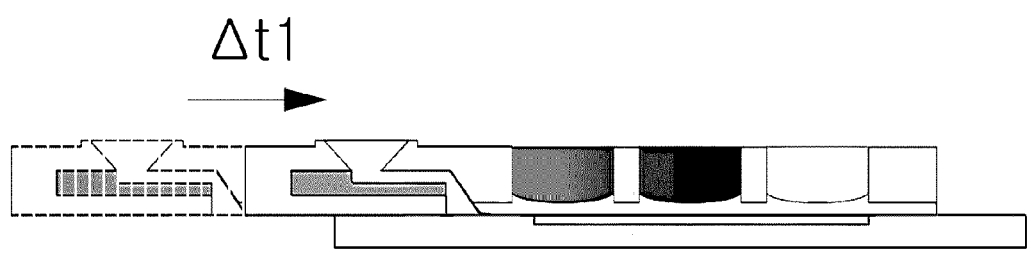

FIG. 54 is a view illustrating an example in which a controller controls operations of elements of a diagnostic system in the staining operation according to an embodiment of the present disclosure.

Figure 55:
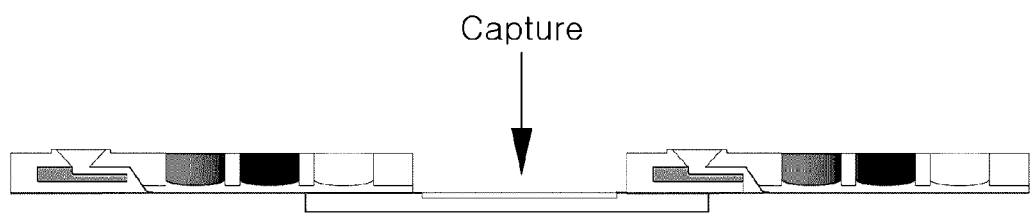

FIG. 55 is a view illustrating a process in which a structure of a test kit is moved so that an image is acquired according to an embodiment of the present disclosure.

Figure 56:
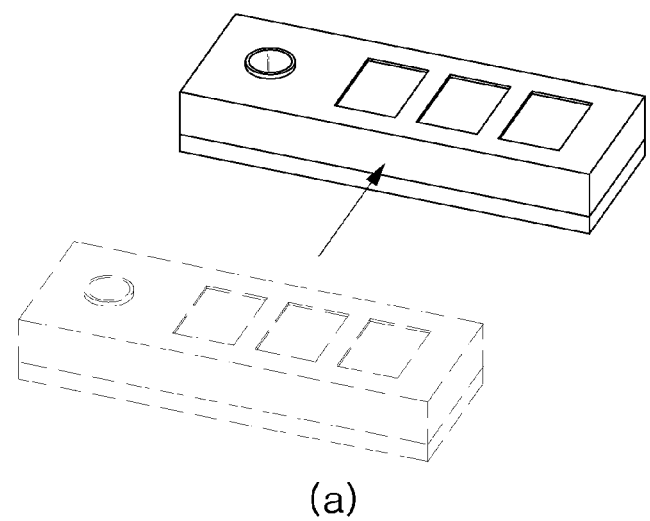
Figure 56:
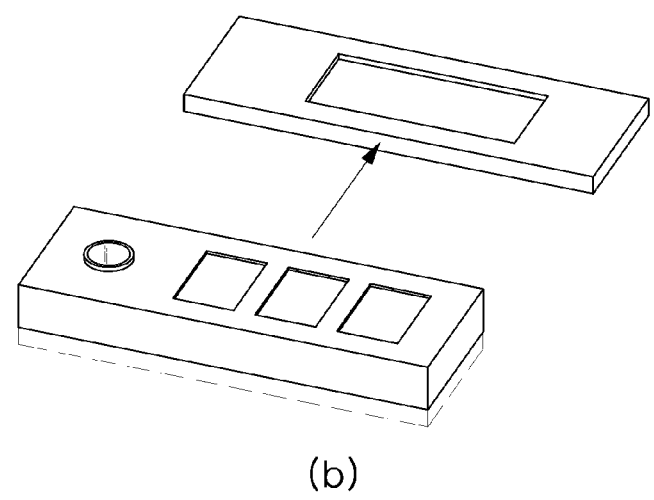

FIG. 56 is a view illustrating a process in which a test kit is moved to another space so that an image is acquired according to an embodiment of the present disclosure.

Figure 57:
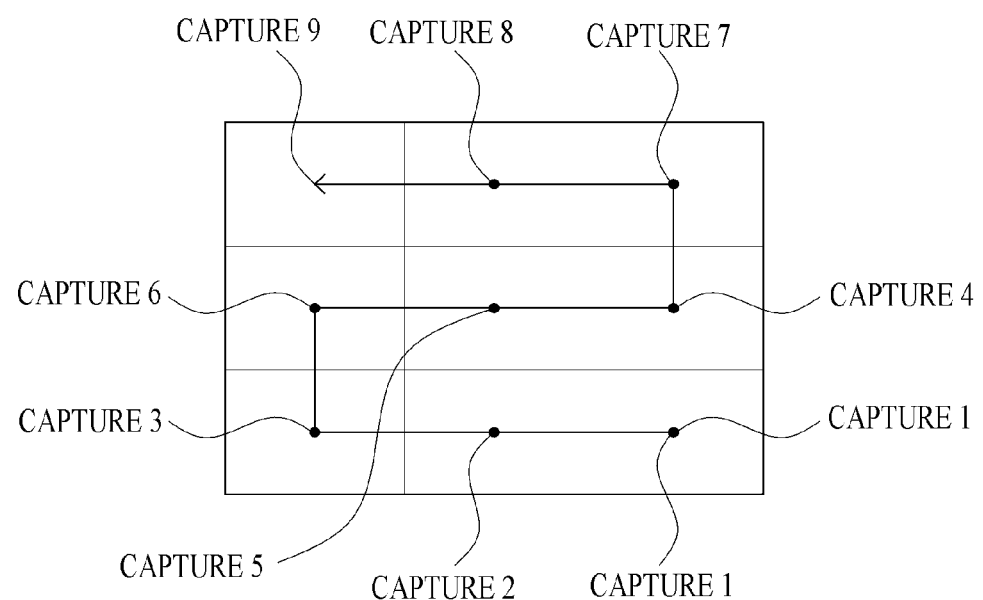

FIG. 57 is a view illustrating an example of acquiring an image according to an embodiment of the present disclosure.

Figure 58:
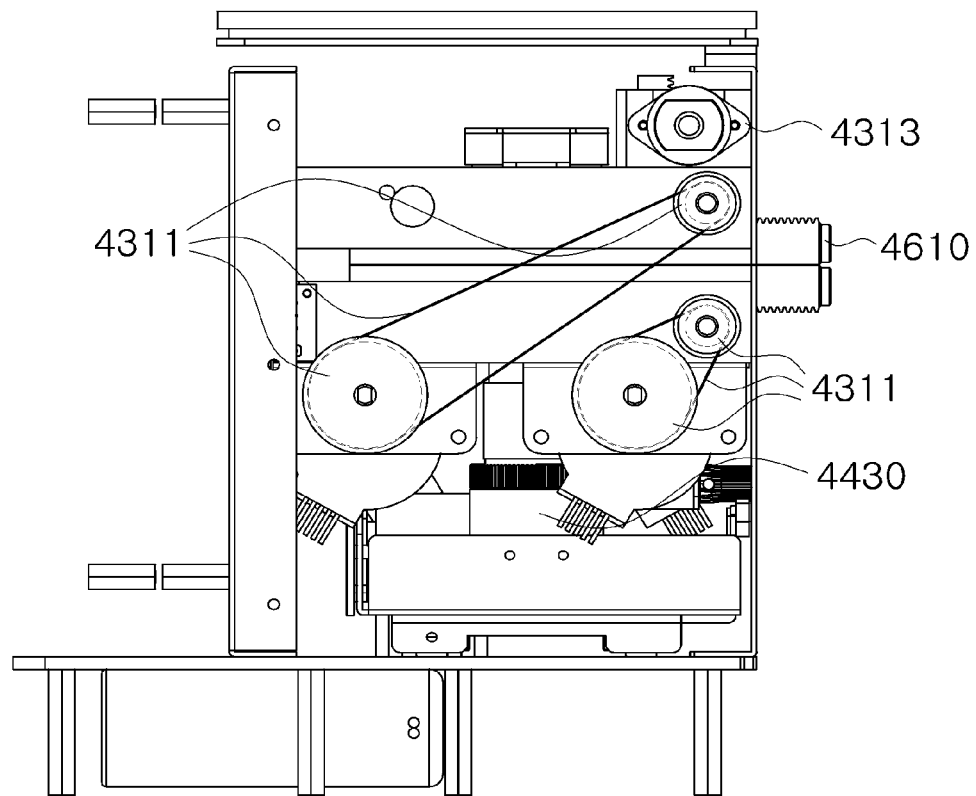

FIG. 58 is a view illustrating a side view of a diagnostic device implemented by the present disclosure according to an embodiment of the present disclosure.

Figure 59:
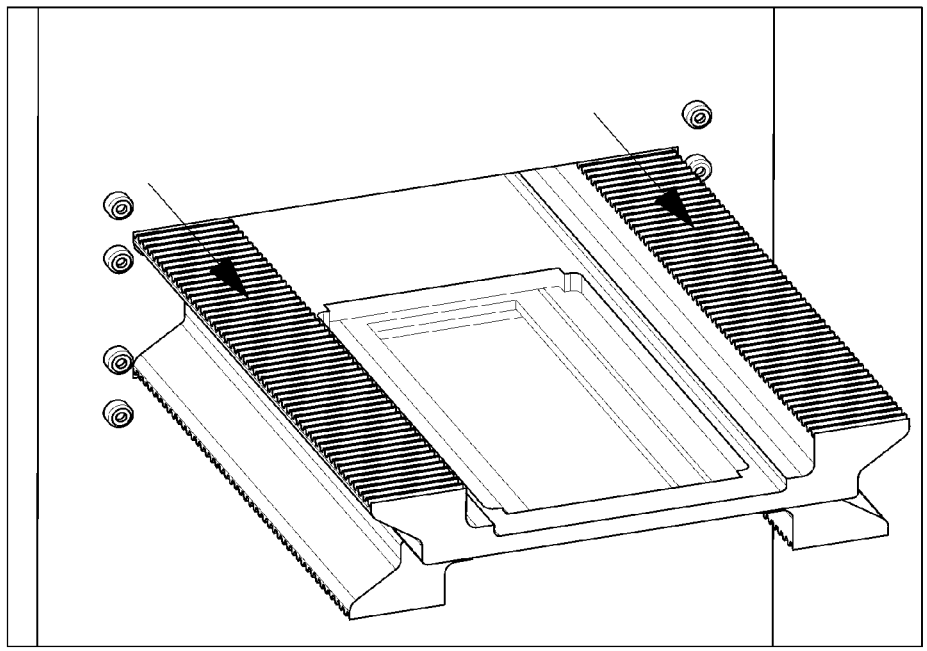

FIG. 59 illustrates a loading region of a diagnostic device implemented by the present disclosure according to an embodiment of the present disclosure.

Figure 60:
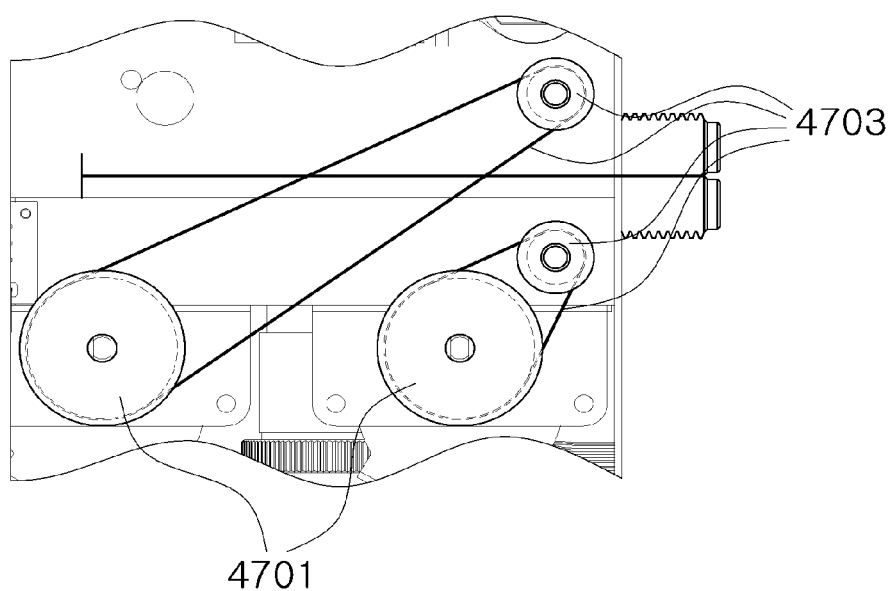

FIG. 60 is a view illustrating a moving unit implemented by the present disclosure according to an embodiment of the present disclosure.

Figure 61:
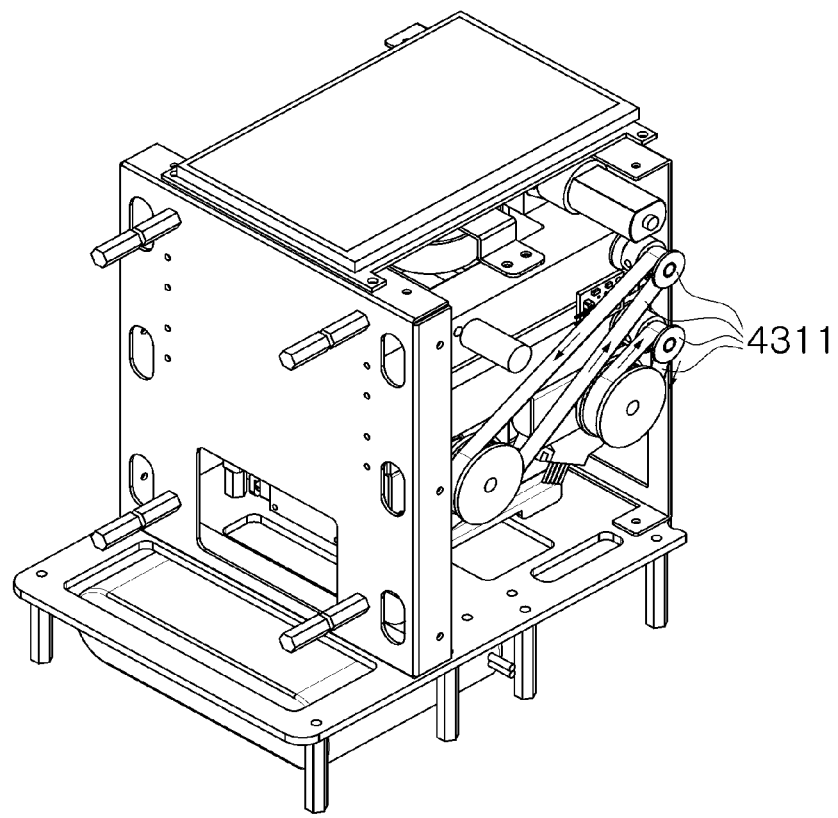

FIG. 61 is a view illustrating a moving operation that a moving unit implemented by the present disclosure performs according to an embodiment of the present disclosure.

Figure 62:
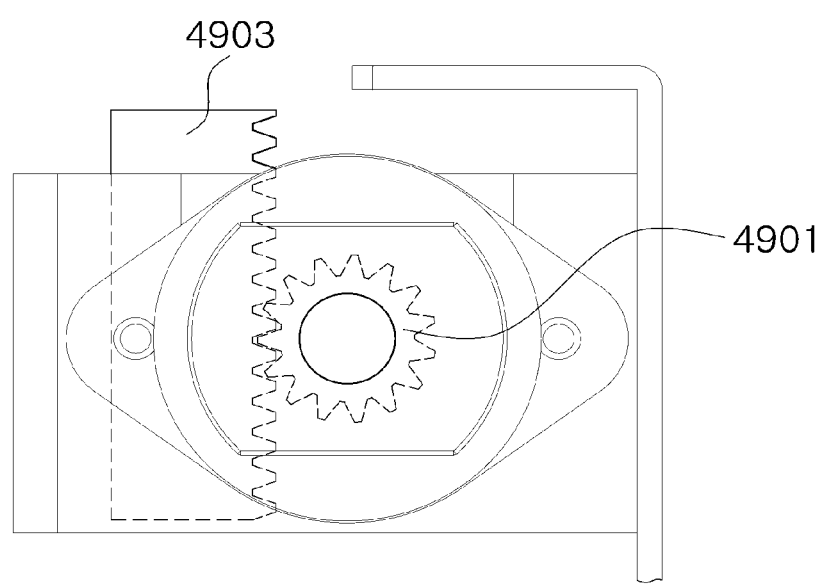

FIG. 62 is a view illustrating a contact unit implemented by the present disclosure according to an embodiment of the present disclosure.

Figure 63:
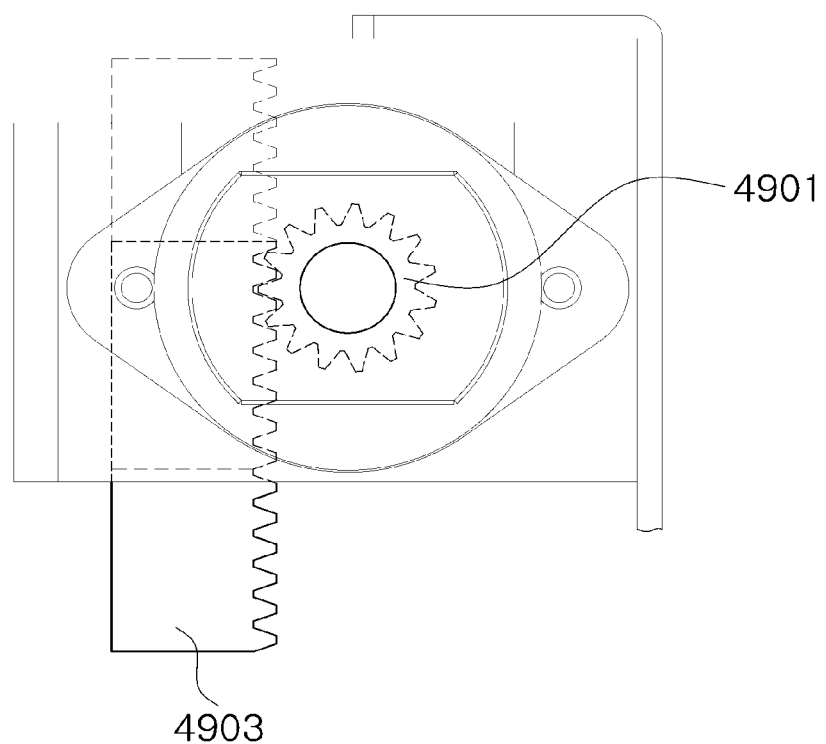

FIG. 63 is a view illustrating a contact operation that a contact unit of a diagnostic device performs according to an embodiment of the present disclosure.

Figure 64:
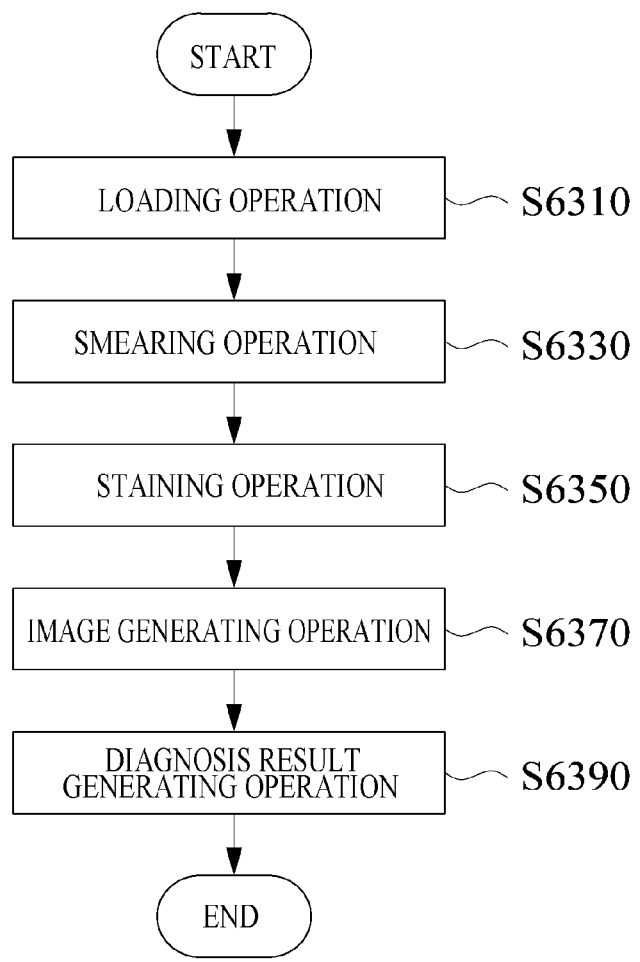

FIG. 64 is a flowchart illustrating a diagnostic method according to an embodiment of the present disclosure.

DETAILED DESCRIPTION

Since embodiments described herein are for clearly describing the spirit of the present disclosure to those of ordinary skill in the art to which the present disclosure pertains, the present disclosure is not limited to the embodiments described herein, and the scope of the present disclosure should be construed as including revised examples or modified examples not departing from the spirit of the present disclosure.

General terms currently being used as widely as possible have been selected as terms used herein in consideration of functions in the present disclosure, but the terms may be changed according to intentions and practices of those of ordinary skill in the art to which the present disclosure pertains or the advent of new technologies, etc. However, instead, when a particular term is defined as a certain meaning and used, the meaning of the term will be separately described. Consequently, the terms used herein should be construed on the basis of substantial meanings of the terms and content throughout the present specification instead of simply on the basis of names of the terms.

The accompanying drawings herein are for easily describing the present disclosure. Since shapes illustrated in the drawings may have been exaggeratedly depicted as much as necessary to assist in understating the present disclosure, the present disclosure is not to be limited by the drawings.

When detailed description of a known configuration or function related to the present disclosure is deemed to obscure the gist of the present disclosure in the present specification, the detailed description related thereto will be omitted as necessary.

According to an aspect of the present disclosure, there is provided a diagnostic device that uses a test kit including a specimen plate having a specimen region in which a specimen is smeared and a patch plate configured to store a contact-type patch, which comes into contact with the specimen to stain the specimen, the diagnostic device including a body having a loading region in which the test kit is placed, a moving unit configured to move the patch plate and the specimen plate of the test kit relative to each other so that the specimen placed in the test kit is smeared in the specimen region, and a contact unit configured to move a structure of the test kit such that the contact-type patch comes into contact with the smeared specimen so that the smeared specimen is stained.

The diagnostic device may further include an image acquisition module configured to acquire an image of the stained specimen.

The diagnostic device may further include a diagnostic module configured to diagnose a state of the specimen (sample) on the basis of the acquired image of the stained specimen.

The relative movement of the diagnostic device may have a form such that the patch plate is moved in one direction and the specimen plate is fixed or moved, and when the specimen plate is moved in the one direction, a movement speed of the patch plate may be higher than a movement speed of the specimen plate.

The loading region may be formed inside the body, and the diagnostic device may further include a loading region moving unit configured to move the loading region. The loading region moving unit moves the loading region to allow a user to place the test kit in the loading region.

The moving unit may include a power generator configured to generate power and a power transmission member configured to transmit power to the structure of the test kit.

The power generator and the power transmission member may be engaged with each other, and the moving unit may transmit the power to the specimen plate and the patch plate through the power transmission member.

The contact unit may include a power generator configured to generate power and a power transmission member configured to transmit the power to the structure of the test kit.

The power generator and the power transmission member may be engaged with each other, and the contact unit may transmit power to the contact-type patch stored in the patch plate through the power transmission member.

The moving unit may not allow the relative movement of the test kit when the contact-type patch is in contact with the specimen region and may allow the relative movement of the test kit when the contact-type patch is not in contact with the specimen region.

The image of the stained specimen may be generated after one or more of the test kit having the stained specimen placed therein and the structure of the test kit are moved.

The image of the stained specimen may be generated by combination of a plurality of frame images of the stained specimen.

According to another aspect of the present disclosure, there is provided a diagnostic device that uses a test kit including a specimen plate having a specimen region in which a specimen is smeared and a patch plate configured to store a contact-type staining patch, which comes into contact with the specimen to stain the specimen, the diagnostic device including a moving unit configured to move a structure of the test kit, wherein the moving unit transmits power to one or more of the specimen plate and the patch plate through a power transmission member, and moves the specimen plate and the patch plate relative to each other such that a smearing unit of the patch plate moves in one direction along a longitudinal direction of the test kit so that the specimen is smeared in the specimen region.

The patch plate may include the smearing unit, and the smearing unit may come into contact with the specimen and spread the specimen.

To smear the specimen in the specimen region, the moving unit may move the specimen plate and the patch plate relative to each other so that the smearing unit of the patch plate, which is in contact with the specimen, moves while sweeping the specimen region.

The moving unit may control a relative movement speed of the specimen plate and the patch plate. The control of the relative movement speed may include controlling speeds of one or more of the specimen plate and the patch plate.

The moving unit may stop relative movement of the specimen plate and the patch plate so that the smeared specimen is fixed, and may allow a fixing agent or a fixing patch, which is configured to fix the specimen, to come into contact with the smeared specimen or be prepared for contact therewith.

According to yet another aspect of the present disclosure, there is provided a diagnostic device that uses a test kit including a specimen plate having a specimen region in which a specimen is smeared and a patch plate configured to store a contact-type patch, which comes into contact with the specimen to stain the specimen, the diagnostic device including a moving unit configured to move the specimen plate and the patch plate relative to each other so that the specimen is smeared in the specimen region, and a contact unit configured to stain the smeared specimen, wherein the contact unit transmits power to a structure of the test kit through a power transmission member and moves one or more of the specimen plate and the patch plate such that the contact-type patch comes into contact with the specimen region in which the specimen is smeared.

The moving unit may move the specimen plate and the patch plate relative to each other so that the patch plate and the specimen plate are aligned. The moving unit may move the patch plate and the specimen plate relative to each other so that the contact-type patch of the patch plate is placed in the specimen region of the specimen plate.

When there are a plurality of contact-type patches, the contact unit may transmit the power to the structure of the test kit such that the plurality of contact-type patches each come into contact with the specimen region.

The contact unit may transmit power to the plurality of contact-type patches stored in the patch plate in the structure of the test kit.

The contact unit may transmit power to the structure of the test kit for a predetermined amount of time so that the contact-type patch comes into contact with the specimen region for the predetermined amount of time.

According to still another aspect of the present disclosure, there is provided a diagnostic device that uses a test kit including a specimen plate having a specimen region in which a specimen is smeared and a patch plate configured to store a contact-type patch, which comes into contact with the specimen to stain the specimen, the diagnostic device including a body having a loading region in which the test kit is placed, a moving unit configured to transmit power to a first mounting portion on which the patch plate of the test kit is mounted or a second mounting portion on which the specimen plate is mounted such that the patch plate and the specimen plate move relative to each other so that the specimen placed in the test kit is smeared in the specimen region, and a contact unit configured to move a structure of the test kit such that the contact-type patch comes into contact with the smeared specimen so that the smeared specimen is stained.

According to still another aspect of the present disclosure, there is provided a diagnostic method that uses a test kit including a specimen plate having a specimen region in which a specimen is smeared and a patch plate configured to store a contact-type staining patch, which comes into contact with the specimen to stain the specimen, the diagnostic method including loading the test kit having the specimen placed therein, transmitting power to a structure of the test kit such that the patch plate and the specimen plate move relative to each other so that the specimen placed in the loaded test kit is smeared, and transmitting power to an upper surface of the patch plate of the test kit such that the contact-type patch moves and comes into contact with the smeared specimen so that the smeared specimen is stained.

1. Contact-Type Staining Patch 1.1 Gel-Phase Contact-Type Staining Patch

Hereinafter, a contact-type staining patch 100 according to an embodiment of the present disclosure will be described.

The contact-type staining patch 100 according to the embodiment of the present disclosure may come into contact with a specimen T and stain the specimen T.

For example, the contact-type staining patch 100 may be used in various ways such as for 1) techniques in which an object to be stained is directly reacted with a staining reagent 140 including 1-1) a Giemsa staining technique or a Wright staining technique accompanied by a blood smear examination including a peripheral blood smear examination used in an examination for malaria and 1-2) a simple staining technique, a Gram staining technique, or an AFB [Ziehl-Neelsen] technique accompanied by a bacteriological examination 2) a Papanicolaou smear test mostly used for cervical cancer examination, 3) a fluorescence staining technique such as 4,6-diamidino-2-phenylindole (DAPI), 4) techniques in which an antigen-antibody reaction is used and an object to be detected using an antibody coupled to an isotope, a florescent substance, an enzyme, etc. may indirectly form color by radiation detection, fluorescent color formation, and enzymes including 4-1) an immunohistochemistry technique which is a specialized staining technique used in screening for cancer or 4-2) an enzyme linked immunosorbent assay (ELISA) technique used in a human immunodeficiency virus (HIV) test, 5) a fluorescence in situ hybridization (FISH) technique in which, to check a specific DNA sequence, a fluorescent substance is coupled to a DNA probe complementary to a target sequence to detect the target sequence, and 6) a precipitation technique or a cohesion technique using an antigen-antibody reaction.

In the present disclosure, "staining" in the contact-type staining patch 100 is not to be construed as limited to directly staining an object to be detected from the specimen T, but should be construed as a term that comprehensively encompasses all methods in which a specific target substance may be detected and checked for in the specimen T such as a method in which an object to be detected can form a fluorescent color, a method in which radiation can be detected, a method in which the object to be detected can react and form color when infused to a specific substrate by an enzyme, and a method in which cohesion or precipitation is induced so that the object to be detected can be detected.

In other words, in the present disclosure, the contact-type staining patch 100 serves to make a substance to be tested be in a state detectable in the specimen T, and thus, according to the actual technical spirit thereof, a contact-type "detection inducing" patch would be a clearer expression. However, for convenience of description and understanding of the present disclosure, the term, contact-type "staining" patch, will be used with a comprehensive meaning as necessary.

Consequently, similar to the preceding term, it should be reasonable that the term "stain" also be construed as having a wide meaning that encompasses all types of "detection inducing" that include inducing a fluorescent color formation, a color formation induction, radiation detection, precipitation, cohesion of an object to be detected, and inducing the object to be detected to be in other detectable states rather than being construed as having a narrow meaning of directly staining the object to be detected.

Along with the above, the specimen T refers to a substance that is an object to be tested, and it should be reasonable that the specimen T is construed as encompassing all biological samples that are subject to medical tests such as blood, cells, tissues, chromosomes, DNA, parasites, bacteria, etc.

Staining of the specimen T using the contact-type staining patch 100 may be performed as follows.

First, the contact-type staining patch 100 is provided in a gel phase, and the staining reagent 140 is stored in pores 122 therein. In this state, when the contact-type staining patch 100 is brought into contact with the specimen T, the staining reagent 140 in the pores 122 inside the contact-type staining patch 100 passes through a mesh structure of a gel matrix, moves to the specimen T, and stains a substance to be stained.

1.1.1. Basic Composition of a Contact-Type Staining Patch

Figure 1:
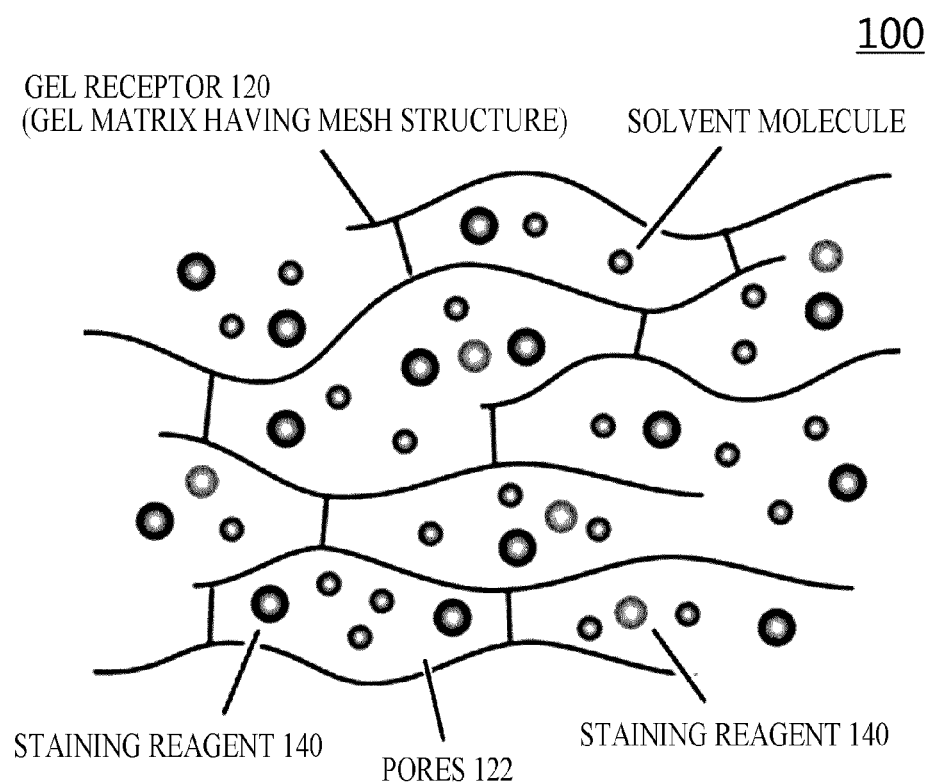
FIG. 1 is a cross-sectional view of a contact-type staining patch according to an embodiment of the present disclosure.

FIG. 1 is a cross-sectional view of the contact-type staining patch 100 according to an embodiment of the present disclosure.

Referring to FIG. 1, the contact-type staining patch 100 may include a gel receptor 120 and the staining reagent 140.

The gel receptor 120 is provided with a gel-phase substance having a porous mesh structure that forms the pores 122 therein. The pores 122 of the gel receptor 120 may accommodate the staining reagent 140.

The gel receptor 120 may be provided with various types of gel that form a gel matrix. For example, the gel receptor 120 may be gel formed of agarose. Here, agar may be used instead of agarose. When agar and agarose are compared to each other, the gel receptor 120 formed of agarose, which is a result of refining a polygalactose component in agar, has an advantage in terms of control of transparency or hardness, but a case in which agar is used may have an advantage in terms of cost when mass production is performed since a refining process and the like may be omitted.

Other than the above, a silicone gel, a silica gel, silicone rubber, polydimethylsiloxane (PDMS) gel known as a main component of a resin, a polymethylmethacrylate (PMMA) gel, and a gel using various other materials may be used as the gel receptor 120.

Hydrogel that can hold a staining reagent 140 which is usually in the form of an aqueous solution may be used as the gel receptor 120, but, unlike the above, a non-hydrogel substance for non-aqueous solution may also be used as necessary.

The staining reagent 140 is a substance that reacts with the specimen T to stain the specimen T. Here, the staining reagent 140 should be construed as having a comprehensive meaning that encompasses all substances, not only staining reagents, which directly stain the specimen T, but also an antibody, a DNA probe, or the like to which a staining substance, a fluorescent substance, or the like is coupled, that react with a substance to be stained to make the staining target detectable in examples of staining methods in which the above-described contact-type staining patch 100 can be used.

For example, the staining reagent 140 may include various types of staining solutions such as those used in Romanowsky staining techniques including acetocarmine, methylene blue, eosin, acid fuchsin, safranin, Janus Green B, hematoxylin, Giemsa solution, Wright solution, and Wright-Giemsa solution, Leishman staining solution, Gram staining solution, carbol-fuchsin, and Ziehl-Neelsen solution.

As another example, the staining reagent 140 may also include a DAPI fluorochrome, a DNA probe coupled to a fluorescent substance, and an antibody coupled to an enzyme, a fluorescent substance, an isotope, etc. Of course, the staining reagent 140 is not limited to the examples described above and may be any substance that reacts with a substance to be stained to make the substance to be stained detectable as mentioned above.

One staining reagent 140 or two or more staining reagents 140 may be mixed and stored in the pores 122.

For example, when attempting to perform a simple stain (a method of fixing bacteria and the like to a slide S and staining with one staining reagent 140) using the contact-type staining patch 100, the one staining reagent 140 may be stored in the pores 122. Here, methylene blue, crystal violet, safranin, etc. may be used as the staining reagent 140. Similar to this, when attempting to use the contact-type staining patch 100 to detect only a specific sequence, one staining reagent 140 in which a detection inducing substance such as a fluorescent substance is coupled to one type of DNA probe corresponding to the specific sequence may be used.

Unlike the example above, when attempting to perform a Giemsa stain using the contact-type staining patch 100, a composite reagent (sample) formed of a heterogeneous staining substance including eosin, which stains cytoplasm red, and methylene blue, which stains a nucleus violet, may be used as the staining reagent 140. That is, a first staining reagent 140-1 which is eosin and a second staining reagent 140-2 which is methylene blue may be mixed and stored in the pores 122.

Of course, a plurality of contact-type staining patches 100 each containing one staining reagent 140 may also be used instead of mixing and storing a plurality of staining reagents 140 in the pores 122 as described above in a staining technique in which a composite reagent is used as the staining reagent 140. For example, when attempting to perform a Giemsa stain, the staining reagents 140 may also be separately contained in separate contact-type staining patches 100 like an eosin patch (a first contact-type staining patch 100-1 that contains eosin as the first staining reagent 140-1) and a methylene blue patch (a second contact-type staining patch 100-2 that contains methylene blue as the second staining reagent 140-2).

1.1.2 Buffering Solution of a Contact-Type Staining Patch

As necessary, the staining reagent 140 may be accommodated in the pores 122 of the gel receptor 120 in a form that is dissolved in a solvent. Here, a buffering solution B that creates a reaction condition when a reaction occurs between the staining reagent 140 and a substance to be stained may be used as the solvent.

The buffering solution B serves to create a reaction environment in which a reaction between an object to be stained and the staining reagent 140 may easily occur during a staining reaction. For example, in a staining reaction such as a Giemsa stain, since basic methylene blue couples to a cell nucleus having a negative charge and stains the cell nucleus, and acidic eosin stains a cytoplasm, pH concentrations are closely related to a staining result. Thus, creating suitable pH concentrations may be extremely important for staining to be performed correctly. Consequently, in this case, the buffering solution B may be a pH buffering solution that maintains an optimal pH with respect to a reaction using the staining reagent 140 of the contact-type staining patch 100.

Although it will also be described below in description related to a buffering patch, a solution with a pH concentration equal to an optimal pH of a staining reaction may be used as the buffering solution B.

Alternatively, a solution with a pH concentration slightly different from the optimal pH of the staining reaction may be used as the buffering solution B. Unlike a conventional staining process in which a large amount of the buffering solution B is sprayed on the specimen T which is stained in a buffer step to set an optimal pH, the buffering solution B in the contact-type staining patch 100 is contained in the gel receptor 120, and the optimal pH of a staining reaction is set during a process in which the contact-type staining patch 100 and the specimen T come into contact with each other. Here, when the buffering solution B is contained in the gel receptor 120, the buffering solution B may react with the staining reagent 140 and the like and the pH of the buffering solution B may be slightly adjusted. To give a concrete example, in a case of the contact-type staining patch 100 that uses Giemsa dye as the staining reagent 140, a pH of the buffering solution B rises slightly after manufacturing the contact-type staining patch 100 in comparison to the pH of the buffering solution B before manufacturing the contact-type staining patch 100. This is due to a factor caused by interactions among the buffering solution B, the staining reagent 140, and the gel receptor 120 and a fact that an actual acting pH changes slightly when a buffering action is performed in a gel-contact type instead of in a conventional liquid spray type. Again, with respect to the contact-type staining patch 100 for a Giemsa stain, a pH of the buffering solution B contained in the contact-type staining patch 100 may be increased by approximately 0.1 to 0.4 in comparison to a pH of a raw material buffering solution B. When a desired optimal pH of a reaction is 6.8, a solution having a pH concentration of approximately 6.4 to 6.7 may be used as the buffering solution B. Setting an optimal pH of the contact-type staining patch 100 using a pH of the buffering solution B will be more clearly described in a buffering patch part below.

Specifically, when the contact-type staining patch 100 for a Giemsa stain manufactured using the buffering solution B, which has a pH of approximately 6.5, is brought into contact with the specimen T, which is stained, and the stained specimen T is observed, actual staining result was similarly observed to that resulting from spraying the buffering solution B, which has a pH of approximately 6.6 to 6.9, onto the specimen T.

In other words, an effective pH of the contact-type staining patch 100 manufactured using the buffering solution B, which has a specific pH value, may be changed to be slightly different from the pH value of the buffering solution B itself. Here, an effective pH refers to an acting pH during a reaction between the specimen T and a patch and may be, for example, a pH created in the specimen T when the buffering solution B, in a liquid phase, is sprayed onto the specimen.

Consequently, when manufacturing the contact-type staining patch 100, a pH of the buffering solution B may be adjusted so that the effective pH value of the contact-type staining patch 100 is substantially equal to an optimal pH value of a staining technique.

That is, a pH value of the buffering solution B itself, which will be used in a buffering patch, may be set as a value compensated for by a pH compensation value in consideration of a pH biased due to interactions among a gel, a staining reagent, and the buffering solution B in a gel matrix with respect to an optimal pH value that facilitates staining which may be defined in a conventional staining technique.

Here, the pH compensation value may be determined according to features of a gel, a type of a staining reagent, an amount of a staining reagent or a gel substance with respect to the buffering solution B, etc.

Here, with respect to features of a gel, a magnitude (i.e., an absolute value) of the pH compensation value may be increased or decreased according to a concentration, a hardness, porosity, density of a mesh structure, etc. of a gel of the gel receptor 120. For example, a magnitude of a pH compensation value may increase as a concentration of the gel of the gel receptor 120 increases, and a magnitude of the pH compensation value may decrease as the concentration of the gel lowers. In addition, for example, when an agarose gel is used as the gel receptor 120, a magnitude of the pH compensation value may increase as a concentration of agarose increases, and a magnitude of the pH compensation value may decrease as the concentration of agarose lowers. In addition, a magnitude of the pH compensation value may increase as the gel receptor 120 hardens, and a magnitude of the pH compensation value may decrease as the gel receptor 120 softens. In addition, a magnitude of the pH compensation value may decrease as porosity of the gel receptor 120 increases, and a magnitude of the pH compensation value may increase as the porosity decreases. In addition, a magnitude of the pH compensation value may increase as density of the mesh structure of the gel receptor 120 increases, and a magnitude of the pH compensation value may decrease as the density lowers.

In addition, with respect to interactions of a staining substance, a larger pH shift may occur as an amount of the staining substance with respect to the buffering solution B increases, and whether it is shifted toward being acidic or basic may be determined according to a type of the staining substance. In a case of a Giemsa stain substance, a pH shift of approximately 0.1-0.4 toward being basic may occur with respect to a phosphate buffer saline (PBS) buffer. The pH shift may be larger as an amount of a staining substance with respect to the buffering solution increases, and a pH shift toward the basic direction may occur when a type of the staining substance changes.

In the contact-type staining patch 100 according to an embodiment of the present disclosure described above, the gel receptor 120 performs a function of storing the staining reagent 140. Here, storing refers to 1) the gel receptor 120 preventing the staining reagent 140 contained therein from leaking to the outside; and 2) preventing the staining reagent 140 from being contaminated by the outside. The storage function is based on 1) a structural property of the gel matrix of the gel receptor 120; and 2) an electrochemical property of the gel receptor 120 and the staining reagent 140.

The storage function based on the structural feature of the gel receptor 120 may be accomplished as the staining reagent 140 accommodated in the pores 122 by the mesh structure of the gel receptor 120 is inhibited from moving to a surface of the gel receptor 120. This will be described in detail as follows.

The gel receptor 120 may form the pores 122 in the mesh structure that accommodates the staining reagent 140 inside the gel receptor 120. Here, the staining reagent 140 has to move to the surface of the gel receptor 120 from the pores 122 for the staining reagent 140 inside the pores 122 to exit to the outside. In this process, since the staining reagent 140 has to pass through the mesh structure, the staining reagent 140 accommodated inside the pores 122 may be prevented from leaking to the outside. In other words, the mesh structure of the gel receptor 120 inhibits the staining reagent 140 accommodated in the pores 122 from evaporating or leaking through the surface of the gel receptor 120. In addition, conversely, for the staining reagent 140 to be contaminated, a contaminant from the outside has to pass through the surface of the gel receptor 120 and move to the pores 122 inside the gel receptor 120. In this process, the mesh structure of the gel receptor 120 may inhibit foreign substances from being introduced into the gel receptor 120 and prevent the staining reagent 140 inside the gel receptor 120 from being contaminated.

In addition, the storage function based on the electrochemical property of the gel receptor 120 may be accomplished by electrochemical reactivity between the gel receptor 120 and the staining reagent 140. For example, when the staining reagent 140 stored in the pores 122 of the gel receptor 120 is in a form of an aqueous solution, a hydrophilic gel may be prepared as the gel receptor 120 to inhibit the staining reagent 140 from leaking to the outside from the gel receptor 120. In addition, according to the property of the gel receptor 120, since a substance with the opposite property cannot infiltrate into the gel receptor 120 from the outside (for example, a hydrophobic contaminant is inhibited from infiltrating into the hydrophilic gel receptor 120), the staining reagent 140 contained in the gel receptor 120 can be prevented from being contaminated.

In addition, the storage function of the gel receptor 120 is not limited to simply preventing leakage or contamination of the staining reagent 140. A reaction condition in staining is extremely important to smoothly stain blood in a blood smear examination. For example, when a suitable pH concentration is not achieved, a reaction between the staining reagent 140 and blood may not occur properly, erroneously stained blood may be observed with a microscope, and an error may occur in a test as a result.

With respect to the above, in the present disclosure, the staining reagent 140 may be accommodated in the pores 122 of the gel receptor 120 while having a proper reaction condition and the gel receptor 120 may store the staining reagent 140 while the reaction condition is maintained. For example, a Giemsa stain is performed under a pH of 7.2. For this, the staining reagent 140 for the Giemsa stain may be contained in the form of an aqueous solution having a pH of 7.2 in the pores 122 of the gel receptor 120. Since leakage to the outside or contamination due to an external substance of the staining reagent 140 or the aqueous solution is prevented by the mesh structure of the gel receptor 120, the staining reagent 140 for the Giemsa stain may be stored in the form of an aqueous solution pH of which is maintained at 7.2 inside the gel receptor 120.

The contact-type staining patch 100 has an advantage of being able to protect the staining reagent 140 for a long period of time while maintaining a desired reaction condition. This is a great advantage over a case in which a conventional staining technique is used in which a reaction condition of the staining reagent 140 needs to be set each time staining is conducted.

1.1.3 Additional Compositions of the Contact-Type Staining Patch

The contact-type staining patch 100 may further include various additional compositions. Similar to the staining reagent 140, the additional compositions may be accommodated in the pores 122 of the gel receptor 120 to be contained in the contact-type staining patch 100.

For example, an evaporation preventing agent may be included in the contact-type staining patch 100. The evaporation preventing agent may perform a role of preventing the staining reagent 140 inside the gel receptor 120 from leaking to the outside by evaporation. Although, as described above, the staining reagent 140 stored in the pores 122 of the gel receptor 120 in a form of an aqueous solution and the like is inhibited to some extent from leaking to the outside by a water-soluble property of the gel matrix structure or the gel receptor 120, the staining reagent 140 may be stored for a long period while performance of the contact-type staining patch 100 is maintained by the evaporation preventing agent contained in the gel receptor 120. The evaporation preventing agent may have a weight ratio of 5% or less and may preferably have a weight ratio of 1% or less.

In another example, a degeneration preventing agent may be included in the contact-type staining patch 100. Like an antiseptic and an antibiotic that prevents proliferation of bacteria in the contact-type staining patch 100, the degeneration preventing agent performs a function of preventing the staining reagent 140 inside the contact-type staining patch 100 from degenerating due to various causes. When the gel receptor 120 is exposed, bacteria or germs may proliferate therein, and performance of the contact-type staining patch 100 may be degraded as a result due to contamination of the staining reagent 140. When the degeneration preventing agent is added to the contact-type staining patch 100, a shelf life of the contact-type staining patch 100 may be extended.

1.2. Staining Process Using the Contact-Type Staining Patch

Figure 2:
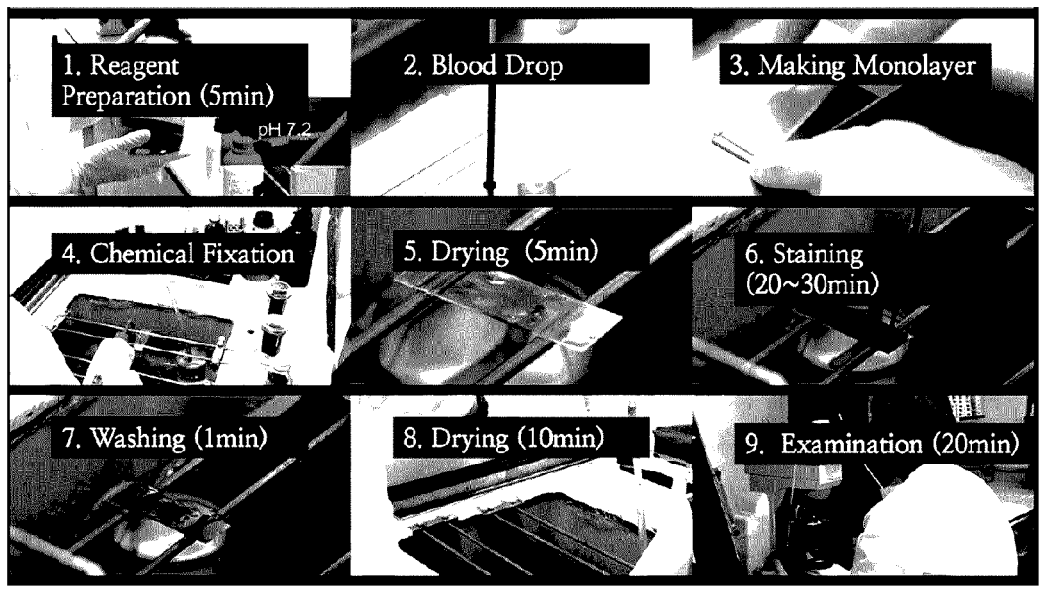
FIG. 2 is a view illustrating a conventional blood smear examination process.
Figure 3:
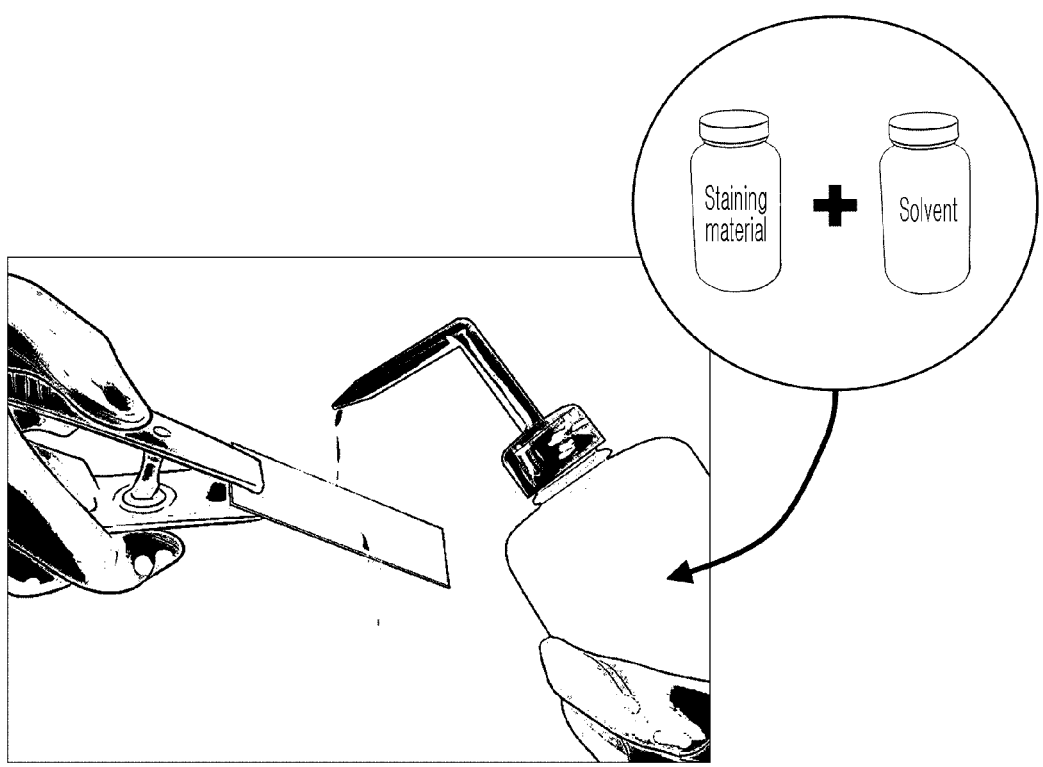
FIG. 3 is a view about a process of preparing a staining solution and a staining process of the conventional blood smear examination process.

FIG. 2 is a view illustrating a conventional blood smear examination process, and FIG. 3 is a view related to a staining process of the conventional blood smear examination process.

Referring to FIG. 2, the conventional blood smear examination is conducted as follows. First, a reactant, such as a staining solution, is prepared. Next, blood is dropped onto the slide S, and the blood is smeared. When the blood is smeared on the slide S, the blood is fixed and dried. The fixing of the smeared blood may be performed primarily using a chemical fixing means. When the smeared blood is fixed to the slide S, a staining solution is poured on it to stain the blood. Here, since the staining solution is poured onto the blood and thus a large amount of the staining solution is mixed with the blood, the mixture of the staining solution and the blood is washed and then dried again. Following this process, the stained blood on the slide S may be observed using a microscope and the like to conduct the blood smear examination.

Referring to FIG. 3, staining is performed in a form of spraying a staining solution onto the slide S on which blood is smeared in the conventional blood smear examination, and, for this, a staining solution has to be manufactured on the spot using a powdered staining reagent 140. Consequently, manual work of a skilled person or separate equipment for mixing a proper ratio is required to set a ratio between the staining reagent 140 and a solvent. Furthermore, when a staining solution is manufactured in advance, 1) the staining solution manufactured in advance may contact with air and react; 2) a reaction between the solvent and the staining reagent 140 may occur inside the staining solution; or 3) a reaction between heterogeneous staining reagents 140 may occur when the staining solution is manufactured and used by mixing a plurality of staining reagents 140. Accordingly, since the staining solution may be contaminated or a proper reaction condition may not be maintained, the staining solution can only be used for a few hours after manufacture.

With respect to this, since the contact-type staining patch 100 according to an embodiment of the present disclosure stores the staining reagent 140 in the pores 122 therein that forms the mesh structure in the gel receptor 120 thereof while a desired reaction condition is maintained, the contact-type staining patch 100 can be manufactured in advance instead of manufacturing a staining solution at an examination site by mixing the staining reagent 140 with a solvent, and the contact-type staining patch 100 can be used in examinations for a long period of time.

Figure 4:
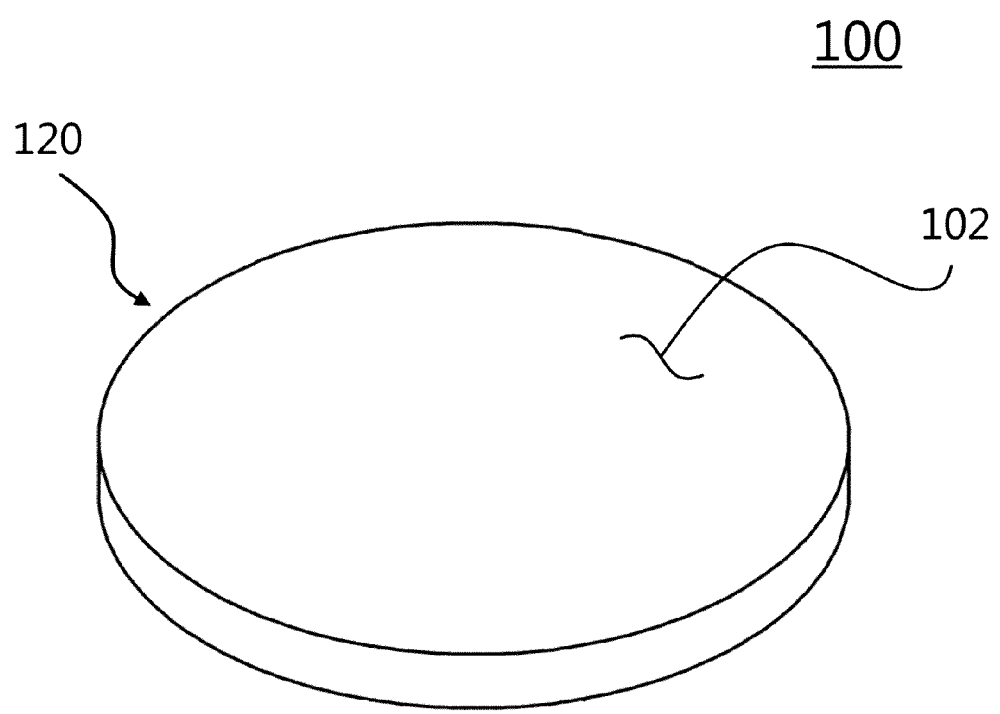
FIG. 4 is a perspective view of the contact-type staining patch according to an embodiment of the present disclosure.
Figure 5:
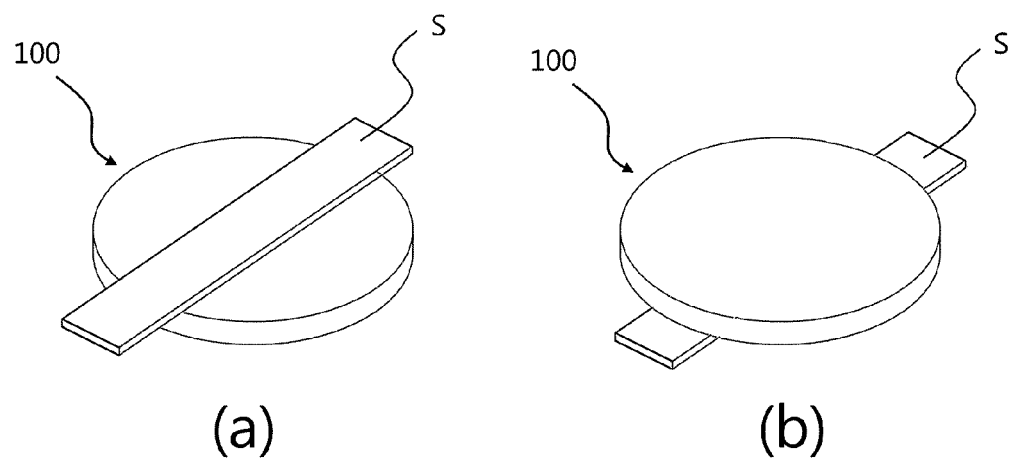
FIG. 5 is a view illustrating a contact state between the contact-type staining patch and a specimen slide according to an embodiment of the present disclosure.

FIG. 4 is a perspective view of the contact-type staining patch 100 according to an embodiment of the present disclosure, and FIG. 5 is a view illustrating a contact state between the contact-type staining patch 100 and a specimen slide according to an embodiment of the present disclosure.

Referring to FIG. 4, a shape of the contact-type staining patch 100 may be defined by a shape of the gel receptor 120 and may have a contact surface 102 for coming into contact with the specimen T formed on at least one surface thereof. Here, the contact surface 102 is a surface that directly comes into contact with the specimen T and may preferably be a flat surface to facilitate contact with the specimen T smeared on the slide S. For example, the contact-type staining patch 100 may be provided in the form of a column as illustrated in FIG. 4, and in such a cylindrical column form, one of an upper surface and a lower surface of the column may be the contact surface 102.

With reference to FIG. 5, it may be seen that the contact-type staining patch 100 is brought into contact with the specimen T by mounting the slide S on which the specimen T is smeared on the upper surface of the contact-type staining patch 100 illustrated in FIG. 4 or, conversely, by mounting the staining patch on the slide S on which the specimen T is smeared.

The shape of the contact-type staining patch 100 is not limited to the shape illustrated in FIG. 4 and may also include a plurality of contact surfaces 102. For example, the contact-type staining patch 100 may be manufactured in a hexahedral shape, and one or a plurality of surfaces thereof may be used as the contact surfaces 102. In another example, the contact-type staining patch 100 may also be manufactured in a hemispherical shape in which a bottom surface thereof is the contact surface 102.

Figure 6:
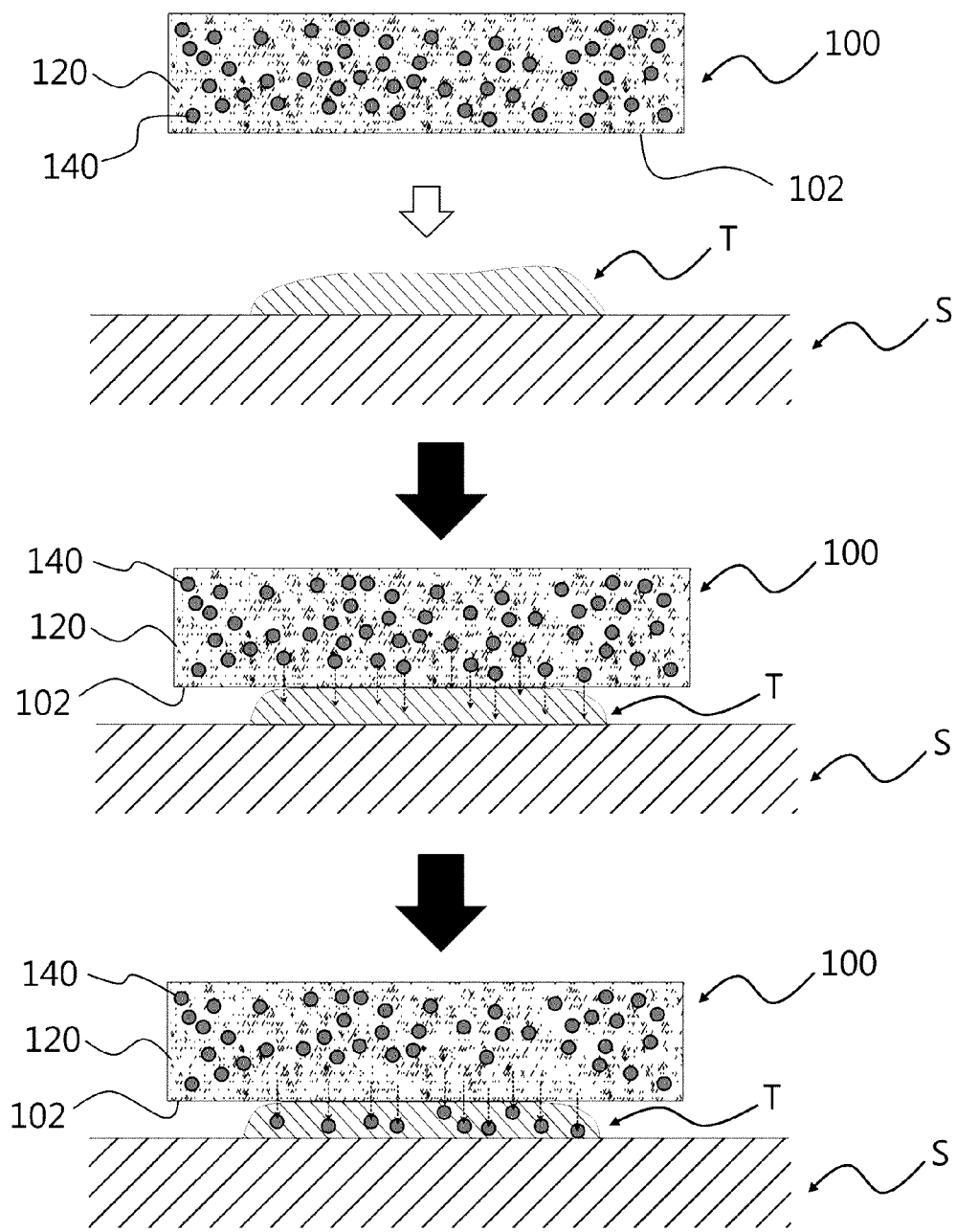
FIG. 6 is a view related to a staining process using the contact-type staining patch according to an embodiment of the present disclosure.

FIG. 6 is a view related to a staining process using the contact-type staining patch 100 according to an embodiment of the present disclosure.

Referring to FIG. 6, the contact-type staining patch 100 may come into contact with the specimen T smeared on the slide S. In other words, the contact surface 102 of the gel receptor 120 may directly come into contact with the specimen T. When the contact occurs, the staining reagent 140 may pass through the mesh structure and move to the specimen T through the contact surface by an electrochemical action between the specimen T or a specific component in the specimen T that reacts with the staining reagent 140 and the staining reagent 140 contained inside the gel receptor 120, i.e., accommodated in the pores 122 therein. The staining reagent 140 that has moved to the specimen T may react with the specimen T or the specific component in the specimen T and stain the specimen T.

Here, since the staining reagent 140 is stored inside the gel receptor 120 while the reaction condition is maintained, staining can be smoothly performed even though the reaction condition is not separately adjusted.

Although the staining reagent 140 passes through the mesh structure of the gel receptor 120 and moves to the specimen T by a force acting between the staining reagent 140 and the specimen T or the specific component in the specimen T, since the movement is performed while being somewhat limited by the mesh structure, an excessively large amount of the staining reagent 140 or the staining solution may be prevented from moving to the specimen T.

Here, the amount of the staining reagent 140 or the staining solution moving to the specimen T may be controlled by adjusting a density of the mesh structure and a degree of liquidity, porosity, etc. of gel. That is, by properly adjusting a hardness of the gel, only a proper amount of the staining reagent 140 may be transferred to the specimen T from the contact-type staining patch 100.

For example, when the contact-type staining patch 100 for a Giemsa stain is manufactured using an agarose gel for a peripheral blood smear examination, the concentration of agarose may preferably be 1 to 5%. When the concentration of agarose is higher than the range above, the movement of the staining reagent 140 may be delayed and a sufficient amount of the staining reagent 140 may not move to the blood, and thus a problem in which staining is not performed may occur. Conversely, when the concentration of agarose is lower than the range above, an excessive movement of the staining reagent 140 may occur and a superfluous amount of the staining reagent 140 may be transferred to the blood. Although staining can be smoothly performed when a superfluous amount of the staining reagent 140 is transferred, there may be disadvantages in which the staining reagent 140 is wasted and a residue remains on the blood such that washing and drying processes for removing the residue are required afterwards. Consequently, the concentration of agarose may preferably be 1.5 to 2.5%.

Referring again to FIG. 5, when the contact-type staining patch 100 is brought into contact with the specimen T, the contact-type staining patch 100 may either simply come into contact with the specimen T without any external pressure (only gravity acts during a simple vertical contact, but this may be deemed as having almost no pressure) or a predetermined pressure may be applied therebetween. This may be properly selected according to a hardness of the contact-type staining patch 100. For example, a sufficient amount of the staining reagent 140 may be transferred to the specimen T with only a simple contact when the contact-type staining patch 100 is manufactured to be somewhat soft, and conversely, a predetermined pressure may need to be applied for a proper amount of the staining reagent 140 to be transferred to the specimen T when the contact-type staining patch 100 is manufactured to be somewhat hard.

When the contact-type staining patch 100 that directly comes into contact with the specimen T to stain the specimen T is used, there is an advantage in which 1) staining can be performed under a correct reaction condition by only bringing the contact-type staining patch 100 into contact with the specimen T even though the reaction condition is not separately adjusted; 2) a waste of the staining reagent 140 can be minimized; and 3) a staining process is simplified due to the omission of a preprocessing process such as fixing the specimen T before staining or a postprocessing process such as washing and drying after staining.

Referring again to FIGS. 2 and 3, the staining solution has to be manufactured on the spot for staining in the conventional blood smear examination, and there is a problem of an error in staining being likely due to a failure of setting a proper reaction condition due to an operator's mistake. Alternatively, even when separate equipment that properly mixes the staining reagent 140 with a solvent is used to address the problem above, not only is an additional cost required for buying the mixing equipment, but an inconvenience of having to perform the mixing work each time the staining work is performed is also required such that there is a loss in terms of time and cost.

In contrast, the contact-type staining patch 100 according to an embodiment of the present disclosure stores the staining reagent 140 maintained at a proper reaction condition therein and staining is correctly performed by only bringing the contact-type staining patch 100 into contact with the specimen T such that it is far more convenient and anyone, even someone who is not skilled medical personnel, can perform staining.

In addition, referring to FIGS. 2 and 3, staining is performed in the form of spraying a staining solution onto the slide S on which blood is smeared in the conventional blood smear examination, and there is a problem in which a large amount of the staining reagent 140 is wasted in the above case. Not only is there great loss in terms of cost due to a difficulty of reusing the staining reagent 140 that was sprayed once, but there is also a concern of negatively affecting the environment when the staining reagent 140 is left as it is such that a burden of managing the staining reagent 140 is also added.

In contrast, the contact-type staining patch 100 according to an embodiment of the present disclosure transfers only a required amount of the staining reagent 140 to blood by coming into contact with the specimen T while the staining reagent 140 or a staining solution is stored therein such that the staining reagent 140 can be saved, and recovery of the staining reagent 140 after use is far more convenient since the staining reagent 140 in a gel phase is brought into contact therewith instead of the staining reagent 140 in a fluid form being sprayed thereto.

Furthermore, since the contact-type staining patch 100 can be stored for a long period of time, the contact-type staining patch 100 may not be discarded after being used once and may also be used several times. Therefore, advantages in terms of cost and environmental protection become even clearer when the contact-type staining patch 100 is used several times.

In addition, referring to FIGS. 2 and 3, since staining is performed in the form of spraying a staining solution onto blood in the conventional blood smear examination, a preprocessing process of fixing blood on the slide S is required to prevent the blood from being swept away by the staining solution.

In contrast, the contact-type staining patch 100 according to the embodiment of the present disclosure transfers the staining reagent 140 to blood through a simple contact such that, even when the specimen T remains on the slide S or some blood is swept away toward the contact-type staining patch 100 from the slide S in this process, only small amounts thereof are involved, and thus, as necessary, the specimen T may not have to be fixed on the slide S. Of course, there may be cases in which fixating the specimen T is required to further optimize a test result. However, the benefit of fixating the specimen T is similar to the benefit generated due to the simplification of a test process such that the operator may select whether to fixate the specimen T with due consideration for the benefits.

In addition, referring to FIGS. 2 and 3, after the blood is stained, a sprayed staining solution remaining on the slide S has to be removed and thus post-processing such as washing and drying is required in the conventional blood smear examination.

In contrast, in the contact-type staining patch 100 according to an embodiment of the present disclosure, the staining reagent 140 or the staining solution is not excessively transferred to the slide S and thus residue is prevented from remaining on the slide S such that a washing process may be omitted, and due to the omission of the washing process, a drying process may also be omitted.

Particularly, there is a problem in which an erroneous staining result is brought about due to the washing process in the conventional blood smear examination, e.g., an occurrence of decolorization when washing is performed for a long time. When the contact-type staining patch 100 according to an embodiment of the present disclosure is used, the washing process itself is unnecessary, and the erroneous staining itself due to the washing process can be prevented.

1.3. Method of Manufacturing a Contact-Type Staining Patch

Hereinafter, a method of manufacturing the above-described contact-type staining patch 100 according to an embodiment of the present disclosure will be described.

An example of a method of manufacturing the contact-type staining patch 100 may include forming the gel receptor 120 and absorbing the staining reagent 140 into the gel receptor 120.

First, the gel receptor 120 is formed using a gel raw material that serves as a gel formation substance, a gelable substance, etc. such as agarose powder and the like. For example, the gel receptor 120 may be manufactured when agarose powder and water are mixed at a proper ratio, and the mixture is heated and cooled. Here, boiling the mixture, baking the mixture using a microwave, or the like may be used as the heating method. In addition, here, the cooling method may include natural cooling or forced cooling, and a stirring process may be included in the cooling method as necessary.

Next, the staining reagent 140 may be absorbed into the manufactured gel receptor 120. To absorb the staining reagent into the gel receptor 120, a method in which the gel receptor 120 is dipped in a chamber, a container, or the like in which the staining reagent 140 is accommodated for a predetermined amount of time and the gel receptor 120 is then taken out after the staining reagent 140 is sufficiently absorbed thereinto may be used.

In another example, the method of manufacturing the contact-type staining patch 100 may include a method in which a gel raw material, an aqueous solution, and a staining reagent are mixed to form a gel receptor. For example, the contact-type staining patch 100 may be manufactured by mixing agarose, an aqueous solution (or a buffering solution), and the staining reagent 140 (which may be mixed with the buffering solution) at a proper ratio, and heating and cooling the mixture. Here, a heating and cooling means may be similar to the examples described above.

In yet another example, the method of manufacturing the contact-type staining patch 100 may include a method in which a gel raw material and a solution are mixed and heated and the staining reagent 140 is then injected during a process of cooling the heated mixture. For example, after agarose and an aqueous solution are mixed at a proper ratio and heated, the staining reagent 140 may be added to the mixture, during a process of cooling the heated mixture.

1.4 Experimental Example of the Contact-Type Staining Patch

Hereinafter, an experimental example of the above-described contact-type staining patch 100 according to an embodiment of the present disclosure will be described.

In this experimental example, the contact-type staining patch 100 according to an embodiment of the present disclosure is applied with a conventional Giemsa staining technique for an examination for malaria.

Since the Giemsa staining technique is merely described as a representative of Romanowsky staining techniques in various experimental examples which will be described below including this experimental example, embodiments are not limited to the Giemsa staining technique and may also be applied to other various Romanowsky staining techniques. In addition, a specimen staining technique performed using the contact-type patch 100 described herein has a simple procedure while effects of conventional Romanowsky staining techniques and other various staining techniques are maintained, and thus is expected to substitute therefor. A specimen staining technique will be referred to as "Noul stain" in a paper which will be written by the applicants in relation to the present disclosure.

The contact-type staining patch 100 was manufactured according to the following protocol.

1) After agarose, Giemsa powder, and the buffering solution B were mixed, the mixture was boiled and then cooled at room temperature. Agarose was used at 2% concentration, and the buffering solution B, which has a pH of 7.2, was used. Also, the mixture was heated to 100° C. or higher. Here, the concentration of agarose may be adjusted within a range of 1 to 3%. In addition, a pH concentration of the buffering solution B may be adjusted in a pH range of 6.4 to 7.6.

The contact-type staining patch 100 manufactured in this way was placed on blood smeared as a monolayer on the slide S for approximately five minutes, and then the staining result was observed using a 100× microscope. Blood collected from eyes of a mouse infected with *plasmodium* (a malaria-causing protozoan) was used.

Figure 7:
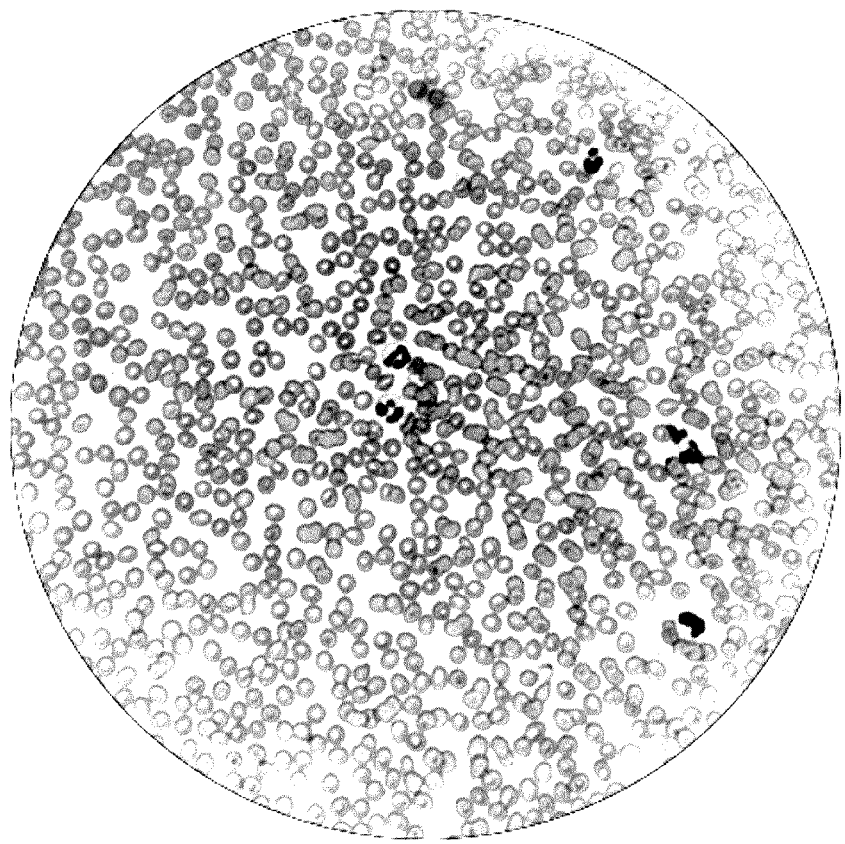
FIG. 7 is an image of a result of staining using a standard Giemsa stain process, i.e. a Giemsa staining technique according to a conventional fluid spraying means.
Figure 8:
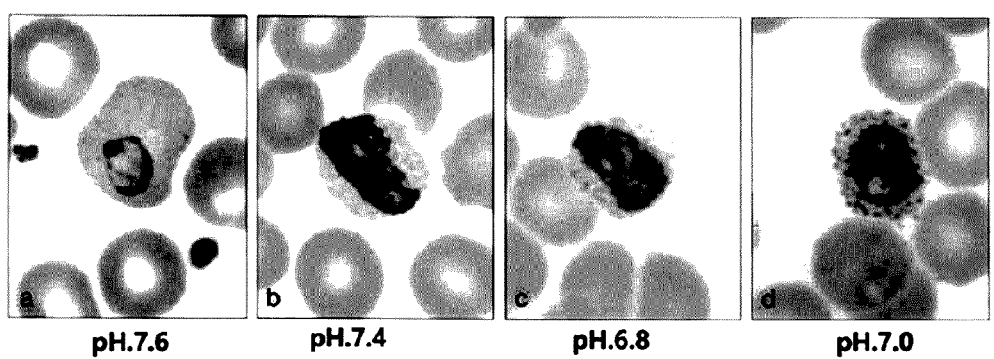
FIG. 8 shows images of results of staining using the Giemsa staining technique according to a standard Giemsa stain process for each pH concentration.
Figure 9:
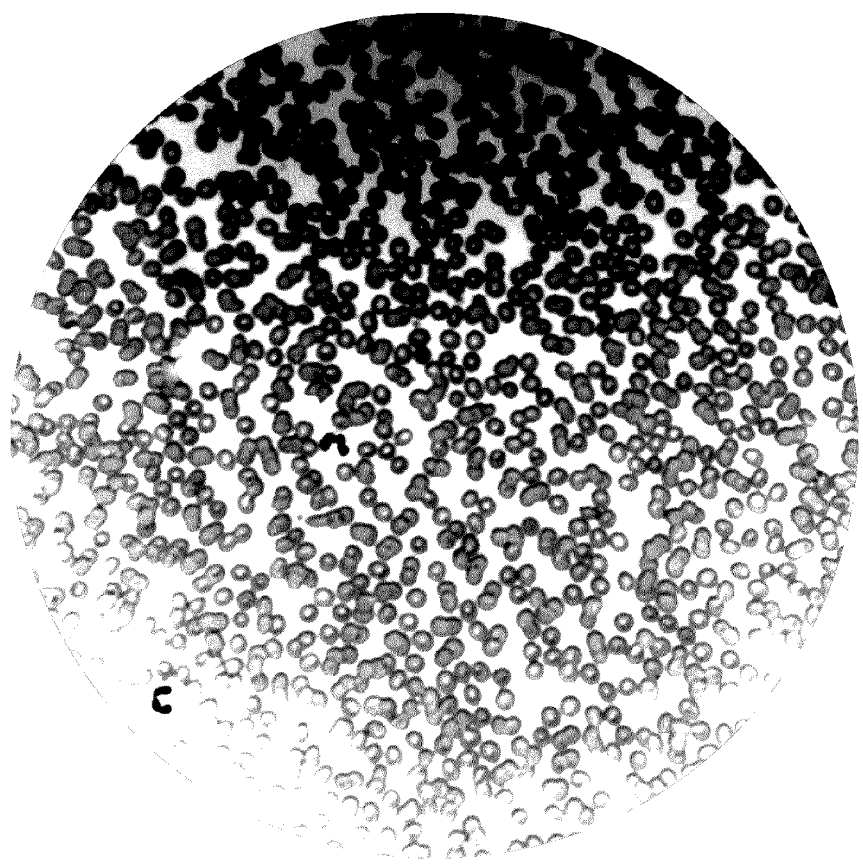
FIG. 9 is an image of a result of staining using the Giemsa staining technique in which the contact-type staining patch is applied according to an embodiment of the present disclosure.

FIG. 7 is an image of a result of staining using a standard Giemsa stain process, i.e. a Giemsa staining technique, according to a conventional fluid spraying means, FIG. 8 shows images of results of staining using the Giemsa staining technique according to a standard Giemsa stain process for each pH concentration, and FIG. 9 is an image of a result of staining using the Giemsa staining technique in which the contact-type staining patch 100 is applied according to an embodiment of the present disclosure.

FIG. 7 is a result of staining in which a suitable pH concentration of the Giemsa stain is followed whereas FIG. 8 is a result of staining of a case in which a pH concentration deviates from a proper value during a staining process. Referring to FIG. 9, a result in which the contact-type staining patch 100 above is applied in the Giemsa staining technique shows a similar result with a correct staining result in which a suitable pH concentration is followed. This suggests that staining using the contact-type staining patch 100 has been properly performed.

Particularly, a staining solution sprayed onto the slide S on which blood is smeared in the standard Giemsa stain process takes twenty to thirty minutes or more to stain. In contrast, when the contact-type staining patch 100 is used, the same result can be obtained within five minutes or less. Further, preparing a staining solution or washing, drying, etc. after staining is performed takes at least tens of minutes in the conventional standard process. In contrast, when the contact-type staining patch 100 is used, observation using a microscope is immediately possible after approximately tens of seconds of natural drying after staining is performed such that a time reduction effect is even greater.

The contact-type staining patch 100 for an examination the same as that above may also be manufactured according to the following protocol.

2) After 0.4 g of agarose is mixed with 20 ml of a mixed solution of the buffering solution B, which has a pH of 7.2, the mixture is heated for thirty seconds using a microwave and cooled while being stirred. Then, 1 ml of a Giemsa modified solution is mixed therewith, and the mixture is further cooled and then hardened to a gel phase.

The contact-type staining patch 100 manufactured in this way was placed on blood smeared as a monolayer on the slide S for approximately five minutes, and then the staining result was observed using a 100× microscope. Blood collected from eyes of a mouse infected with *plasmodium* (a malaria-causing protozoan) was used.

Figure 10:
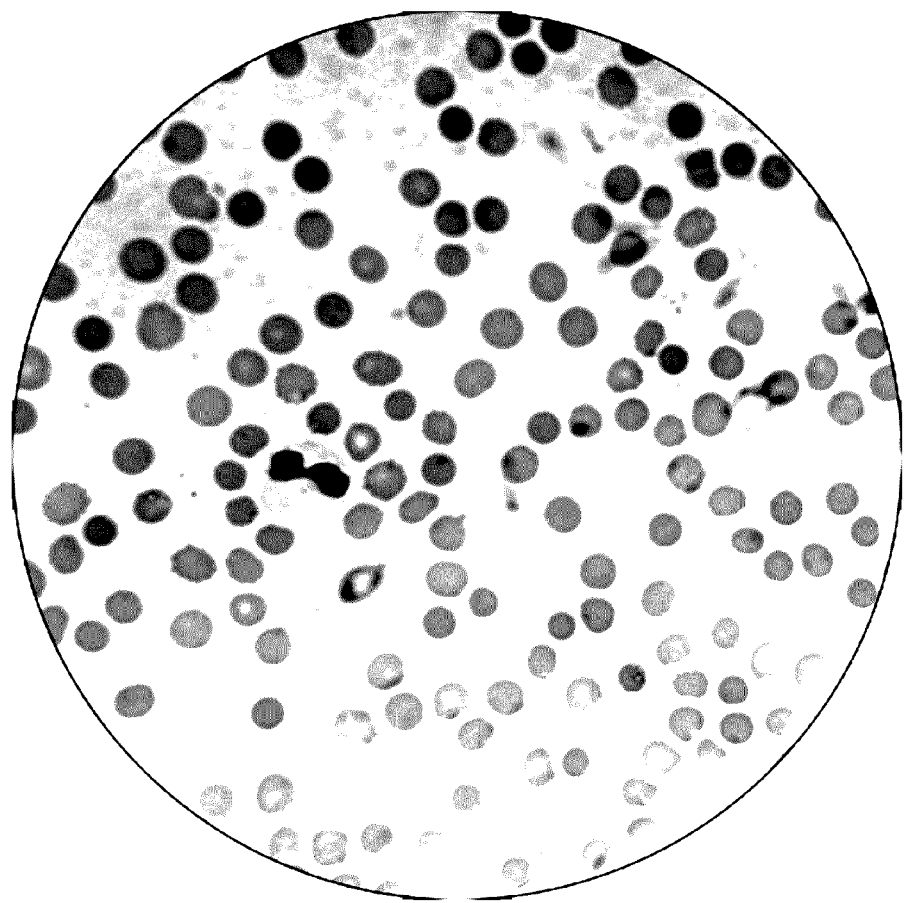
FIG. 10 is an image of another result of staining using the Giemsa staining technique in which the contact-type staining patch is applied according to an embodiment of the present disclosure.

FIG. 10 is an image of another result of staining using the Giemsa staining technique in which the contact-type staining patch 100 is applied according to an embodiment of the present disclosure. Referring to FIG. 10, a result in which the contact-type staining patch 100 manufactured using microwave baking as described above is applied in the Giemsa staining technique also shows a similar result with a correct staining result in which a suitable pH concentration is observed. Thus, this case also suggests that staining using the contact-type staining patch 100 has been properly performed.

In consideration of the staining results, the contact-type staining patch 100 according to an embodiment of the present disclosure is expected to have a more stable staining performance than a staining method that is performed according to the conventional standard process.

Although experimental examples in which the contact-type staining patch 100 is applied with the Giemsa staining technique have been described above, it can be easily understood that the contact-type staining patch 100 can also be applied to other different staining techniques.

Figure 11:
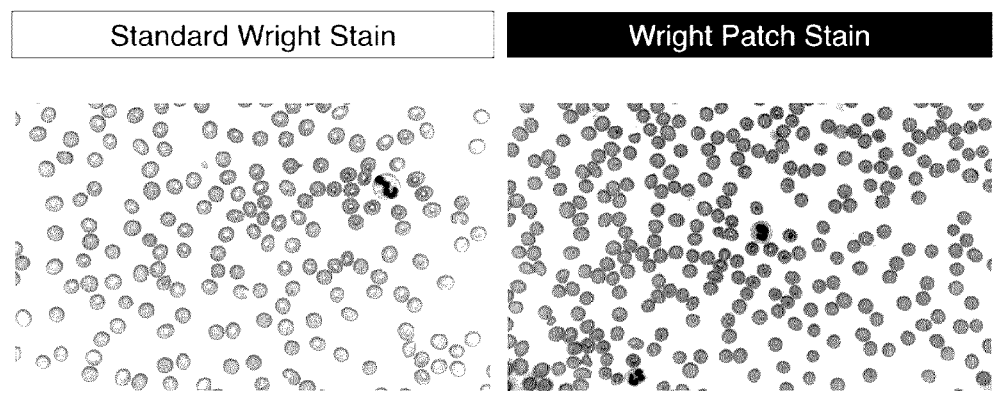
FIG. 11 is a view illustrating results according to a standard staining technique and a staining technique in which the contact-type staining patch is applied with respect to a Wright staining technique.

FIG. 11 shows results according to a standard staining technique and a staining technique in which the contact-type staining patch 100 is applied with respect to a Wright staining technique.

As a contact-type staining patch 100 for the Wright stain, a gel-phase contact-type staining patch 100 was manufactured using a staining solution in which the buffering solution B, which has a pH of 6.8, was mixed with the Wright staining reagent 140 and agarose. FIG. 11 shows a result of observation using a 400× microscope after the contact-type staining patch 100 was placed on the specimen T for approximately five minutes. As illustrated in FIG. 11, in the case of the Wright staining technique, it was also confirmed that a result was acquired almost the same as that acquired according to the standard process.

Figure 12:
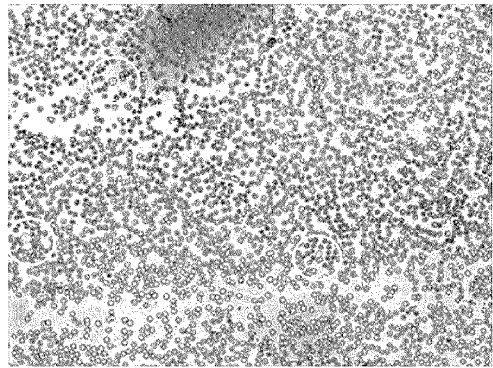
FIG. 12 is a view illustrating a result according to a staining technique in which the contact-type staining patch is applied with respect to a 4,6-diamidino-2-phenylindole (DAPI) staining technique.
Figure 12:
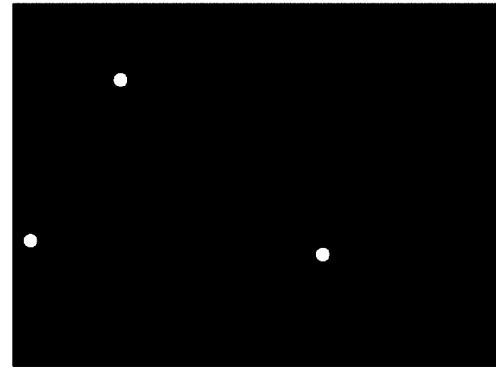

FIG. 12 shows results according to a staining technique in which the contact-type staining patch 100 is applied with respect to a DAPI staining technique.

As a contact-type staining patch 100 for a DAPI stain, a gel-phase contact-type staining patch 100 was manufactured using 0.4 g of agarose, 20 ml of PBS (Phosphate Buffer Saline), and 20 μl of DAPI. FIG. 12 shows results of observations which each used a Bright 20× and a Fluorescence 20× after the contact-type staining patch 100 was placed on the specimen T for approximately five minutes. As illustrated in FIG. 12, in the case of the DAPI staining technique, a stable fluorescent color formation was also confirmed as a result thereof.

In consideration of the staining results, the contact-type staining patch 100 according to an embodiment of the present disclosure is expected to simplify most of the standard processes of staining techniques that are conventionally performed and substitute therefor by guaranteeing a stable staining performance.

1.5. Utilization of the Contact-Type Staining Patch

In consideration of the above, representative examples of utilizing the contact-type staining patch 100 are as follows.

1.5.1 Staining Patch

In a conventional staining technique used in hematology, a liquid-phase staining solution is sprayed onto blood cells or tissue. However, with this method, residue remains on the specimen T, and it is difficult to control washing and drying processes, which are essential for removing the residue, to be regular. In addition, since a result is sensitive to changes according to a method of manufacture, a manufacture period, a change in a pH concentration of a buffer, etc. of staining reagents which are used, it is difficult to gain a stable staining result. Furthermore, the conventional standard processes requires various types of equipment and, due to a great complexity of a protocol using the equipment, it is extremely difficult for an unskilled person to carry out the protocol.

A staining patch is an innovative improvement of the conventional staining technique and basically refers to a gel-phase receptor that holds the staining reagent 140 in a hydrogel state. The staining patch may be manufactured by properly combining staining powder, hydrogel, the buffering solution B, a stabilizer, water, etc. as necessary and enables a simple protocol in which staining is completed by the manufactured staining patch being brought into contact with and separated from blood cells or tissue for a relatively short amount of time.

The method has advantages in that washing and drying processes can be omitted from an overall staining process, an amount of time for staining itself is short, there is no residue such as a stain remaining on the specimen T, the use of samples can be minimized, and results are regular and stable compared to the conventional method.

As a result, the staining patch creates a reaction condition (or an environmental condition) in a staining process while holding water such that a chemical reaction is induced between the staining reagent 140 and a substance to be reacted with while the water and other buffer substance are maintained as they are in the hydrogel, thereby eliminating the need for the washing and drying processes.

Representative examples of the staining patch may include Romanowsky staining patches, such as a Giemsa patch and a Wright patch, and a Papanicolaou staining patch.

1.5.2. Antibody Patch

In performing immunohistochemistry or an enzyme-linked immunosorbent assay (ELISA), an antibody patch is a patch capable of delivering an antibody or an antibody to which reporters, such as a fluorescent substance, are coupled, in a hydrogel state instead of a conventional liquid state.

Similar to the staining patch, the antibody patch is brought into contact with blood or a tissue for a predetermined amount of time. By this contact, antibodies contained inside a gel exit the antibody patch according to an antigen-antibody reaction, and the reaction ends.

When the antibody patch is used, a result may be obtained more promptly than the conventional means, washing and drying processes can be omitted, and background noise can be minimized.

1.5.3. DNA Patch

In performing the FISH test and the like, a DNA patch is a patch which delivers a DNA probe to which a fluorescent substance reporter is coupled, and is a patch that is delivered in a hydrogel state instead of a conventional liquid state.

Similar to the staining patch, the DNA patch is brought into contact with the specimen T such as blood, a tissue, or the like for a predetermined amount of time and then detached therefrom. By this contact, DNA probes exit the patch for hybridization, and the reaction ends.

Also in a DNA test, when the DNA patch is used, a more prompt and accurate result can be obtained compared to the conventional method, and washing and drying processes can be omitted.

Various examples of utilizing the contact-type staining patch 100 have been described above. However, fields in which the contact-type staining patch 100 can be utilized are not limited to those described above, and the contact-type staining patch 100 may be utilized in other various types of staining (a "wide meaning of staining" defined herein which means inducing detection when a specimen is tested). Here, the staining reagent 140 may be properly selected according to a field in which the contact-type staining patch 100 is utilized. For example, a staining substance may be used as the staining reagent 140 in a case of a staining patch; an antibody may be used as the staining reagent 140 in a case of an antibody patch; and a DNA probe may be used as the staining reagent 140 in a case of a DNA patch.

2. Contact-Type Staining Supplementary Patch

The contact-type staining patch 100 that contains the staining reagent 140 reacting with the specimen T, which is a substance to be reacted with, has been described above. Hereinafter, a contact-type staining supplementary patch 100' according to an embodiment of the present disclosure that performs other processes performed throughout a staining process, e.g., fixing or buffering, decolorizing, mordanting, washing, etc. of the specimen T will be described.

2.1. Examples of the Contact-Type Staining Supplementary Patch

Basically, a configuration of the contact-type staining supplementary patch 100' is substantially the same as that of the contact-type staining patch 100. Specifically, like the contact-type staining patch 100, the contact-type staining supplementary patch 100' includes the gel receptor 120 and may include a staining enhancing agent 160 instead of the staining reagent 140.

The staining enhancing agent 160 may be selected according to a field in which the contact-type staining supplementary patch 100' is used.

2.1.1. Fixing Patch

For example, when being used to fix the specimen T, the staining enhancing agent 160 may be a specimen fixing agent such as alcohol (ethanol, methanol, or the like) that fixes the specimen T onto the slide S and the like.

2.1.2. Decolorizing Patch and Mordanting Patch

In another example, when the staining enhancing agent 160 is used for decolorizing or mordanting, a decolorizing agent or a mordanting agent may be used as the staining enhancing agent 160. In a Gram staining technique, after both Gram-positive bacteria and Gram-negative bacteria are stained using crystal violet as a main staining agent, the main staining agent is fixed to the Gram-positive bacteria using iodine as the mordanting agent, the main staining agent not fixed to the Gram-negative bacteria is then peeled off from the Gram-negative bacteria using a decolorizing agent such as alcohol (ethanol, methanol, etc.), and the decolorized Gram-negative bacteria is stained using safranin as a contrast staining agent such that the Gram-positive bacteria are stained by the main staining agent and the Gram-negative bacteria are stained by the contrast staining agent, and thus the two exhibit colors different from each other as a result. In this process, when actual staining is constituted only of the main staining agent and the contrast staining agent, the mordanting agent and the decolorizing agent do not perform staining itself but perform roles of assisting in staining. In the Gram staining technique, a main staining patch that uses crystal violet (a main staining agent) as the staining reagent 140 and a contrast staining patch that uses safranin O (a contrast staining agent) as the staining reagent 140 are prepared as the contact-type staining patch 100 according to an embodiment of the present disclosure, and a mordanting patch that contains iodine (a mordanting agent) as the staining enhancing agent 160 and a decolorizing patch that contains alcohol (a decolorizing agent) as the staining enhancing agent 160 are prepared as the contact-type staining supplementary patch 100' according to an embodiment of the present disclosure such that the Gram staining technique can be performed by bringing the main staining patch, the mordanting patch, the decolorizing patch, and the contrast staining patch into contact with the specimen T in that order.

When the contact-type staining supplementary patch 100' such as the fixing patch and the decolorizing patch is manufactured using the fixing agent or the decolorizing agent described above, a non-hydrogel may be mainly used for a material of the gel receptor 120 (of course, hydrogel may also be used according to circumstances). Alcohol with a high concentration (e.g., 99% or higher) may have to be used as the fixing agent to fix the specimen T on the slide S. Here, when hydrogel is used, the concentration of alcohol may be lowered due to an interaction between the gel receptor 120 and the alcohol, and accordingly, a fixing action may be degraded. In contrast, when the gel receptor 120 is a non-hydrogel, the concentration of alcohol can be maintained relatively well in the above case, and thus fixing performance or decolorizing performance can be improved. A PDMS gel, a PMMA gel, a silicone gel, or the like may be used as the non-hydrogel.

In addition, the fixing patch or the decolorizing patch may also be replaced with a fixing agent or a decolorizing agent that are a result of solidifying the gel receptor 120. For example, solidified-methanol itself may also be used as the fixing patch or the decolorizing patch.

2.1.3. Buffering Patch

In yet another example, there may be a buffering patch that uses the buffering solution B as the staining enhancing agent 160. The buffering patch may be a patch that creates a reaction condition (an environmental condition) for staining at the specimen T by coming into contact with the specimen T before, after, or both before and after the staining of the specimen T. In the case of the Giemsa stain, the buffering patch may be provided in a form in which the buffering solution B having a suitable pH for the Giemsa stain is accommodated in the gel receptor 120 as the staining enhancing agent 160.

A pH of the buffering solution B to be contained in the buffering patch may be substantially the same as a pH according to the reaction condition, i.e., an optimal pH.

Alternatively, unlike the above, the pH of the buffering solution B may be somewhat different from the optimal pH for a reaction.

When staining is performed, creating a proper staining environment, in particular, creating a suitable pH, may be an important factor for properly performing staining. Generally, in a buffering step of the conventional staining procedure, a pH condition is set by spraying or dripping the buffering solution B having an optimal pH onto a specimen that is stained, being stained, or will be stained. In contrast, in a buffering step using the contact-type staining supplementary patch 100', a pH condition is created in a specimen by bringing the buffering patch into contact with the specimen T. Consequently, the contact-type staining supplementary patch 100' causes a buffering action in the specimen T according to a mechanism different from a conventional means in which a buffering solution in a liquid phase is brought into contact with a specimen.

Specifically, when a buffering patch manufactured using the buffering solution B that has an approximate pH of 6.5 is brought into contact with the specimen T that is stained and the stained specimen T is observed, a staining result similar to a result of spraying the buffering solution B, which has an approximate pH of 6.6 to 6.9, onto the specimen T that is stained is actually observed.

Conversely, when a buffering patch manufactured using the buffering solution B that has an approximate pH of 7.6 is brought into contact with the specimen T that is stained and the specimen T is observed, a staining result similar to a result of spraying the buffering solution B, which has an approximate pH of 7.2 to 7.4, onto the specimen T that is stained is actually observed.

In consideration of the point above, it can be recognized that a pH created in the specimen T when the buffering solution B is provided on the specimen T while being contained in the gel receptor 120 is somewhat more biased toward a neutral pH than a pH created when the buffering solution B is directly sprayed onto the specimen T in a liquid phase. This is because, when the buffering solution B is directly provided using the buffering patch, an acid-base interaction that occurs between the buffering solution B and the specimen T occurs through the mesh structure of the gel matrix and thus may be somewhat more delayed than an acid-base interaction between the buffering solution B sprayed in a liquid phase and the specimen.

In other words, an effective pH of the buffering patch manufactured using the buffering solution B, which has a specific pH value, is somewhat more biased toward a neutral pH than a pH value of the buffering solution B itself. Here, the effective pH refers to a pH acting on the specimen T and may be, for example, a pH created in the specimen T when the buffering solution B in a liquid phase is sprayed onto the specimen.

Consequently, when the buffering patch is being manufactured, a pH of the buffering solution B may be adjusted so that an effective pH value of the buffering patch is substantially the same as an optimal pH value of a staining technique in which the buffering patch will be used for buffering.

That is, a pH value of the buffering solution B itself that will be used in the buffering patch may be set as a value compensated for by a pH compensation value in consideration of an extent to which an acid-base interaction is hindered by the gel matrix with respect to an optimal pH value which facilitates staining that may be defined in a conventional staining technique.

Here, the pH compensation value may be a negative value when the optimal pH is acidic. For example, the pH compensation value may be −0.3 when the optimal pH is 6.8, and accordingly, a pH value of the buffering solution B used when the buffering patch is manufactured may be a pH of 6.5 for the effective pH of 6.8.

In addition, here, the pH compensation value may be a positive value when the optimal pH is basic. For example, the pH compensation value may be +0.2 when the optimal pH is 7.4, and accordingly, a pH value of the buffering solution B used when the buffering patch is manufactured may be a pH of 7.6 for the effective pH of 7.4.

a magnitude (i.e., an absolute value) of the pH compensation value may be increased or decreased according to a concentration, a hardness, porosity, a density of a mesh structure, etc. of the gel of the gel receptor 120.

The magnitude of a pH compensation value may increase as a concentration of the gel of the gel receptor 120 increases, and the size of the pH compensation value may decrease as the concentration of the gel lowers. For example, when agarose gel is used as the gel receptor 120, the size of the pH compensation value may increase as a concentration of agarose increases, and the size of the pH compensation value may decrease as a concentration of agarose lowers.

In addition, the magnitude of the pH compensation value may increase as the gel receptor 120 hardens, and the magnitude of the pH compensation value may decrease as the gel receptor 120 softens.

In addition, the size of the pH compensation value may decrease as the porosity of the gel receptor 120 increases, and the size of the pH compensation value may increase as the porosity decreases.

In addition, the size of the pH compensation value may increase as the density of the mesh structure of the gel receptor 120 increases, and the size of the pH compensation value may decrease as the density lowers.

A pH shift phenomenon of the buffering patch is caused by a cause different from a case in which a pH of the buffering solution B is shifted when the staining reagent 140 is mixed with the buffering solution B in the contact-type staining patch 100. That is, although pH shifting in the buffering patch occurs due to a cause described just above, pH shifting in the contact-type staining patch 100 may occur due to a complex cause that includes the cause described just above and a cause according to a part of description related to the buffering solution B of the contact-type staining patch 100.

The above description on the pH compensation of the buffering solution B is not applied only to the buffering solution B included in the buffering patch but may be generally applied to the contact-type staining patch 100 or the contact-type staining supplementary patch 100' that has the buffering solution B. For example, even when the staining reagent 140 included in the contact-type staining patch 100 is in a form of a solution in which a staining powder is mixed with the buffering solution B, a pH value that results from adding or subtracting a pH compensation value to or from an optimal pH may be set as a pH value of the buffering solution B instead of making the pH value of the buffering solution B correspond to the optimal pH.

2.1.4. Washing Patch

In still another example, there may be a washing patch. The washing patch is a patch that performs washing during a staining process and, somewhat different from the contact-type staining supplementary patch 100' described above, may not include a separate staining enhancing agent 160 or may use a small amount of water, alcohol, or the like as the staining enhancing agent 160.

The washing patch comes into contact with the specimen T to perform a role of removing foreign substances and the like remaining on the specimen T. For example, when a dye, a mordanting agent, a decolorizing agent, a fixing agent, or the like is applied to the specimen T during a staining process, some of whatever is applied remains on the specimen T and needs to be washed away. When the washing patch is brought into contact with the specimen T, the specimen T may be washed as a foreign substance is absorbed into a pore of the gel matrix of the washing patch. This is due to a property of the washing patch for absorbing a contacted foreign substance since the washing patch does not contain a solution and the like therein or contains only a small amount thereof.

Since the washing patch also performs a function of absorbing a liquid on the specimen T and simultaneously performs washing and drying the specimen T in the staining process, the washing patch may also be referred to as a drying patch.

The washing and drying functions of the washing patch may also be performed by the buffering patch rather than the washing patch. In a case of the buffering patch, since a relatively larger amount of solution is included inside the gel receptor 120 compared to the washing patch, performance of absorbing a foreign substance on the specimen T when brought into contact with the specimen T may be somewhat low. However, since the gel receptor 120 of the buffering patch also has some pores, the buffering patch may somewhat perform a function of absorbing residue on the specimen T. As a result, the buffering patch is able to perform some of washing and drying roles besides a buffering role in which an optimal pH is set with respect to the specimen T. Thus, in the staining process, buffering, washing, and drying are performed only by simply bringing the buffering patch into contact with the specimen T, and accordingly, the staining process can be simplified. Of course, performing separate washing and drying processes is possible when an excessive amount of residue is present.

An absorbent may also be contained as the staining enhancing agent 160 in the gel receptor 120 of the washing patch to reinforce an absorption force of the washing patch. The porosity of the gel receptor 120 may be improved by not including a separate solution in the gel receptor 120 or including only a small amount of a solution therein as described above so that a foreign substance may be well-absorbed from the specimen T it contacts. However, when the absorbent is included as the staining enhancing agent 160 in the gel receptor 120 to further improve the absorption force, an absorption rate may be improved by absorbing the foreign substance on the specimen T with which the absorbent has come into contact.

2.1.5. Composite Patch

Although each function of the contact-type staining supplementary patch 100' has been described above, the staining supplementary patch may simultaneously have two or more functions in some cases.

For example, the buffering patch may simultaneously perform a role of buffering a reaction condition such as a pH concentration at the specimen T which is stained and a role of washing residue remaining on the specimen T. Although there is substantially almost no residue remaining on the specimen T when the specimen T is stained using the contact-type staining patch 100 according to an embodiment of the present disclosure, even an infinitesimal amount of residue that may be present at the specimen T may be clearly removed when the contact-type staining patch 100 is detached from the specimen T and then the buffering patch is brought into contact with the specimen T.

Although it has been described above that the contact-type staining supplementary patch 100' is implemented with one patch for each role, one contact-type staining supplementary patch 100' may contain a composite staining enhancing agent 160 and perform two or more roles unlike the above description.

For example, the mordanting patch and the decolorizing patch may be implemented as one mordanting-and-decolorizing patch. The mordanting-and-decolorizing patch in which the mordanting agent and the decolorizing agent are simultaneously contained as staining enhancing agents 160 in the gel receptor 120 may simultaneously perform mordanting and decolorizing of the specimen T when brought into contact with the specimen T.

Furthermore, the contact-type staining patch 100 and the contact-type staining supplementary patch 100' may also be implemented by being combined with each other. For example, when the main staining agent, the mordanting agent, the decolorizing agent, and the contrast staining agent for the Gram staining technique may be accommodated in the gel receptor 120, the contact-type staining patch 100 and the contact-type staining supplementary patch 100' may be implemented using one patch (hereinafter referred to as a "composite patch").

The composite patch simplifies the staining process greatly, thus having an advantage of being convenient to use. However, when reactions occur between staining reagents 140, between staining enhancing agents 160, and between the staining reagents 140 and the staining enhancing agents 160 inside the gel receptor 120, staining may fail or an erroneously stained result may be obtained. Thus, the composite patch should be used in proper consideration of its advantages and disadvantages.

2.2. Method of Manufacturing a Contact-Type Staining Supplementary Patch

Hereinafter, a method of manufacturing the above-described contact-type staining supplementary patch 100' according to an embodiment of the present disclosure will be described.

An example of the method of manufacturing the contact-type staining supplementary patch 100' may include forming the gel receptor 120 and absorbing the staining enhancing agent 160 into the gel receptor 120.

First, the gel receptor 120 is formed using a gel raw material that serves as a gel formation substance, a gelable substance, etc. such as agarose powder and the like. For example, the gel receptor 120 may be manufactured when agarose powder and water are mixed at a proper ratio, and the mixture is heated and cooled. Here, boiling the mixture, baking the mixture using a microwave, or the like may be used as the heating method. In addition, here, the cooling method may include natural cooling or forced cooling, and a stirring process may be included in the cooling method as necessary.

Next, the staining enhancing agent 160 can be absorbed into the manufactured gel receptor 120. To absorb the staining enhancing agent 160 into the gel receptor 120, a method in which the gel receptor 120 is dipped in a chamber, a container, or the like in which the staining enhancing agent 160 is accommodated for a predetermined amount of time and the gel receptor 120 is then taken out after the staining enhancing agent 160 is sufficiently absorbed thereinto may be used.

In another example, the method of manufacturing the contact-type staining supplementary patch 100' may include a method in which a gel raw material, an aqueous solution, and a staining reagent are mixed to form a gel receptor. For example, the contact-type staining supplementary patch 100' may be manufactured by mixing agarose, an aqueous solution (or a buffering solution), and the staining enhancing agent 160 at a proper ratio, and heating and cooling the mixture. Here, the heating and cooling means may be similar to the examples described above.

In yet another example, the method of manufacturing the contact-type staining supplementary patch 100' may include a method in which a gel base material and a solution are mixed and heated, and the staining enhancing agent 160 is then added during a process of cooling the heated mixture. For example, after agarose and an aqueous solution are mixed at a proper ratio and heated, the staining enhancing agent 160 is added during a process of cooling the heated mixture.

2.3. Experimental Example of the Contact-Type Staining Supplementary Patch

Hereinafter, an experimental example of the above-described contact-type staining supplementary patch 100' according to an embodiment of the present disclosure will be described.

In this experimental example, the contact-type staining patch 100 and the contact-type staining supplementary patch 100' according to an embodiment of the present disclosure are applied in the conventional Giemsa staining technique for an examination for malaria.

Two contact-type staining patches 100 were manufactured to respectively have methylene blue and eosin, which are Giemsa staining reagents 140, as one reagent Manufacturing a plurality of patches for each reagent as above may have an advantage in which a storage period of the contact-type staining patch 100 is longer than in a case in which the patch is manufactured by mixing two staining reagents 140 in one patch. To give a concrete example, when methylene blue and eosin are mixed and accommodated in one contact-type staining patch, methylene blue, which is basic, and eosin, which is acidic, may react with each other as time passes, and thus reactivity with respect to the specimen T may be degraded. On the other hand, when the contact-type staining patch 100 is separately manufactured for methylene blue and eosin, such a problem may be mitigated.

A specific manufacturing protocol is as follows.

1) After agarose, methylene blue, and the buffering solution B were mixed, the mixture was boiled or baked using a microwave and then cooled at room temperature to manufacture a methylene blue staining patch.

2) After agarose, eosin, and the buffering solution B were mixed, the mixture was boiled or baked using a microwave and then cooled at room temperature to manufacture an eosin staining patch.

In processes 1) and 2), agarose having a concentration of 1 to 5% was used, and a pH concentration of the buffering solution B was set as an optimal pH of the staining reagent 140 in each case.

Then, the contact-type staining supplementary patch 100' was manufactured according to the following protocol.

3) After only agarose and the buffering solution B were mixed without the staining reagent 140, the mixture was boiled or baked using a microwave and then cooled at room temperature to manufacture a buffering patch. Here, a PBS solution having a pH of 7.2 was used as the buffering solution B.

The methylene blue patch, the eosin patch, and the buffering patch manufactured as above were sequentially brought into contact with and detached from blood smeared on the slide S in that order. Here, the methylene blue patch was brought into contact with the blood for approximately thirty seconds and the eosin patch was brought into contact with the blood for approximately one minute. Then, the buffering patch was brought into contact with the blood for approximately three minutes.

Figure 13:
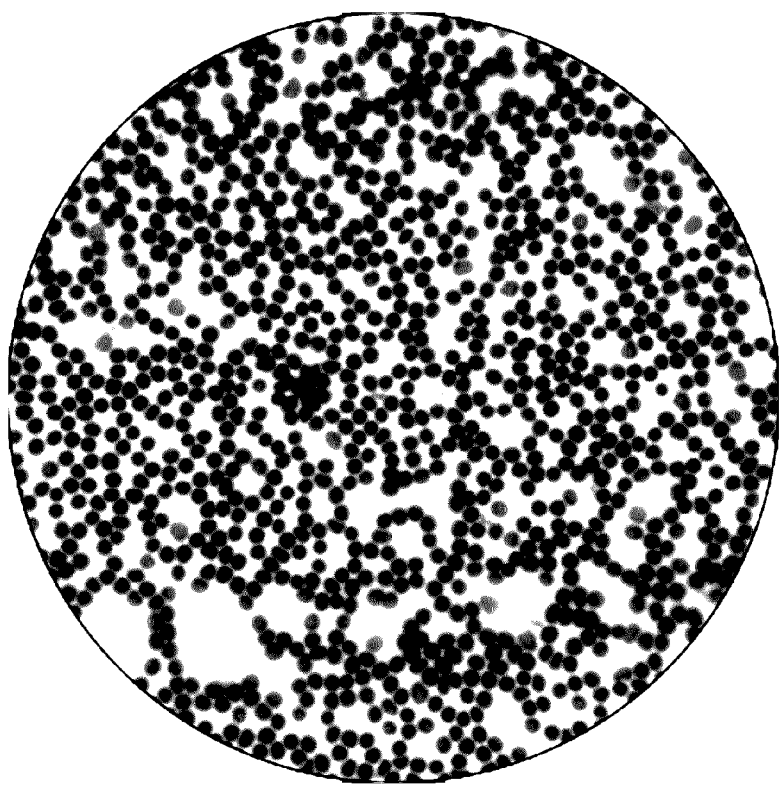
FIG. 13 is a view illustrating a staining result observed before a buffering patch is brought into contact with blood after a methylene blue patch and an eosin patch are brought into contact with the blood.
Figure 14:
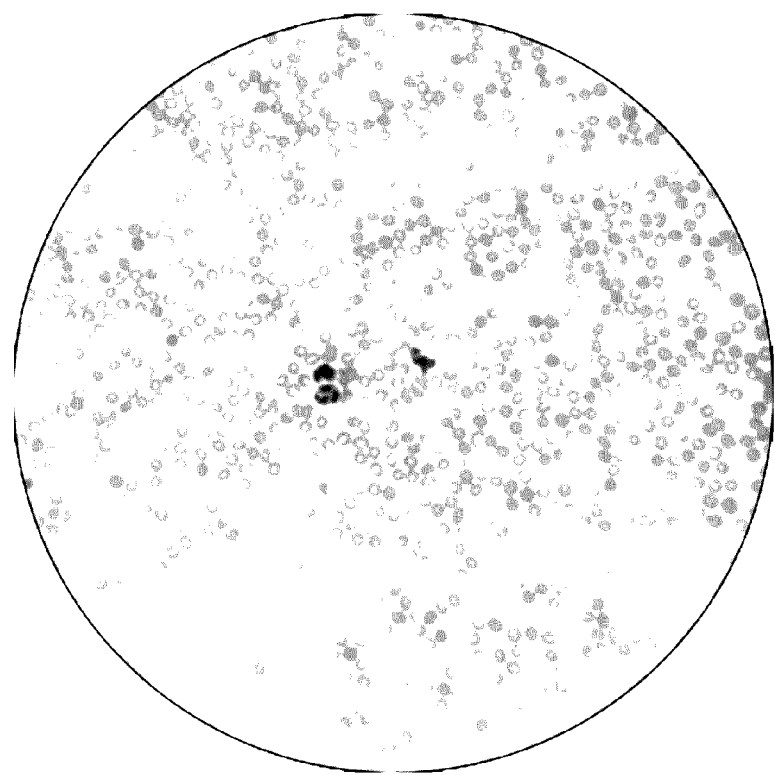
FIG. 14 is a view illustrating a staining result observed after the buffering patch is brought into contact with blood after the methylene blue patch and the eosin patch are brought into contact with the blood.

FIG. 13 is a view illustrating a staining result observed before a buffering patch is brought into contact with blood after a methylene blue patch and an eosin patch are brought into contact with the blood, and FIG. 14 is a view illustrating a staining result observed after the buffering patch is brought into contact with blood after the methylene blue patch and the eosin patch are brought into contact with the blood.

When FIGS. 13 and 14 are compared, it can be recognized that FIG. 14 is more similar to a result of normal staining according to a standard staining process of the Giemsa stain. Specifically, in FIG. 13, a blue color (methylene blue) is intensively stained compared to FIG. 14, and a red color stained by eosin is relatively not observed. This is because a reaction of eosin applied to blood later is hindered by methylene blue that has come into contact with blood before the eosin. When the buffering patch is brought into contact with blood in this state, normal staining is performed by decreasing an excessive reaction of methylene blue while increasing an insufficient reaction of eosin as a reaction condition (a pH concentration and the like) on the blood is adjusted to an optimal pH which is proper for the reaction.

In addition, when FIGS. 13 and 14 are closely examined, it can be recognized that stains and the like (an upper left side in FIG. 11) that were observed before the contact with the buffering patch were removed after the contact with the buffering patch.

In consideration of these points, when the staining reagents 140 are used in combination, it can be recognized that the buffering patch simultaneously performs a function of properly creating a reaction condition so that each of the staining reagents 140 reacts well and a function of washing to remove a foreign substance.

In addition, since an excessive amount of the buffering solution B contained in the buffering patch is not moved toward blood, i.e., the specimen T, an additional drying procedure may be omitted or only a minimal drying procedure may be required.

3. Test Kit

Hereinafter, a test kit according to an embodiment of the present disclosure will be described.

The test kit according to an embodiment of the present disclosure may have the contact-type staining patch 100 contained therein to stain the specimen T when the specimen T is inserted thereinto.

3.1. Form of the Test Kit

The test kit may include two plates. Here, one of the two plates may be a plate (hereinafter, referred to as "patch plate") that contains the contact-type staining patch 100, and the other one of the two plates may be a plate (hereinafter, referred to as "specimen plate") on which the specimen T is smeared.

In the test kit, the two plates, i.e. the patch plate and the specimen plate, may be coupled to be movable relative to each other. Here, movement is a concept that encompasses rotation and sliding.

In the test kit, when the specimen T is smeared on the specimen plate, the patch plate may move relative to the specimen plate so that the contact-type staining patch 100 stored in the patch plate is disposed at a point at which the specimen T is smeared, and the specimen T and the staining patch may be brought into contact with each other so that the specimen T is stained.

In the present disclosure, the test kit may be designed in various forms. Typical forms of the test kit include a rotating type and a sliding type.

Figure 16:
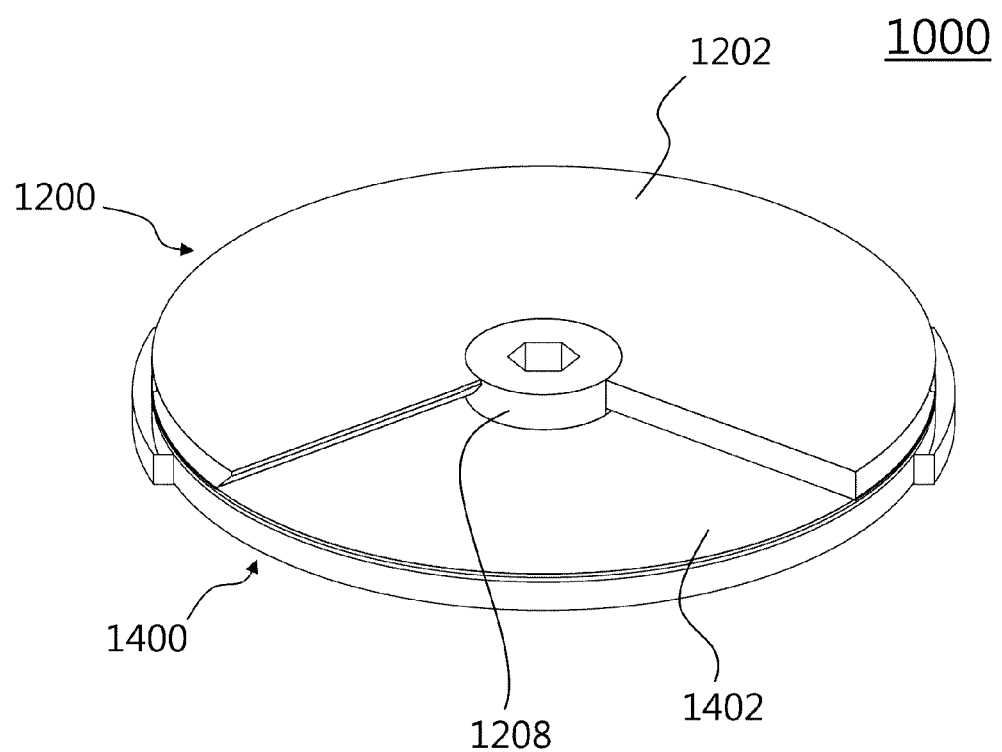
FIG. 16 is a perspective view of the example of the rotating-type test kit according to an embodiment of the present disclosure.
Figure 30:
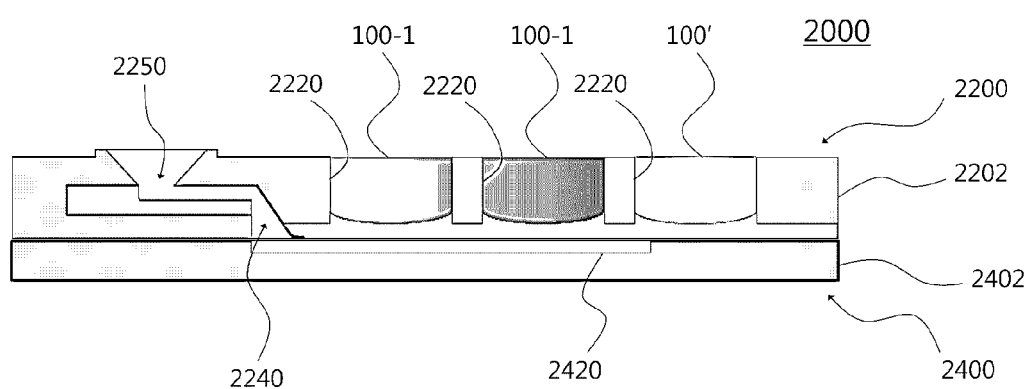
FIG. 30 is a side view of an example of a sliding type test kit according to an embodiment of the present disclosure.

FIG. 16 is a perspective view of an example of a test kit 1000, which is a rotating-type test kit, according to an embodiment of the present disclosure, and FIG. 30 is a side view of an example of test kit 2000, which is a sliding type test kit, according to an embodiment of the present disclosure.

Here, the test kits are differentiated in accordance with means of relative movement between a patch plate and a specimen plate. In the rotating-type test kit 1000, a staining patch is placed on a smearing region of a specimen T as the two plates rotate relative to each other. In the sliding type test kit 2000, a staining patch is placed on a smearing region of a specimen T as the two plates slide relative to each other.

As illustrated in FIGS. 16 and 30, generally, rotating-type test kits 1000 may mostly have a disc shape, and sliding type test kits 2000 may mostly have a quadrilateral flat plate shape.

In the test kits having the above-mentioned shapes, a patch plate may mostly be placed above a specimen plate. An opening or a loading unit for specimen insertion may be provided in the patch plate, and a specimen may be moved to the specimen plate through such an opening or a loading unit. Also, a smearing unit for smearing a specimen in the specimen plate may be provided in the patch plate, and a specimen T may be smeared in the specimen plate as the patch plate and the specimen plate move relative to each other. In the patch plate, a staining patch may be contained to face the specimen plate, and the staining patch may be placed on an region in which the specimen T is smeared as the specimen plate and the patch plate move relative to each other. When the staining patch is placed on the region in which the specimen T is smeared, a gap between the patch plate and the specimen plate may be reduced or the shape or position of the staining patch may be deformed toward the specimen plate to allow contact between the specimen T and the staining patch.

Hereinafter, the two types of test kits will be described in more detail. However, the rotating-type test kit 1000 and the sliding type test kit 2000, which will be described below, are merely examples of test kits according to an embodiment of the present disclosure, and the rotating-type test kit 1000 and the sliding type test kit 2000 are not limited by the description below. Furthermore, the test kits 1000 and 2000 are also merely an example for describing forms of test kits according to an embodiment of the present disclosure, and it should be noted that the forms of test kits according to an embodiment of the present disclosure are not limited to the rotating-type test kit 1000 and the sliding type test kit 2000.

3.2. Structure of Rotating-Type Test Kit

First, a rotating-type test kit 1000 will be described.

Figure 15:
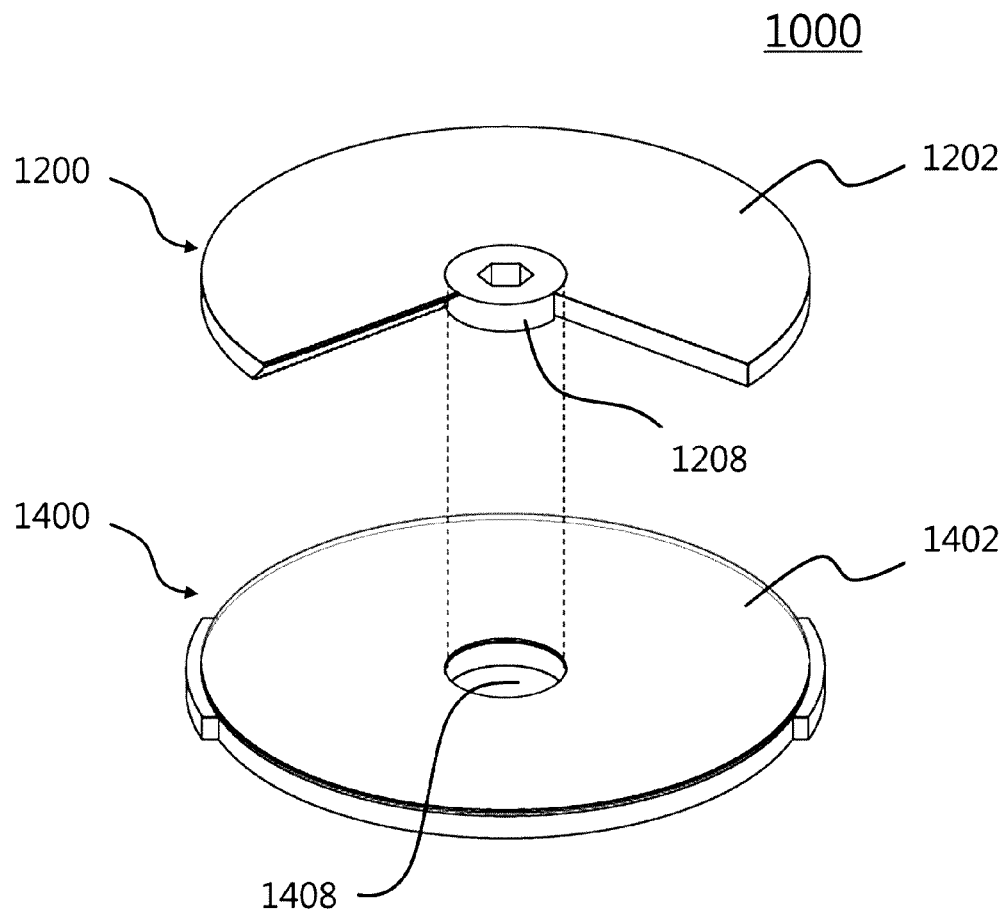
FIG. 15 is an exploded perspective view of an example of a rotating-type test kit according to an embodiment of the present disclosure.

FIG. 15 is an exploded perspective view of an example of the rotating-type test kit 1000 according to an embodiment of the present disclosure, and FIG. 16 is a perspective view of the example of the rotating-type test kit 1000 according to an embodiment of the present disclosure.

Referring to FIGS. 15 and 16, in the test kit 1000, a specimen plate 1400 may have a disc-shaped body 1402. A patch plate 1200 may have a body 1202 in the shape of a disc with an incised portion (e.g., a sector-shaped plate). The patch plate 1200 and the specimen plate 1400 may be provided to face each other and may be coupled to each other to be rotatable relative to each other at a central portion of the disc or the sector-shaped plate.

The bodies 1202 and 1402 of the patch plate 1200 and the specimen plate 1400 may each have an inner surface, an outer surface, and a side surface. Here, the inner surfaces are surfaces of the patch plate 1200 and the specimen plate 1400 that face each other, and the outer surfaces are surfaces opposite the inner surfaces. That is, an inner surface 1204 of the patch plate 1200 is a surface close to the specimen plate 1400, an outer surface of the patch plate 1200 is a surface away from the specimen plate 1400, an inner surface 1404 of the specimen plate 1400 is a surface close to the patch plate 1200, and an outer surface of the specimen plate 1400 is a surface away from the patch plate 1200.

The patch plate 1200 and the specimen plate 1400 may be coupled to each other at central portions thereof. For example, as illustrated in FIGS. 15 and 16, a coupling protrusion 1208 that protrudes toward the inner surface may be formed on any one of the central portions of the patch plate 1200 and the specimen plate 1400, and a coupling hole 1408 or a coupling groove may be formed at the other central portion such that the patch plate 1200 and the specimen plate 1400 may be coupled to each other by the coupling protrusion 1208 being inserted into the coupling hole 1408 or the coupling groove. Here, to stabilize coupling between the two plates, a nut may be connected to an end portion of the coupling protrusion that has passed through the coupling hole, a wing that extends in a diameter direction from the end portion of the coupling protrusion may be formed, or the two plates may be coupled to each other using a separate pin.

The patch plate 1200 and/or the specimen plate 1400 may be provided with a transparent or semitransparent material. When the patch plate 1200 and/or the specimen plate 1400 is transparent or semitransparent, there may be an advantage in which an operator can check a staining process using the test kit 1000 with visual inspection.

3.2.1. Structure of the Patch Plate

Figure 17:
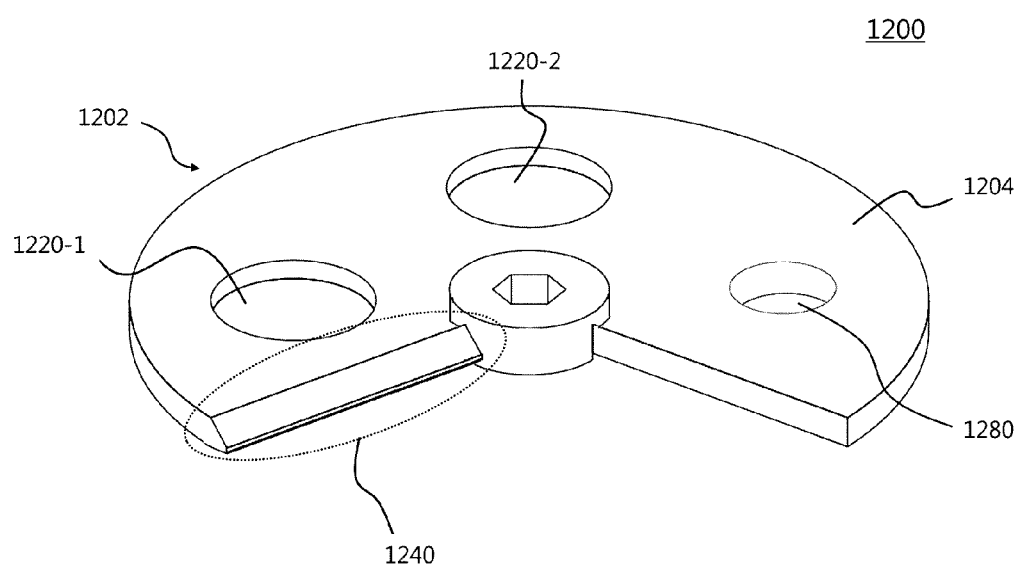
FIG. 17 is a perspective view of an example of a patch plate of the rotating-type test kit according to an embodiment of the present disclosure.

FIG. 17 is a perspective view of an example of the patch plate 1200 of the rotating-type test kit 1000 according to an embodiment of the present disclosure.

Referring to FIG. 17, the patch plate 1200 may have a body in the shape of a disc with an incised portion (e.g., a sector-shaped plate).

A storage 1220 configured to store the contact-type staining patch 100 or the contact-type staining supplementary patch 100' may be formed in the body. Hereinafter, the contact-type staining patch 100 and the contact-type staining supplementary patch 100' will be collectively referred to as a "contact-type patch."

The storage 1220 may be formed on a sector-shaped region of the patch plate 1200 and, more particularly, may be formed at a position spaced apart from the center of the patch plate 1200 by a predetermined distance in a radial direction thereof.

One or a plurality of storages 1220 may be formed in the patch plate 1200. For example, when attempting to stain blood according to the Giemsa staining technique, the number of storages 1220 of the patch plate 1200 may be as follows. At the patch plate 1200, 1) only one storage 1220 for storing only a methylene blue-eosin patch (the contact-type staining patch 100 that simultaneously contains two staining reagents 140, methylene blue and eosin) may be formed, 2) only two storages 1220 for storing the methylene blue patch and an eosin patch, respectively, may be formed, or 3) three storages 1220 for storing the methylene blue patch, the eosin patch, and a buffering patch, respectively, may be formed. For reference, FIG. 17 illustrates the patch plate 1220 at which two storages 1220 are formed.

When there are a plurality of storages 1220, an angle formed by each of the storages 1220 with respect to the center of the patch plate 1200 when viewed in a direction of the inner surface of the patch plate 1200 may be uniform. For example, from the center of the patch plate 1200, an angle between a first storage 1220-1 and a second storage 1220-2 and an angle between the second storage 1220-2 and a third storage 1220-3 may be 45°. When angular intervals between the storages 1220 are set to be equal to each other, there is an advantage in which it is easy to control a diagnostic device, which will be described below, since the contact-type patches can be sequentially brought into contact with the specimen T by the body being rotated by the same angle each time.

The storage 1220 may contain the contact-type staining patch 100 or the contact-type staining supplementary patch 100' so that the contact-type staining patch 100 or the contact-type staining supplementary patch 100' is exposed in a direction of the inner surface of patch plate 1200.

For example, as illustrated in FIG. 17, the storage 1220 may be formed in the form of a groove. The groove may be in a form that is open in the direction of the inner surface of the patch plate 1200, i.e. a form that is recessed in the direction of the inner surface of the patch plate 1200. Accordingly, the contact-type patch contained in the storage 1220 may come into contact with the specimen T to be applied onto the specimen plate 1400.

Here, the groove may have a form corresponding to the contact-type patch to be contained therein.

Although the contact-type patch may be manufactured in various shapes, for convenience of description, a description will be given on the basis of a contact-type patch manufactured in a cylindrical or polygonal cylindrical shape having main surfaces, which are an upper surface and a lower surface having a circular or polygonal shape, and side surfaces that connect the upper surface and the lower surface. Of course, the contact-type patch may also be manufactured in various other shapes including a hemispherical shape, a cylindrical or polygonal cylindrical shape in which sizes of an upper surface and a lower surface are different, and a cylindrical or polygonal cylindrical shape in which a side surface has a convex shape.

Figure 18:
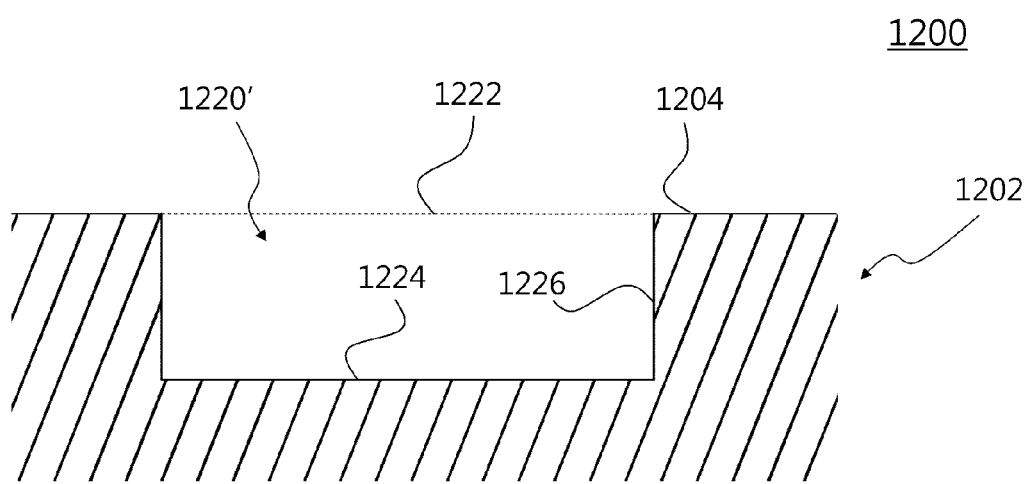
FIG. 18 is a cross-sectional view of an example of a groove-shaped storage of the rotating-type test kit according to an embodiment of the present disclosure.

FIG. 18 is a cross-sectional view of an example of a groove-shaped storage 1220 of the rotating-type test kit 1000 according to an embodiment of the present disclosure.

Referring to FIGS. 17 and 18, a groove 1220' may have an open surface 1222, a bottom surface 1224, and a side surface 1226.

When the groove 1220' is viewed in the direction of the inner surface 1204, the open surface 1222 and the bottom surface 1224 of the groove 1220' may have the same form as main surfaces of the contact-type patch. Here, when the groove 1220' is viewed in the direction of the inner surface 1204, at least one of the open surface 1222 and the bottom surface 1224 of the groove 1220 may have a size less than or equal to the main surfaces of the contact-type patch. When the size of the open surface 1222 or the bottom surface 1224 of the groove 1220' is smaller than that of the main surfaces of the contact-type patch, the storage 1220 may stably store the contact-type patch, as the contact-type patch is contained in the groove in a somewhat compressed state.

A depth of the side surface 1226 of the groove 1220' may be the same or smaller than a thickness of the contact-type patch. When the depth of the side surface 1226 of the groove 1220' is smaller than the thickness of the contact-type patch, a portion of the contact-type patch contained in the groove protrudes from the inner surface of the patch plate 1200, and accordingly, contact between the contact-type patch and the specimen T on the specimen plate 1400 may be further facilitated.

A deviation preventing member configured to prevent deviation of the contact-type patch contained in the groove 1220' may be provided at the groove 1220'.

For example, the deviation preventing member may be implemented as a deviation preventing step that extends from the side surface 1226 touching the open surface 1222 of the groove 1220' toward a central portion of the open surface 1222. The contact-type patch contained in the storage 1220 is locked to the open surface 1222 of the groove by the deviation preventing step and thus is prevented from deviating to the outside.

In another example, the deviation preventing member may be implemented as a deviation preventing protrusion that extends from the side surface 1226 of the groove 1220' toward the central portion of the groove 1220'. Due to being compressed and contained in the storage 1220 by the deviation preventing protrusion, the contact-type patch is stably fixed to the storage 1220, and thus does not deviate to the outside.

In yet another example, when the sidewall 1226 of the groove 1220' is formed to be gradually inclined from the bottom surface to the open surface toward the central portion of the groove 1220', the sidewall 1226 may also perform a function of the deviation preventing member that prevents the contact-type patch contained in the groove 1220' from deviating to the outside, instead of the deviation preventing member.

In addition, a contact guide 1228 that facilitates contact between the contact-type patch contained in the groove and the specimen T on the specimen plate 1400 may be provided at the bottom surface of the groove.

Figure 19:
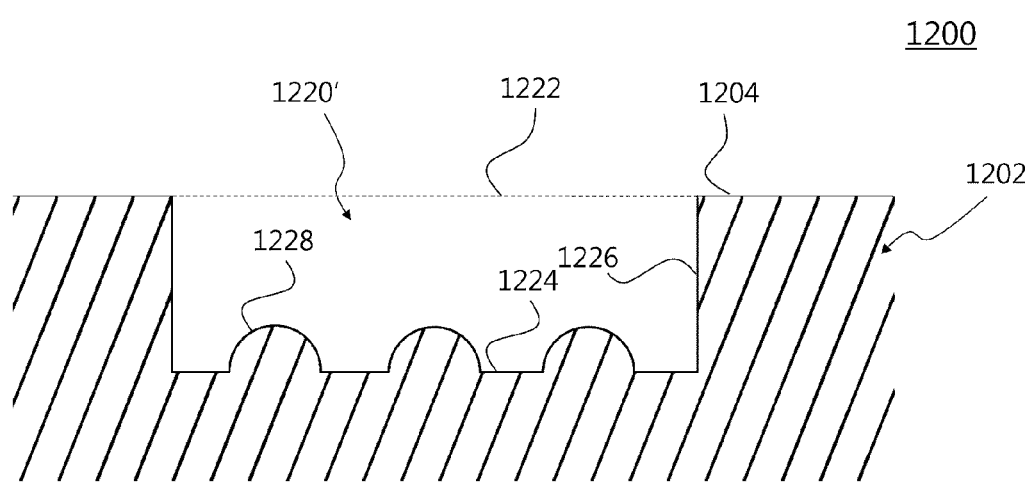
FIGS. 19 and 20 are cross-sectional views of the groove-shaped storage, which has various contact guide means, of the rotating-type test kit according to an embodiment of the present disclosure.
Figure 20:
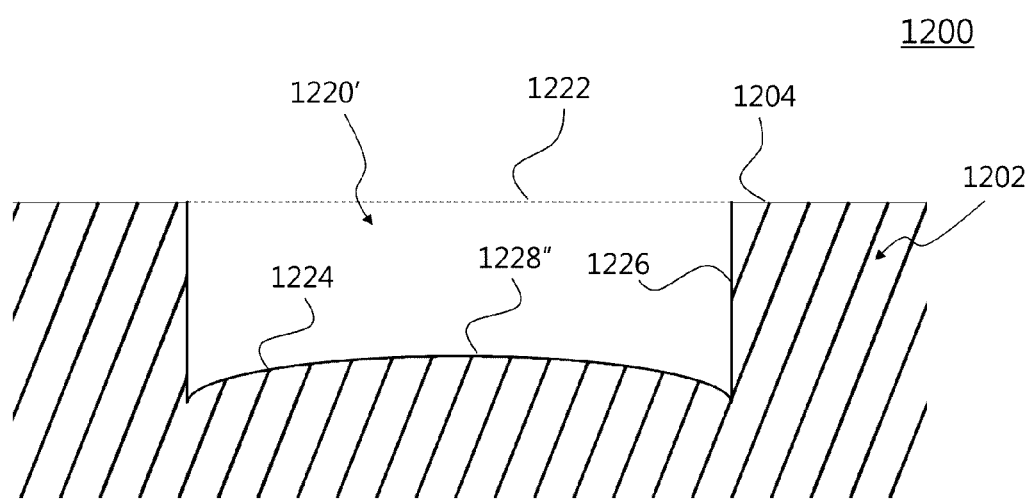

FIGS. 19 and 20 are cross-sectional views of the groove-shaped storage 1220, which has various contact guides 1228, of the rotating-type test kit 1000 according to an embodiment of the present disclosure.

For example, the contact guide 1228 may be implemented as a contact guiding protrusion 1228' that convexly protrudes from the bottom surface 1224 of the groove 1220' illustrated in FIG. 19. A portion of the contact-type patch contained in the storage 1220 protrudes from the inner surface of the patch plate 1200 by the contact guiding protrusion of the bottom surface of the groove, and accordingly, contact with the specimen T on the specimen plate 1400 may be facilitated. The contact guiding protrusion 1228' does not always have to be in the form illustrated in FIG. 19, and, as illustrated in FIG. 20, the bottom surface 1224 of the groove 1220' itself may be formed as a convex surface 1228" and serve as the contact guide 1228.

Although the storage 1220 has been described above as being implemented in the shape of a groove, instead, the storage 1220 may also be in the shape of a hole.

The hole may have a first open surface formed at the inner surface of the patch plate 1200, a second open surface formed at the outer surface, and a side surface. Here, a deviation preventing member for preventing the contact-type patch contained from deviating in a direction of the second open surface may be provided at the second open surface. For example, the deviation preventing member may be implemented as a deviation preventing mesh.

Technical features (e.g., a size of an open surface, a depth of a groove, a deviation preventing step, a deviation preventing protrusion, etc.) mentioned in the description of the storage 1220 in the shape of a groove may also be appropriately applied to the storage 1220 in the shape of a hole. For example, a diameter of the hole may be equal to or less than that of the contact-type patch, a length of the hole may be equal to or less than the thickness of the contact-type patch, or a deviation preventing protrusion may be formed on the side surface of the hole.

3.2.2. Structure of the Specimen Plate

Figure 21:
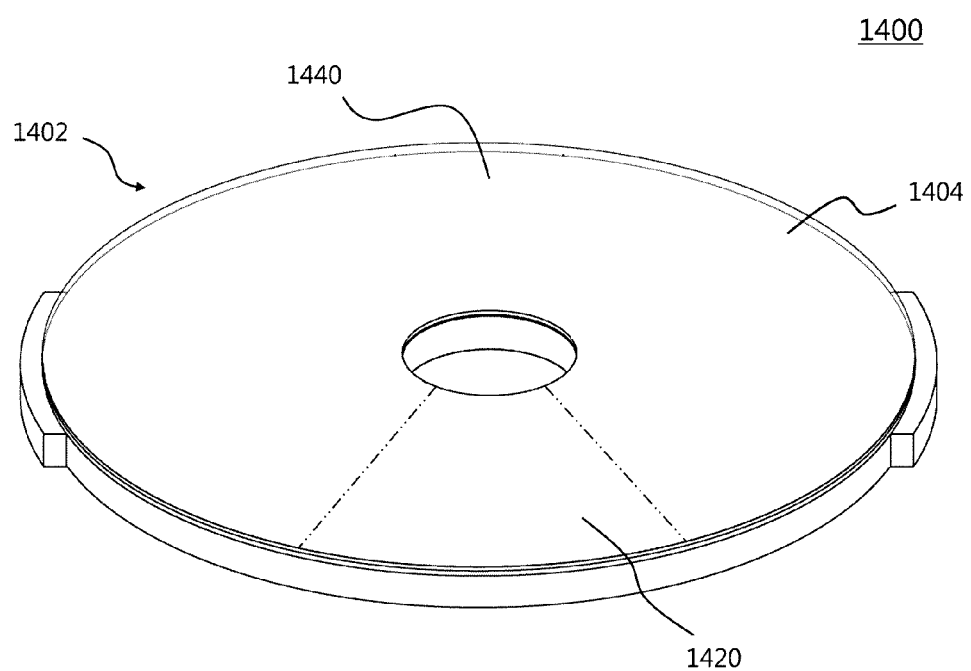
FIG. 21 is a perspective view of an example of a specimen plate of the rotating-type test kit according to an embodiment of the present disclosure.

FIG. 21 is a perspective view of an example of the specimen plate 1400 of the rotating-type test kit 1000 according to an embodiment of the present disclosure. Referring to FIG. 21, as described above, the specimen plate 1400 may have the disc-shaped body 1402 having the inner surface 1404, the outer surface, and the side surface. The inner surface 1404 is a surface facing the patch plate 1200 and may be provided in a circular shape in this embodiment.

A specimen region 1420 may be provided at a circular inner surface of the specimen plate 1400. Here, the specimen region 1420 is a region in which the specimen T inserted (injected) into the test kit 1000 is placed. Although the specimen region 1420 may simply be a region into which the specimen T is placed, the specimen region 1420 should be viewed as a region that even includes a region in which the specimen T is smeared when the specimen T is smeared as in a blood smear examination. For example, when attempting to perform a blood smear examination, blood may be injected in a form of drops into the specimen region 1420 and then smeared.

The specimen region 1420 may be provided in a specific region of an inner surface of a body of the specimen plate 1400. For example, the specimen region 1420 could be located in a predetermined angular range of the inner surface with respect to the center of the disc.

As will be described below, the specimen T placed in the specimen region 1420 has to come into contact with the contact-type patch stored in the patch plate 1200 and has to be observed through an observation hole. For this, the specimen region 1420 needs to be aligned with each portion (the storage 1220, the observation hole, etc.) of the patch plate 1200 as the patch plate 1200 rotates relative to the specimen plate 1400.

In addition, in consideration of a case in which a blood smear examination is conducted using the test kit 1000, the specimen region 1420 needs to provide a region sufficient for injected blood to be smeared.

In consideration of these points, as illustrated in FIG. 21, the specimen region 1420 may be preferably provided in as an angular region of approximately 45 to 90° of the inner surface. The region may be adjusted in consideration of the number of contact-type patches stored in the patch plate 1200, whether blood smear is performed, etc.

When a specimen is dropped onto the specimen region 1420, the specimen T may be directly dropped onto the specimen region 1420. Here, an incised portion of the patch plate 1200 may be aligned at the specimen region 1420 so that the specimen region 1420 is exposed to the outside. For this, an angle range of the specimen region 1420 and an angle range of the incised portion of the patch plate 1200 may be adjusted to be equal to each other.

In addition, a surface of the specimen region 1420 may be specially treated. For example, the surface of the specimen region 1420 may be hydrophilic or hydrophobic. Specifically, the surface of the specimen region 1420 may be coated to be hydrophilic or hydrophobic, or a portion of the specimen region 1420 of the specimen plate 1400 may be prepared with a hydrophobic or hydrophilic material.

The specimen region 1420 is made to exhibit hydrophilia or hydrophobia in order to 1) allow the specimen region 1420 to hold the specimen T and/or 2) allow the specimen region 1420 to receive the staining reagent 140, the buffering solution B, etc. from the contact-type patch. For example, when attempting to perform a blood smear examination using the Giemsa staining technique, the specimen region 1420 may be provided to be hydrophilic to hold blood and receive the Giemsa staining reagent 140 from the contact-type staining patch 100.

A remaining region of the inner surface of the specimen plate 1400 except the specimen region 1420 may be a non-specimen region 1440. The non-specimen region 1440 may be a region in which the specimen T is not expected to be placed or smeared.

A surface of the non-specimen region 1440 may be treated to exhibit a property opposite from that of the surface of the specimen region 1420. For example, the non-specimen region 1440 may be hydrophobic when the specimen region 1420 is hydrophilic, and conversely, the non-specimen region 1440 may be hydrophilic when the specimen region 1420 is hydrophobic.

The non-specimen region 1440 is made to exhibit hydrophilia or hydrophobia in order to 1) inhibit the specimen T from being transferred to the non-specimen region 1440 and/or 2) prevent the staining reagent 140, the buffering solution B, etc. from being transferred from the contact-type patch. Particularly, in a process in which the patch plate 1200 is rotated relative to the specimen plate 1400 to bring the contact-type patch into contact with the specimen T (even when a step exists between the specimen region 1420 and the non-specimen region 1440), the contact-type patch may sweep and pass across the non-specimen region 1440 of the specimen plate 1400. In this process, the staining reagent 140 or the buffering solution B may be unnecessarily wasted by being transferred to the non-specimen region 1440 from the contact-type patch, or the contact-type patch may be contaminated due to a foreign substance on the non-specimen region 1440, and thus the non-specimen region 1440 is treated to be hydrophilic or hydrophobic to prevent the above situations. For example, when attempting to perform a blood smear examination using the Giemsa staining technique, the non-specimen region 1440 may be provided to be hydrophobic so that blood dropped onto the specimen region 1420 is not transferred thereto and/or the Giemsa staining reagent 140 is not transferred thereto from the contact-type staining patch 100.

Figure 22:
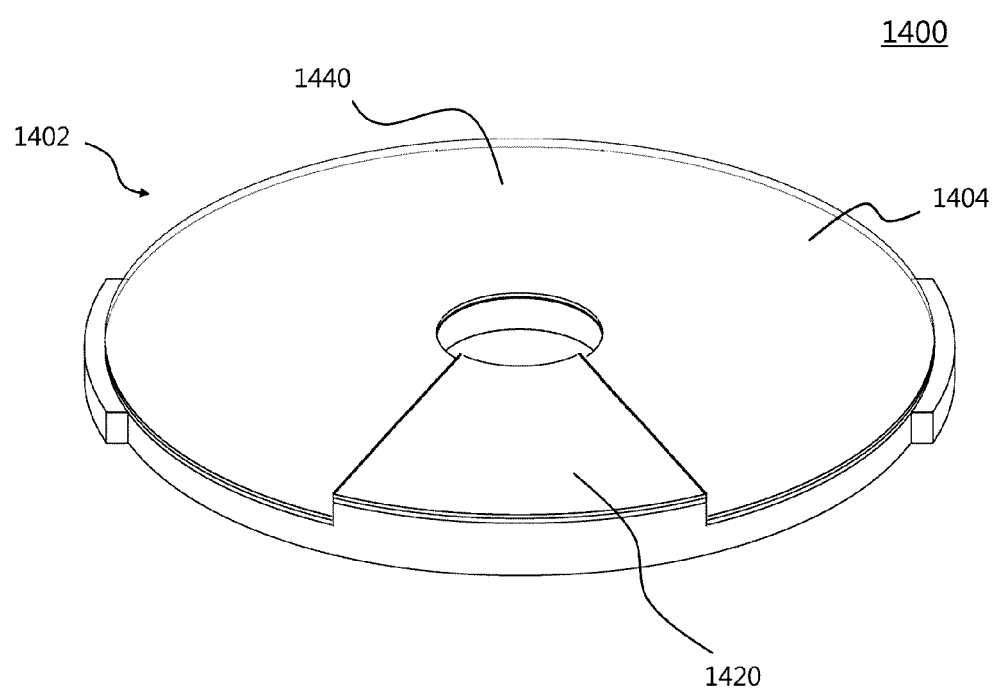
FIG. 22 is a perspective view of an example of a rotating-type specimen plate with a step between a specimen region and a non-specimen region according to an embodiment of the present disclosure.

FIG. 22 is a perspective view of an example of the specimen plate 1400 with a step between the specimen region 1420 and the non-specimen region 1440 of the rotating-type test kit 1000 according to an embodiment of the present disclosure.

Referring to FIG. 22, the non-specimen region 1440 may have a lower height than that of the specimen region 1420. For example, a step may be formed at a boundary between the specimen region 1420 and the non-specimen region 1440. Thus, a distance between the inner surface of the patch plate 1200 and the inner surface of the specimen plate 1400 corresponding to the non-specimen region 1440 may be larger than a distance between the inner surface of the patch plate 1200 and the inner surface of the specimen plate 1400 corresponding to the specimen region 1420.

During a process in which the specimen T and the contact-type patch are brought into contact with each other, the patch plate 1200 is rotated relative to the specimen plate 1400 so that the contact-type patch can be aligned with the specimen region 1420. When there is a step between the specimen region 1420 and the non-specimen region 1440, the contact-type patch may be prevented from sweeping and passing across the non-specimen region 1440 of the specimen plate 1400 during the rotation of the patch plate 1200 while the contact between the contact-type patch and the specimen T on the specimen region 1420 is easily maintained. Accordingly, the staining reagent 140 or the buffering solution B of the contact-type patch may be prevented from being wasted due to being transferred to the non-specimen region 1440 and contamination of the contact-type patch due to contact with the non-specimen region 1440 may be inhibited.

3.2.3 Smearing Unit

The test kit 1000 may further include a smearing unit 1240 configured to smear the specimen T dropped onto the specimen region 1420. Hereinafter, the smearing unit 1240 that smears the specimen will be described.

In a conventional staining technique, smearing of the specimen T is performed manually by an operator.

Figure 23:
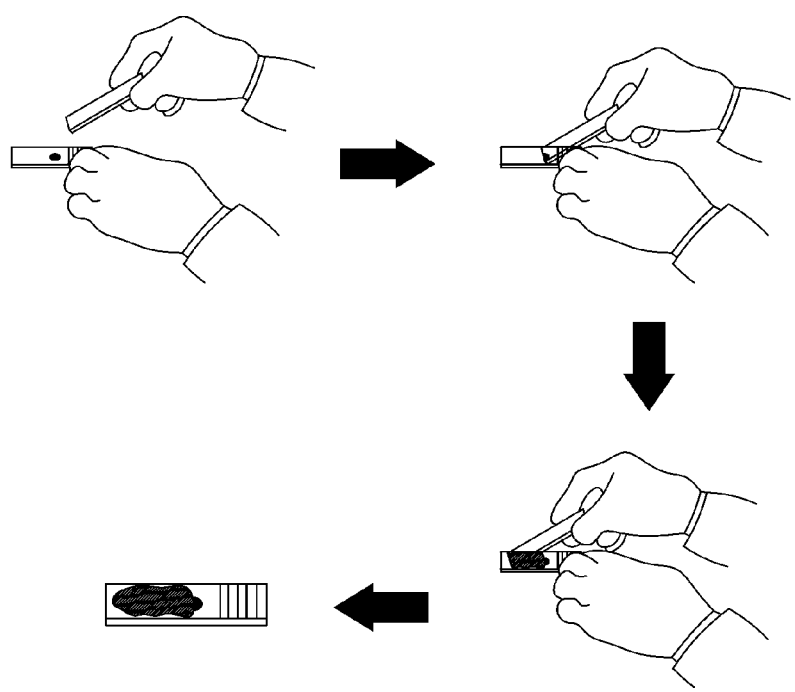
FIG. 23 is a view illustrating a blood smearing means according to the conventional blood smear examination process.

FIG. 23 is a view illustrating a blood smearing means according to the conventional blood smear examination process.

Referring to FIG. 23, in the conventional blood smear examination process, the specimen T is first placed on the slide S and then another slide is brought into contact with the slide S on which the specimen T is placed so that an acute angle is formed therebetween. Then, when an operator slides the slide S on which the specimen T is placed while an end of the other slide remains in contact with the specimen T, the specimen T may be spread on the slide S and smeared. The angle between the slides and a sliding speed need to be properly adjusted to smear the specimen T in a desired form (e.g., a monolayer). Conventionally, there is a problem of low stability due to the above factors totally depending on the operator.

Figure 24:
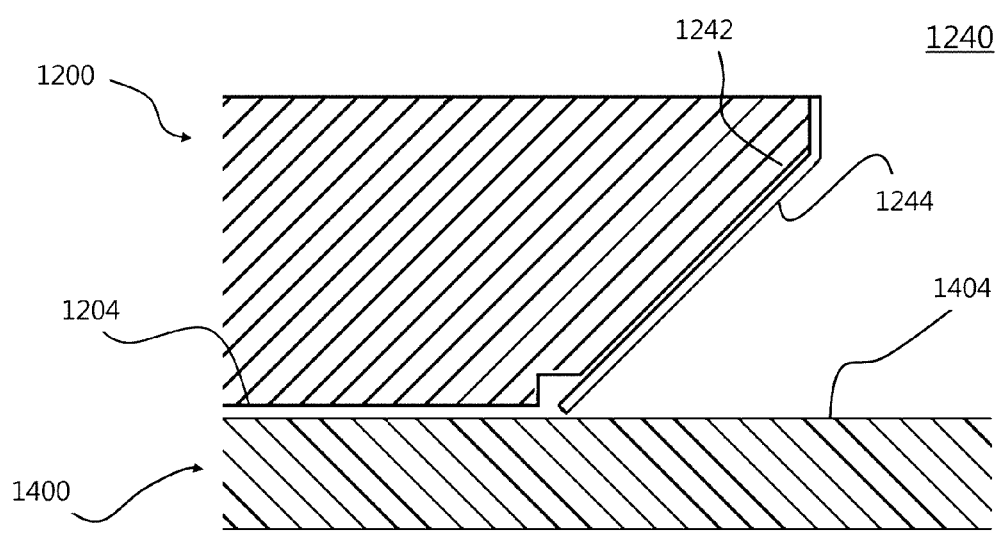
FIG. 24 is a cross-sectional view of a smearing unit of the rotating-type test kit according to an embodiment of the present disclosure.

FIG. 24 is a cross-sectional view of the smearing unit 1240 of the rotating-type test kit 1000 according to an embodiment of the present disclosure.

Referring to FIG. 24 in addition to FIGS. 15 to 17, the smearing unit 1240 may be provided at any one side of the incised portion of the patch plate 1200. The smearing unit 1240 may perform a function of smearing the specimen T placed on the specimen region 1420.

The smearing unit 1240 may include an inclined surface 1242 that forms an acute angle with the inner surface of the specimen plate 1400 that faces the inclined surface 1242 when viewed from the side and a smearing film 1244 attached to the inclined surface 1242.

Hereinafter, a specimen smearing process using the smearing unit 1240 will be briefly described. However, for convenience of description, the description will be given based on a blood smear.

Figure 25:
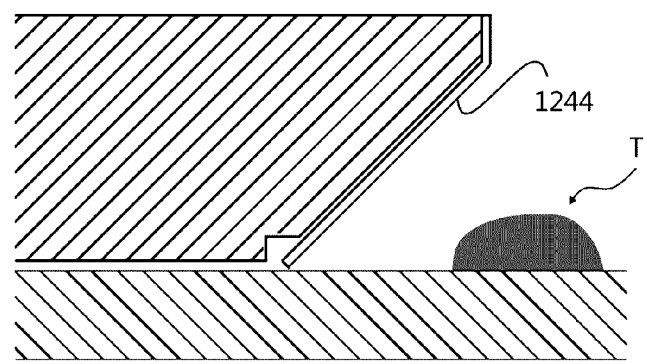
FIG. 25 is a view illustrating a blood smearing process using the smearing unit of the rotating-type test kit according to an embodiment of the present disclosure.
Figure 25:
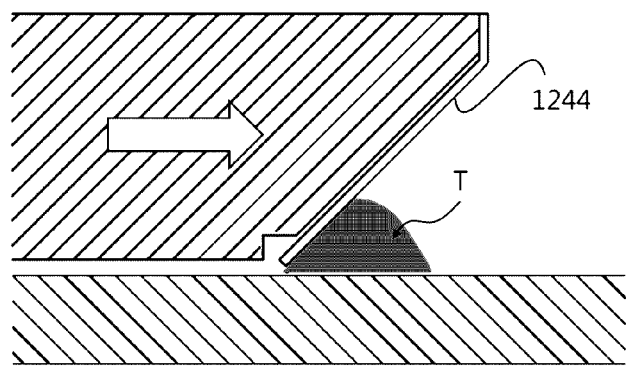
Figure 25:
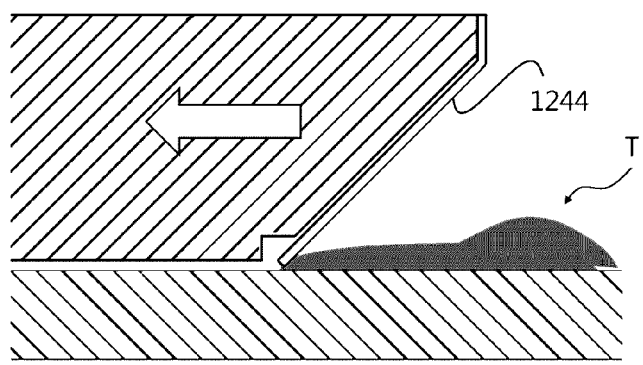

FIG. 25 is a view illustrating a blood smearing process using the smearing unit 1240 of the rotating-type test kit 1000 according to the embodiment of the present disclosure.

First, as in (a) of FIG. 25, blood is dropped onto the specimen region 1420 of the specimen plate 1400. Here, the incised portion of the patch plate 1200 and the specimen region 1420 of the specimen plate 1400 are aligned with each other so that the specimen region 1420 is exposed to the outside.

When the blood is injected, as in (b) of FIG. 25, the patch plate 1200 is rotated with respect to the specimen plate 1400 (the direction of this rotation is defined as a "reverse direction") so that the smearing unit 1240 is moved toward a point into which blood is injected. As a result, the smearing film 1244 and a blood drop placed on the specimen region 1420 come into contact with each other.

When the smearing film 1244 and the blood come into contact with each other, due to the capillary action, the blood spreads between the smearing film 1244 and the surface of the specimen region 1420 along the smearing film 1244 in a direction in which the patch plate 1200 is incised. When the patch plate 1200 is a sector-shaped plate in which a disc is incised in the radial direction, the blood spreads in the radial direction.

When the patch plate 1200 is rotated in a forward direction (opposite the reverse direction) with respect to the specimen plate 1400 while the blood is spread, the blood may move along the smearing film 1244 and be smeared as illustrated in (c) of FIG. 25.

Here, the inclined surface of the smearing unit 1240 may preferably have an angle of inclination of approximately 10 to 60° with respect to the inner surface of the specimen plate 1400. The size of the angle of inclination may be properly adjusted according to a property of the specimen T.

When the angle of inclination is too large (e.g., a right angle), it may be difficult for the capillary action to occur in a step in which the smearing film 1244 and the specimen T come into contact with each other (the step illustrated in (b) of FIG. 25), and the specimen T may not sufficiently spread in the direction in which the patch plate 1200 is incised. In addition, even when attempting to smear the specimen T by a forward rotation, smearing may not be properly performed due to the blood not following the smearing film 1244.

On the other hand, when the angle of inclination is too small, the capillary action may not properly occur due to the smearing film 1244 and the specimen T coming into contact with each other at a portion other than a lower end portion of the smearing film 1244, and smearing may not be performed due to the blood not properly following the smearing film 1244.

A material that can be easily followed by the specimen T may be used for the smearing film 1244. For example, when the specimen T is blood, a hydrophilic material should be used for the smearing film 1244 so that the blood is smeared by following the smearing film 1244 during the forward rotation of the patch plate 1200. When a hydrophobic smearing film 1244 is used for the specimen T which is blood, smearing may not be performed.

When viewed from the top, the smearing film 1244 may be attached and installed along the direction in which the patch plate 1200 is incised. When viewed from the top, the smearing film 1244 should have a length of an extent to which the specimen T can sufficiently spread according to the capillary action in the direction in which the patch plate 1200 is incised. For example, the smearing film 1244 may have a length of about 30 to 100% of an incised surface in the diameter direction.

When viewed from the side, the smearing film 1244 may be attached and installed at the inclined surface along the angle of inclination thereof. Here, the smearing film 1244 is installed so it can touch the inner surface of the specimen plate 1400. Accordingly, the smearing film 1244 may cause the capillary action at the specimen T.

Although it would be theoretically preferable that the lower end of the smearing film 1244 be manufactured to accurately come into contact with the inner surface of the specimen plate 1400, this is actually impossible or costs high in consideration of manufacture tolerance and the like.

Consequently, for the smearing film 1244 to come into contact with the specimen region 1420, the smearing film 1244 may be installed in a way in which a lower portion thereof protrudes from the inner surface of the patch plate 1200 in the direction of the inner surface of the specimen plate 1400. According to this, since the smearing film 1244 has some degree of flexibility, the smearing film 1244 may come into contact with the specimen region 1420 because the lower portion of the smearing film 1244 is curled in a bent form. In addition to this, a groove may be formed at a lower portion of the inclined surface for a space in which a curled portion of the smearing film 1244 is accommodated.

Although it has been described above that the operator directly drops the specimen T on the specimen region 1420 when the specimen T is being injected, instead, a loading unit 1250 through which the specimen T is inserted may also be provided.

Figure 26:
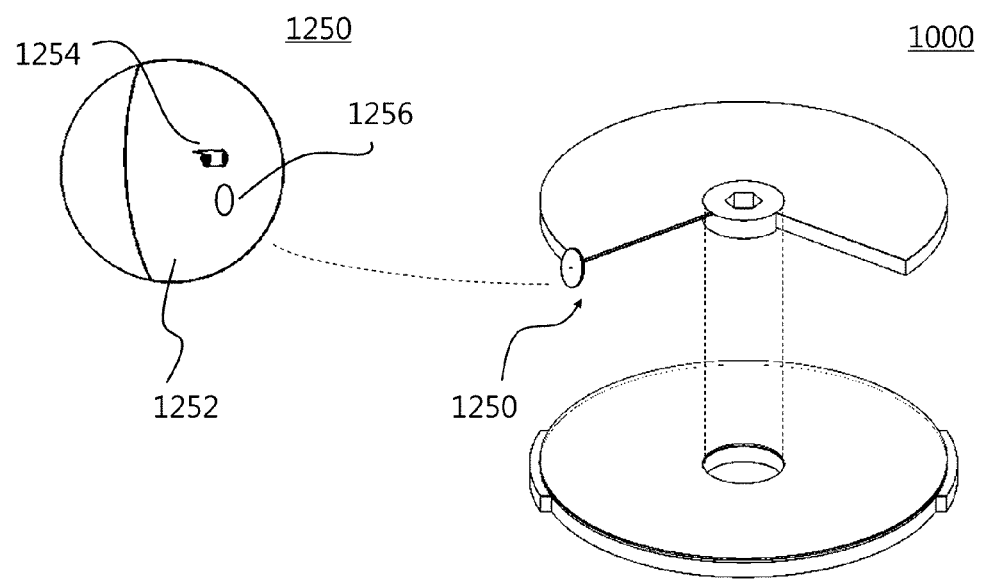
FIG. 26 is a view illustrating a loading unit of the rotating-type test kit according to an embodiment of the present disclosure.
Figure 27:
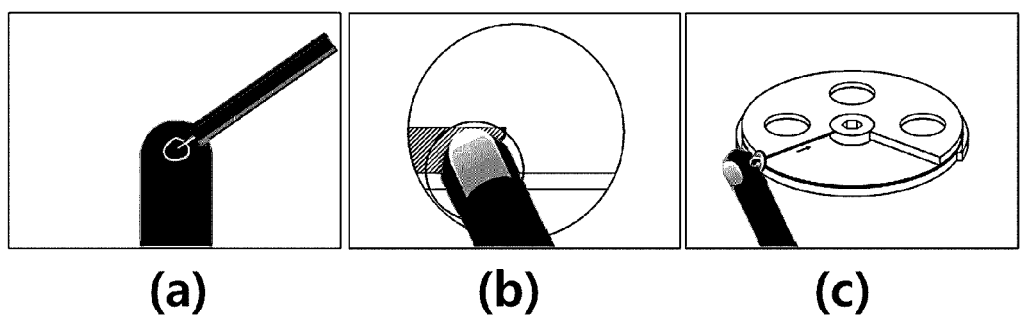
FIG. 27 is a view related to loading of a specimen using the loading unit of the rotating-type test kit according to an embodiment of the present disclosure.

FIG. 26 is a view illustrating the loading unit 1250 of the rotating-type test kit 1000 according to an embodiment of the present disclosure, and FIG. 27 is a view related to loading of the specimen T using the loading unit 1250 of the rotating-type test kit 1000 according to an embodiment of the present disclosure.

Referring to FIG. 26, the loading unit 1250 may include a pressing plate 1252, a collecting pin 1254, and a loading hole 1256.

The pressing plate 1252 is a portion pressed by a testee's body part from which the specimen T will be collected. For example, when attempting to collect blood from a person's fingertip, the pressing plate 1252 may be provided in the shape of a plate having a proper size to be pressed by the person's fingertip. The pressing plate 1252 may be installed at a position which enables the collected specimen T to be transferred to the specimen region 1420 of the specimen plate 1400. For example, the pressing plate 1252 may be disposed at an outer edge portion of the incised surface of the patch plate 1200 or an outer edge portion of the specimen region 1420.

The collecting pin 1254 is a pin installed to protrude from the pressing plate 1252. During a process in which the testee's body part presses the pressing plate 1252, the collecting pin 1254 pierces skin at the body part to allow the specimen T to be collected from the testee. The collecting pin 1254 may preferably be disposed at a central portion of the pressing plate 1252 and be installed toward an outer direction of the test kit 1000.

The loading hole 1256 is formed in the form of a hole that passes through the pressing plate 1252 and may be formed by passing from an outer surface (a surface coming into contact with the testee's body part) to the opposite surface of the pressing plate 1252. Accordingly, the loading hole 1256 may load the specimen T from an outside of the pressing plate 1252 to an inside of the test kit 1000, more specifically, toward the specimen region 1420 or the smearing unit 1240 of the specimen plate 1400. The loading hole 1256 may be formed near the collecting pin 1254 and receive the specimen T collected from the testee's skin by the collecting pin 1254, and may transfer and insert the specimen T toward the specimen region 1420 or the smearing unit 1240 according to the capillary action.

The loading of the specimen T may be performed as follows.

First, when a testee presses the pressing plate 1252 with a finger as illustrated in (b) of FIG. 27, blood comes out of skin of the finger by the collecting pin 1254. As illustrated in (c) of FIG. 27, the blood is transferred through the loading hole 1256 to the outside of the specimen region 1420 that comes into contact with the smearing film 1244. The transferred blood is transferred to the inside of the specimen region 1420 by the capillary action between the smearing film 1244 and the specimen region 1420. Then, the patch plate 1200 may be rotated in the forward direction with respect to the specimen plate 1400 to smear the blood.

When the loading unit 1250 is used in this way, the specimen T may be inserted into the test kit 1000 by only simply pressing the loading unit with a testee's body part instead of an operator directly injecting the specimen T into the specimen region 1420.

The collecting pin 1254 may be omitted from the pressing plate 1252 in the above-described process of loading the specimen T. In this case, as in (a) of FIG. 27, before the pressing plate 1252 is pressed using the testee's body part, a separate pin may be used to allow the specimen T to be collected from the corresponding body part.

3.2.4. Rotating and Lifting Operations of the Test Kit

It has been mentioned above that the process of staining the specimen T can be carried out by bringing the contact-type patch into contact with the specimen T applied onto the specimen plate 1400 while the patch plate 1200 rotates relative to the specimen plate 1400.

Specifically, a process of bringing the contact-type patch and the specimen T into contact with each other may be carried out by 1) rotating the patch plate 1200 relative to the specimen plate 1400 to place the contact-type patch on the specimen T or the specimen T which is smeared; and 2) lowering patch plate 1200 relative to the specimen plate 1400 so that the contact-type patch stored in the patch plate 1200 comes into contact with the specimen T.

The patch plate 1200 and the specimen plate 1400 are basically coupled in a way in which the inner surfaces thereof are spaced apart from each other in a predetermined interval. This is to prevent the contact-type patch stored in the patch plate 1200 from being swept by the specimen plate 1400 during a rotation process. Consequently, after the contact-type patch is placed on the specimen T, the patch plate 1200 and the specimen plate 1400 should be adhered to each other to bring the contact-type patch into contact with the specimen T.

For this, lifting guides 1260 and 1460 may be formed at the patch plate 1200 and/or the specimen plate 1400. The lifting guides 1260 and 1460 may allow the lifting of the patch plate 1200 and the specimen plate 1400 according to relative rotations of the patch plate 1200 and the specimen plate 1400.

Figure 28:
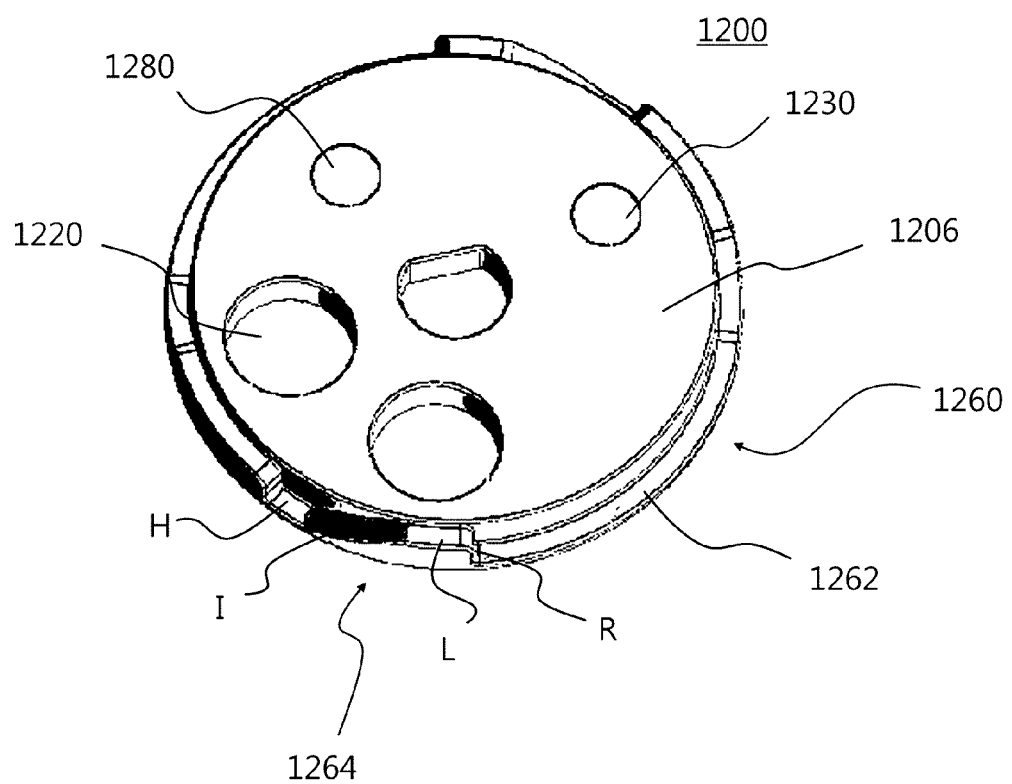
FIG. 28 is a perspective view of a patch plate having a lifting guide of the rotating-type test kit according to an embodiment of the present disclosure.
Figure 29:
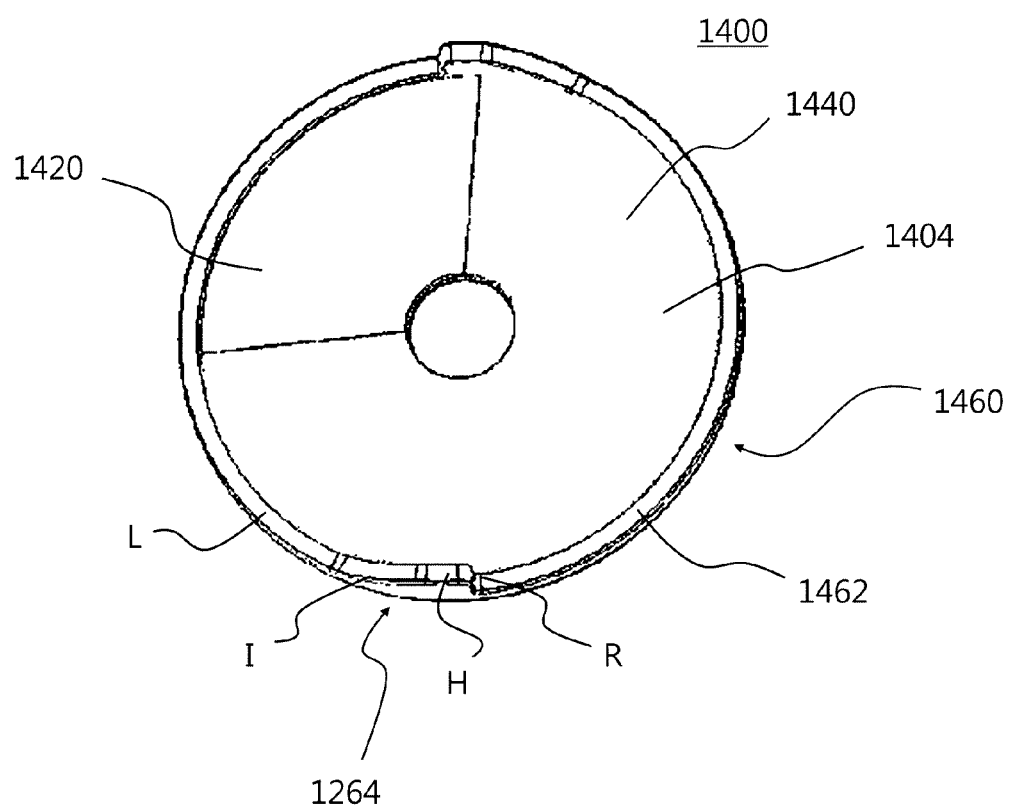
FIG. 29 is a perspective view of a specimen plate having a lifting guide of the rotating-type test kit according to an embodiment of the present disclosure.

FIG. 28 is a perspective view of the patch plate 1200 having the lifting guides 1260 of the rotating-type test kit 1000 according to an embodiment of the present disclosure, and FIG. 29 is a perspective view of the specimen plate 1400 having the lifting guides 1260 of the rotating-type test kit 1000 according to an embodiment of the present disclosure.

Referring to FIGS. 28 and 29, the lifting guides 1260 and 1460 may be formed at outsides of the bodies of the patch plate 1200 and the specimen plate 1400. The lifting guides 1260 and 1460 formed at the two plates may respectively include base plates 1262 and 1462 formed to surround circumferences of the bodies and lifting patterns 1264 and 1464 formed in predetermined patterns on the base plates 1262 and 1462.

The base plates 1262 and 1462 are formed to surround outer circumferential surfaces of the bodies of the patch plate 1200 and the specimen plate 1400 with smaller thicknesses than the bodies of the patch plate 1200 and the specimen plate 1400. In other words, the base plates 1262 and 1462 are bent with steps from circumferences of the inner surfaces of the patch plate 1200 and the specimen plate 1400 toward the outer surfaces thereof to form edges of the patch plate 1200 and the specimen plate 1400.

In FIG. 28, a disc-shaped body may be used instead of the incised sector-shaped body for the patch plate 1200. In this case, the specimen T may be inserted by being transferred to the specimen plate 1400 through a specimen insertion hole 1230 instead of being dropped through the incised portion. In addition, although it has been described that the coupling protrusion is formed at the patch plate 1200, a coupling hole instead of the coupling protrusion may be formed in FIG. 28. The coupling hole communicates with a coupling hole at the specimen plate 1400, and the two plates may be coupled to each other by a coupling pin fitted into a communication passage. Here, it should be noted that both of the sector-shaped form and the disc-shaped body according to FIG. 28 are modified examples not departing from the spirit of the present disclosure.

The lifting patterns 1264 and 1464 may be formed protruding or being recessed from the base plates. The lifting patterns 1264 and 1464 may perform roles of adjusting an interval between the inner surfaces of the two plates according to relative angle between the two plates while the two plates are coupled to each other.

The lifting patterns 1264 and 1464 may each include a high point part H, a low point part L, a sloped part I, and a stepped part R. Here, the high point part H is the highest part of the lifting patterns 1264 and 1464, and the low point part L is the lowest part of the lifting patterns. For example, the high point part H may be a part that protrudes the most from the base plates, and the low point part L may be a part that does not protrude from the base plates. The sloped part I may be a part with a slope that gradually increases from the low point part toward the high point part. The stepped part R may be a part perpendicularly bent from the high point part H toward the low point part L.

When the patch plate 1200 rotates with respect to the specimen plate 1400, the patch plate 1200 may be lifted with respect to the specimen plate 1400 as the lifting pattern of the patch plate 1200 moves along an upper portion of the lifting pattern of the specimen plate 1400. Here, lifting refers to an interval between the two plates being narrowed or widened. The patch plate 1200 moving away from the specimen plate 1400 is defined as "ascending," and the patch plate 1200 approaching the specimen plate 1400 is defined as "descending."

A state in which the high point part of the specimen plate 1400 is aligned with the low point part of the other plate is a state in which the patch plate 1200 is maximally descended with respect to the specimen plate 1400, i.e. a state in which the interval between the two plates is minimal.

A state in which the high point part of the specimen plate 1400 is aligned with the high point part of the patch plate 1200 is a state in which the patch plate 1200 is maximally ascended with respect to the specimen plate 1400, i.e. a state in which the interval between the two plates is maximal.

In addition, while the high point part of the specimen plate 1400 moves from the low point part of the patch plate 1200 toward the high point part of the patch plate 1200 along the sloped part of the patch plate 1200, the patch plate 1200 gradually ascends with respect to the specimen plate 1400. Conversely, while the high point part of the specimen plate 1400 moves from the high point part of the patch plate 1200 toward the low point part of the patch plate 1200 along the sloped part of the patch plate 1200, the patch plate 1200 gradually descends with respect to the specimen plate 1400.

In addition, when the high point part of the specimen plate 1400 passes the stepped part of the patch plate 1200 in a direction from the high point part of the patch plate 1200 toward the low point part of the patch plate 1200, the patch plate 1200 perpendicularly descends with respect to the specimen plate 1400.

Conversely, when the stepped part is formed at the patch plate 1200 and the high point part of the specimen plate 1400 attempts to move in a direction from the low point part of the patch plate 1200 toward the high point part of the patch plate 1200, a rotation of the patch plate 1200 relative to the specimen plate 1400 may be inhibited by the stepped part.

The test kit 1000 may be designed in a way in which the contact-type patch stored in the patch plate 1200 comes into contact with at least a portion of the inner surface of the specimen plate 1400 when the patch plate 1200 is maximally descended with respect to the specimen plate 1400, and hereinafter, this is defined as a "contact state." For example, in the contact state, the contact-type patch contained in the storage 1220 may come into contact with the specimen T placed in the specimen region 1420.

In addition, the test kit 1000 may be designed in a way in which the contact-type patch stored in the patch plate 1200 does not come into contact with the inner surface of the specimen plate 1400 at states other than that in which the patch plate 1200 is maximally descended with respect to the specimen plate 1400, and hereinafter, this is defined as a "separated state". For example, in the separated state, the contact-type patch contained in the storage 1220 may not come into contact with the non-specimen region 1440.

In consideration of the principles above, the lifting patterns may be designed as follows.

The lifting patterns may be designed so that the contact-type patch is in contact state when at an angle at which the storage 1220 of the patch plate 1200 is aligned with the specimen region 1420 of the specimen plate 1400. Accordingly, the contact-type patch contained in the storage 1220 may come into contact with the specimen T.

In addition, the lifting patterns may be designed so that the contact-type patch is not in contact state when an angle at which the storage 1220 of the patch plate 1200 is located above the non-specimen region 1440 of the specimen plate 1400. Accordingly, the contact-type patch contained in the storage 1220 may not come into contact with the non-specimen region 1440.

Referring again to FIG. 29, the lifting pattern of the specimen plate 1400 may be formed as follows.

The high point part is disposed at one or more portions of the edge of the specimen region 1420. Here, the portion may be the edge portion of the specimen region 1420 at which the specimen is placed, or may be the edge portion at a central point of a region in which the specimen T is smeared when the specimen T is smeared. The lifting pattern may be formed so that the low point part is disposed at the edge portion of the non-specimen region 1440. The sloped part or the stepped part may be disposed between the high point part and the low point part.

Referring again to FIG. 28, the lifting pattern of the patch plate 1200 may be formed as follows. FIG. 28 illustrates the patch plate 1200 in an outer surface direction.

The low point part is disposed at a portion of an edge of the storage 1220. Here, the portion may be an edge in the diameter direction from the center of the patch plate 1200 toward the center of the storage 1220. The high point part is disposed at remaining parts of the edge of the patch plate 1200. The sloped part or the stepped part may be disposed between the high point part and the low point part.

According to the lifting patterns, the test kit 1000 may operate as follows. First, the incised portion of the patch plate 1200 may be disposed at an upper portion of the specimen region 1420 of the specimen plate 1400 such that the specimen region 1420 is exposed to the outside. An operator may directly drop the specimen T onto the exposed specimen region 1420. When the specimen T is dropped, the patch plate 1200 is rotated in the reverse direction with respect to the specimen plate 1400 to bring the smearing unit 1240 into contact with the specimen T so that the specimen T is spread along the smearing unit 1240. When the specimen T is spread, the patch plate 1200 may be rotated in the forward direction to smear the specimen T. During this process, the high point part of the specimen plate 1400 is in contact with the high point part of the patch plate 1200, and accordingly, the storage 1220 is not in contact with the inner surface (the non-specimen region 1440) of the specimen plate 1400.

When the patch plate 1200 is further rotated in the forward direction after the smearing is completed, the high point part of the specimen plate 1400 comes into contact with the low point part of the patch plate 1200 disposed at the edge of the storage 1220, and accordingly, the two plates are in the contact state and the contact-type patch contained in the storage 1220 comes into contact with the specimen T at the specimen region 1420.

Here, the stepped part may be provided between the high point part at the edge of the smearing unit 1240 and the low point part of the storage 1220. Accordingly, while passing through the stepped part, the patch plate 1200 perpendicularly descends with respect to the specimen plate 1400, and thus the contact-type patch may come into contact with the specimen T by being stamped thereon. In addition, after the stamping of the contact-type patch, a reverse rotation of the patch plate 1200 may be inhibited by the stepped part.

When the patch plate 1200 is further rotated in the forward direction after the stamping, the high point part of the specimen plate 1400 passes the sloped part of the patch plate 1200. Accordingly, the contact-type patch is separated from the specimen T as the patch plate 1200 ascends from the specimen plate 1400.

The high point part of the specimen plate 1400 comes into contact with the high point part of the patch plate 1200 again after passing the sloped part of the patch plate 1200, and the separation is completed. Accordingly, when the contact-type patch stored in the patch plate 1200 passes an upper portion of the non-specimen region 1440, the contact-type patch may not come into contact with the inner surface of the specimen plate 1400.

When there are one or more storages 1220, the patch plate 1200 may be further rotated in the forward direction. Here, the high point part of the specimen plate 1400 comes into contact with the low point part of the patch plate 1200 corresponding to the next storage 1220, and thus the next contact-type patch comes into contact with the specimen T. This process may be similarly followed by the stamping process and the process in which the contact-type patch is separated from the specimen T by the sloped part described above.

When the patch plate 1200 is further rotated in the forward direction after the specimen T is brought into contact with all contact-type patches provided in the test kit 1000, the high point part of the specimen plate 1400 comes into contact with the low point part formed at an edge of an observation portion of the patch plate 1200.

Here, the observation portion may be formed with an observation hole formed at one point of the patch plate 1200, and the operator may observe and examine the specimen T which is completely stained, and the like, using a microscope, or the like.

3.3. Structure of Sliding-Type Test Kit

Hereinafter, the sliding type test kit 2000 will be described.

However, in the description below, detailed description of technical details common to both the sliding type test kit 2000 and the rotating-type test kit 1000 will be omitted as necessary.

However, the omission of detailed description does not mean that the technical details described with respect to the rotating-type kit 1000 are not applied to the sliding type kit 2000. In other words, it should be noted that, unless indicated otherwise, details of the description on the rotating-type test kit 1000 given above, except for differences generated due to the rotating-type and the sliding type, are applicable to the sliding type test kit 2000.

For example, the sliding type test kit 2000 may also include a specimen region 2420 that corresponds to the specimen region 1420 of the rotating-type test kit 1000. Here, like the specimen region 1420 of the rotating-type test kit 1000 described above, a surface of the specimen region 2420 may be treated to be hydrophilic or hydrophobic. In another example, the sliding type test kit may also include a smearing unit. Here, as in the example described above with respect to the rotating-type test kit, the smearing unit may also have an angle of inclination of approximately 10 to 60°.

FIG. 30 is a side view of an example of the sliding type test kit 2000 according to an embodiment of the present disclosure.

Referring to FIG. 30, in the test kit 2000, a patch plate 2200 and a specimen plate 2400 may respectively have rectangular plate-shaped bodies 2202 and 2402.

The plates 2200 and 2400 are disposed to face each other and may be coupled to be linearly movable, i.e., slidable, relative to each other. Here, a sliding direction may be along a longitudinal direction of the bodies 2202 and 2402. For example, at an outer side of any one of the two plates, a guide protrusion may be formed along the longitudinal direction of the body thereof, and a guide groove having a shape complementary to that of the guide protrusion may be provided in the other plate, so that the two plates 2200 and 2400 are fastened in the form in which the guide protrusion is fitted into the guide groove, and the two plates 2200 and 2400 are slidable relative to each other in accordance with the guide protrusion and the guide groove.

3.3.1. Structure of Patch Plate

Figure 31:
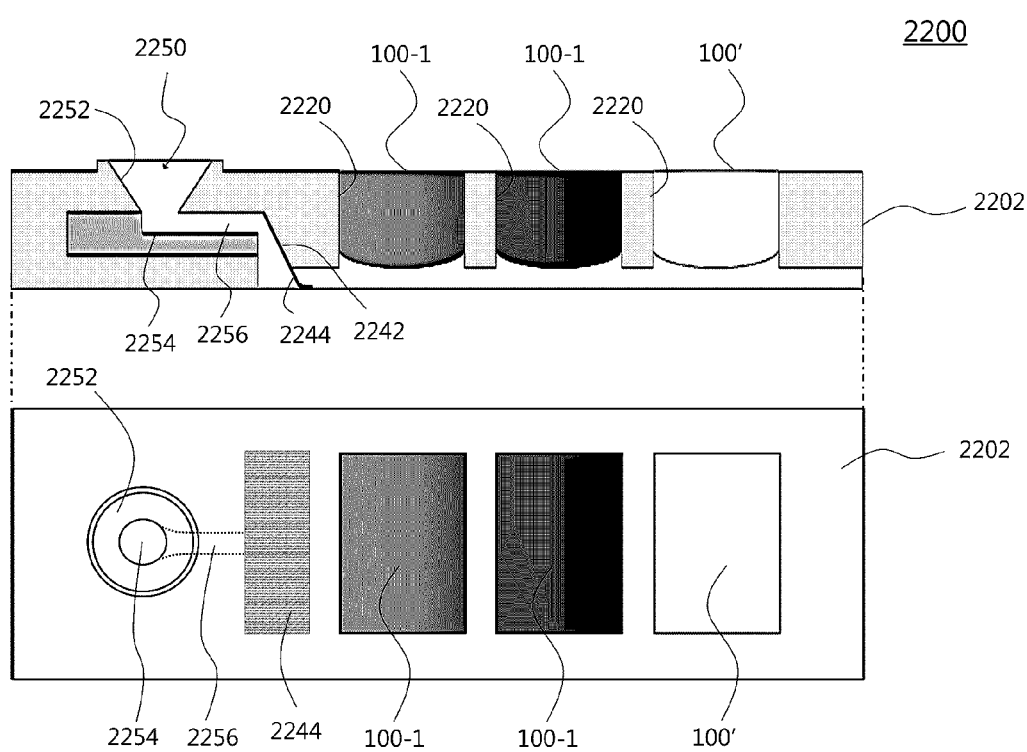
FIG. 31 is a view related to an example of a patch plate of the sliding type test kit according to FIG. 30.

FIG. 31 is a perspective view of an example of a patch plate 2200 of the sliding type test kit 2000 according to an embodiment of the present disclosure.

Referring to FIG. 31, the patch plate 2200 may have a quadrilateral plate-shaped body 2202.

The body 2202 may include a storage 2220 configured to store a contact-type patch such as the contact-type staining patch 100 or the contact-type staining supplementary path 100', a loading unit 2250 into which a specimen T is inserted, and a smearing unit 2240 configured to smear the specimen T.

The loading unit 2250 is formed at one side of the body 2202. The loading unit 2250 may include an inlet 2252 through which a specimen T is inserted, a receiving unit 2254 on which the inserted specimen T is received, and a channel portion 2256 configured to guide the received specimen to the smearing unit 2240.

When the specimen T is dropped through the inlet 2252, the receiving unit 2254 may accommodate the inserted specimen T. The channel portion 2256 is a flow path connected from the receiving unit 2254 to the smearing unit 2240, and may move the specimen T accommodated in the receiving unit 2254 to the smearing unit 2240. Specifically, the channel portion 2256 may use the capillary action and move the specimen T from the receiving unit 2254 to the smearing unit 2240.

Here, although the inlet 2252 and the receiving unit 2254 may be provided in a circular shape, the shape thereof is not limited thereto. The channel portion 2256 may take the form of a linear flow path that extends from the receiving unit 2254, and may be a type of micro channel. However, the shape and type of the channel portion 2256 are not limited thereto.

The smearing unit 2240 may be provided in a shape similar to that of the smearing unit 1240 described with respect to the rotating-type test kit 1000. That is, the smearing unit 2240 may include an inclined surface 1242 that forms an acute angle with the inner surface of the specimen plate 2400 that faces the inclined surface 2242 when viewed from the side and a smearing film 2244 attached to the inclined surface. Here, the smearing film 2244 may be connected to an end of the channel portion 2256 and may be attached to the inclined surface 2242 so that the smearing film 2244 extends in a vertical direction from the channel portion 2256.

Accordingly, when the specimen T inserted into the test kit 2000 comes into contact with the smearing film 2244 through the inlet 2252, the receiving unit 2254, and the channel portion 2256, due to the capillary action, the blood spreads between the smearing film 2244 and the surface of the specimen region 2420 along the smearing film 2244 in a direction in which the smearing film 2244 extends (the vertical direction from the channel portion 2256).

For the material of the film 2244 or the form of the film 2244 in which a lower end thereof is rolled, those described with respect to the rotating-type test kit 1000 may be applied.

A plurality of storages 2220 may be present, and when there are a plurality of storages 2220, the storages 2220 may be disposed in the longitudinal direction of the body 2202. Consequently, in the body 2202, the loading unit 2250 and each storage 2220 may be disposed in a row from one side in the longitudinal direction of the body 2202. Also, the smearing unit 2240 may be disposed between the loading unit 2250 and the storage 2220.

The plurality of storages 2220 may be formed at positions spaced a predetermined distance apart from each other. For reference, FIG. 31 illustrates a patch plate 2200 in which three storages 2220 are formed. Here, although the storages 2220 sequentially store the first staining patch 100-1, the second staining patch 100-2, and the staining supplementary patch 100' in that order, this is merely an example, and the types of contained contact-type patches, and the arrangement and the number thereof may be appropriately changed.

The storage 2220 may contain the contact-type staining patch 100 or the contact-type staining supplementary patch 100' so that the contact-type staining patch 100 or the contact-type staining supplementary patch 100' is exposed in a direction of the inner surface of patch plate 2200. In other words, a contact-type patch may be contained in the storage 2220 so that a contact surface of the contact-type patch faces the specimen plate 2400. Accordingly, the contact-type patch contained in the storage 2220 may come into contact with a specimen T to be dropped onto the specimen plate 2400.

For example, as illustrated in FIG. 31, the storage 2220 may be formed in the form of a hole. In another example, the storage 2220 may also have the form of a groove, and in this case, a bottom surface of the storage 2220 (that is, the outer surface of the patch plate 2200) may be formed with a flexible material so that, when a force is applied from the outer surface of the patch plate 2200 toward the inner surface thereof, at least a portion of the contained contact-type patch moves toward the specimen plate 2400.

The details described with respect to the rotating-type test kit 1000 may also be applied to the storage 2220.

3.3.2. Structure of Specimen Plate

Figure 32:
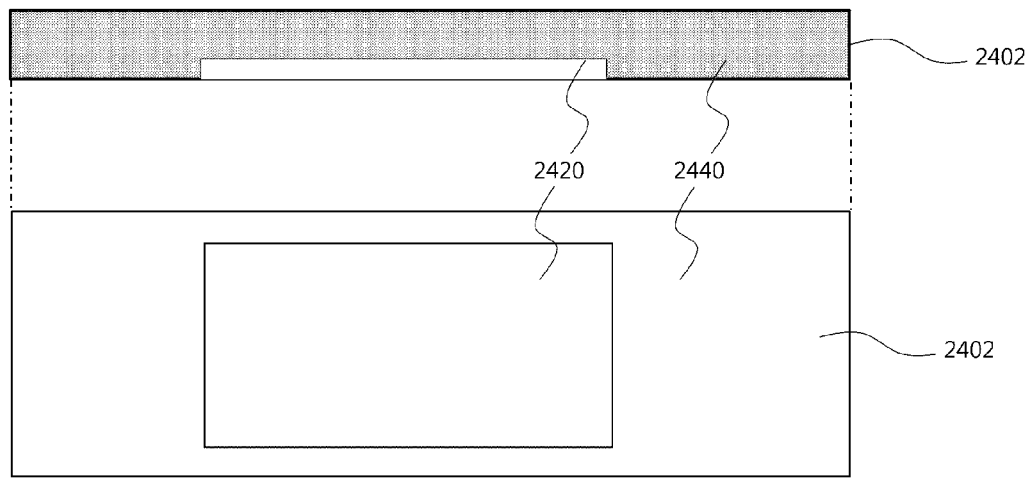
FIG. 32 is a view related to an example of a specimen plate of the sliding type test kit according to FIG. 30.

FIG. 32 is a view related to an example of a specimen plate 2400 of the sliding type test kit 2000 according to FIG. 30.

Referring to FIG. 32, the specimen plate 2400 may have a quadrilateral (preferably, rectangular) plate-shaped body 2402 having an inner surface, an outer surface, and a side surface. The inner surface is a surface facing the patch plate 2200.

Here, the specimen plate 2400 may be formed with a glass material. For example, a slide glass may be used as the specimen plate 2400.

A specimen region 2420 may be provided at the inner surface of the specimen plate 2400. Preferably, the specimen region 2420 may be prepared as a rectangular or square region. The size of the specimen region 2420 may be larger than that of a contact surface of a contact-type patch contained in the storage 2220, the contact surface being opposite the specimen plate 2400.

The specimen T may be smeared in the specimen region 2420. Specifically, in the specimen region 2420, the specimen T may be smeared through a process in which the specimen T inserted into the loading unit 2250 is moved to the smearing unit 2240 and the smearing unit 2240 passes over the specimen region 2420. Here, a surface of the specimen region 2420 may be specially treated to facilitate smearing of the specimen T.

Regions of the inner surface of the specimen plate 2400 except the specimen region 2420 may be a non-specimen region 2440. As described above with respect to the rotating-type test kit, the non-specimen region 2440 may be a region in which the specimen T is not expected to be placed or smeared. Thus, a surface of the non-specimen region 2440 may be treated so that the non-specimen region 2440 exhibits characteristics opposite to those of the surface of the specimen region 2420.

A step may be provided between the specimen region 2420 and the non-specimen region 2440.

3.3.3 Staining Process Using Test Kit

It has been mentioned above that a staining process for a specimen T may be conducted by the patch plate 2200 bringing a contact-type patch into contact with a smeared specimen T on the specimen plate 2400 while sliding relative to the specimen plate 2400.

Hereinafter, specifically, a process in which the test kit 2000 performs staining by bringing a contact-type patch into contact with a specimen T will be described.

Figure 33:
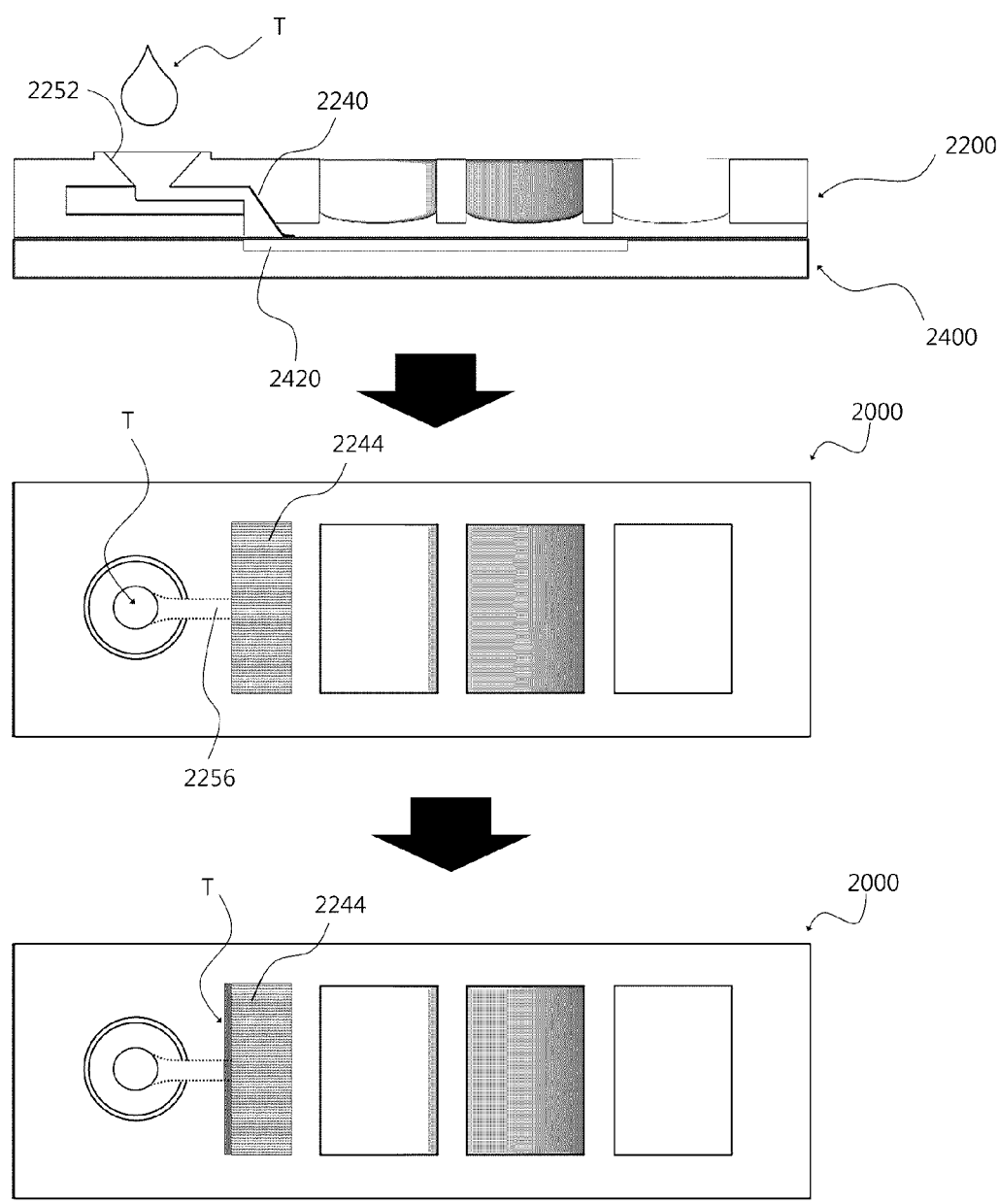
FIG. 33 is an operational view of specimen insertion using the sliding type test kit according to FIG. 30.

FIG. 33 is an operational view of specimen inserting operation using the sliding type test kit 2000 according to FIG. 30.

First, referring to the first drawing in FIG. 33, the two plates 2200 and 2400 are aligned so that the smearing unit 2240 of the patch plate 2200 is disposed at an end side of the specimen region 2420 of the specimen plate 2400. In this state, a specimen T is inserted through the inlet 2252.

Next, referring to the second drawing in FIG. 33, the inserted specimen T is dropped to the receiving unit 2254 and moves again to the smearing unit 2240 along a flow path through the channel portion 2256.

Then, referring to the last drawing in FIG. 33, the channel portion 2256 moves the specimen T to the smearing film 2244 through the flow path, and upon receiving the specimen T through the flow path, the smearing film 2244 spreads the specimen T in a vertical direction from the longitudinal direction of the smearing film 2244, i.e., the longitudinal direction of the test kit 2000.

Figure 34:
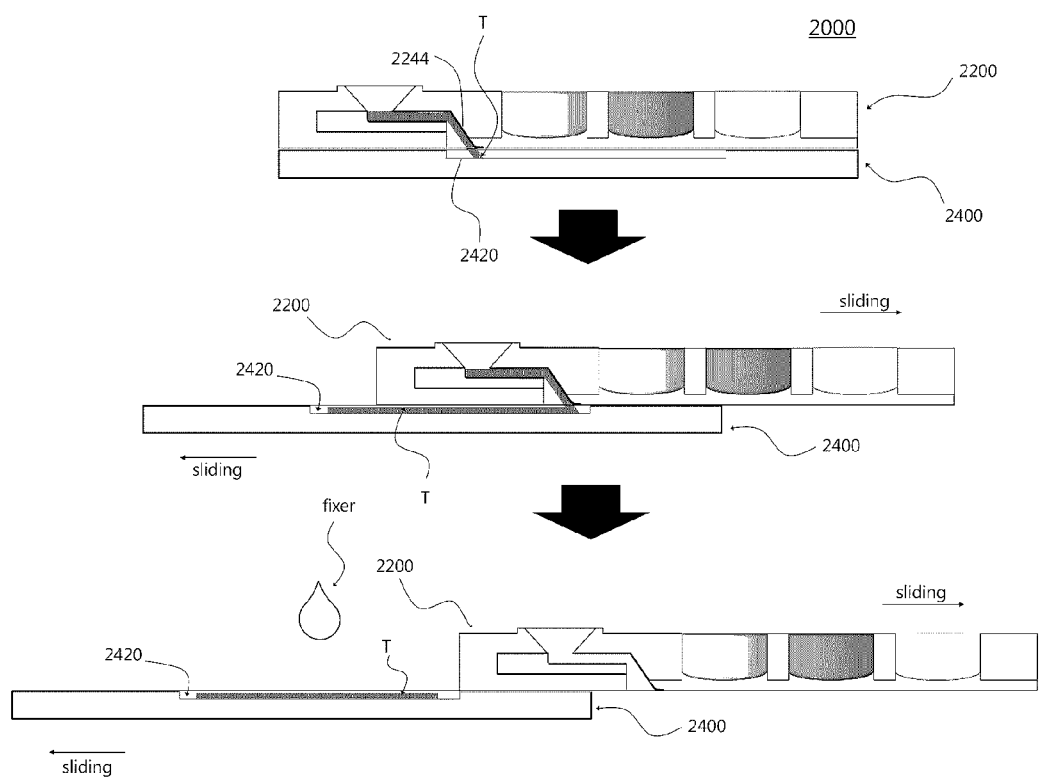
FIG. 34 is an operational view of specimen smearing using the sliding type test kit according to FIG. 30.

FIG. 34 is an operational view of specimen smearing using the sliding type test kit 2000 according to FIG. 30.

Next, referring to the first drawing in FIG. 34, the specimen T that has reached the smearing film 2244 moves to the specimen region 2420 along the smearing film 2244 by the capillary action. Here, as described above, the smearing film 2244 spreads the specimen T in the longitudinal direction of the smearing film 2244 on an upper portion of the end side of the specimen region 2420.

In this state, referring to the second drawing in FIG. 34, the two plates 2200 and 2400 are slid relative to each other. Here, the sliding direction may be a direction in which the smearing film 2244 moves from one end side to the other end side of the specimen region 2420. Accordingly, the specimen T may be smeared on the specimen region 2420 by the smearing film 2244.

When the specimen T is smeared, the two plates 2200 and 2400 are moved relative to each other again so that the entire specimen region 2420 or a portion thereof is exposed to the outside as shown in the last drawing in FIG. 34. When the specimen region 2420 is exposed to the outside while the specimen T is smeared, a specimen fixing agent such as methanol may be added to the specimen region T to fix the specimen T in the smeared state. This step may be omitted as necessary.

Figure 35:
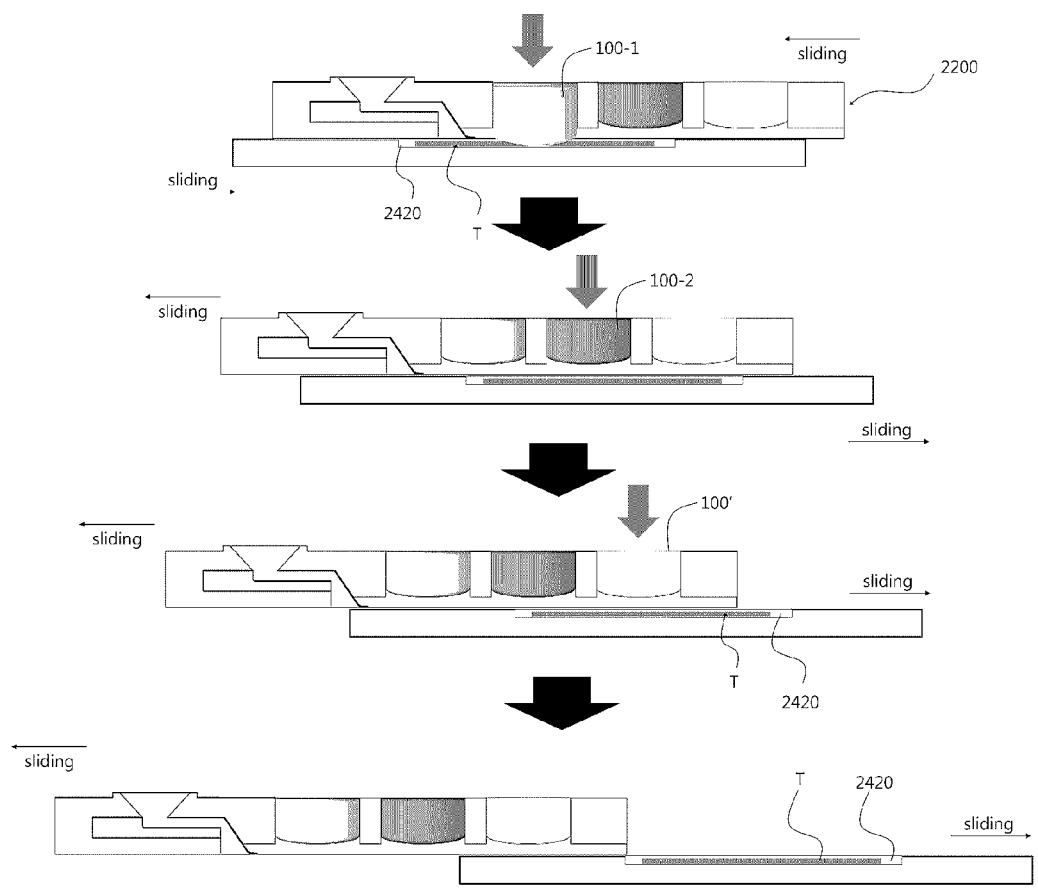
FIG. 35 is an operational view of staining using the sliding type test kit according to FIG. 30.

FIG. 35 is an operational view of staining using the sliding type test kit 2000 according to FIG. 30.

Referring to the first drawing in FIG. 35, the two plates 2200 and 2400 are slid so that the specimen region 2420 and the storage 2220 are disposed opposite each other in a state in which the specimen T is smeared. Here, the two plates 2200 and 2400 may be slid so that centers of the specimen region 2420 and the storage 2220 or centers of the specimen region 2420 and a contact-type patch contained in the storage 2220 substantially match when viewed in a vertical direction. In this state, a pressure or force is applied from the outer surface of the patch plate 2200 to the contact-type patch so that the contact-type patch is brought into contact with the specimen T. In this way, staining of the specimen T may be performed by the contact-type patch.

When a plurality of contact-type patches are contained in a plurality of storages 2220, the storages 2220 are sequentially aligned with the specimen region 2420 in the order from a storage 2220 which is the closest to the loading unit 2250 to a storage 2220 farther therefrom as shown in the first to third drawings in FIG. 35, and then the contact-type patches are brought into contact with the smeared specimen T to conduct a staining process.

When all of the contact-type patches are brought into contact with the specimen T, the two plates 2200 and 2400 are slid so that the specimen region 2420 is exposed to the outside as shown in the last drawing in FIG. 35. Here, the sliding direction may be any direction that exposes the specimen region 2420 at a side far from the loading unit 2250 as illustrated in FIG. 35 or a direction that exposes the specimen region 2420 at a side close to the loading unit 2250 as shown in the last drawing in FIG. 34.

An observation hole may be provided in an upper portion of the patch plate 2200. Here, the two plates 2200 and 2400 may also be slid so that the specimen region 2420 is disposed at a position at which the specimen region 2420 is aligned with the observation hole.

In such arrangement, a staining result of the specimen T may be observed with an optical device such as a microscope or a camera or with visual inspection.

3.3.4. Modified Example of Loading Unit

Although the loading unit 2250 has been described as being disposed in the patch plate 2200 in the above description of the sliding type test kit 2000, instead, the loading unit 2250 may also be disposed on the specimen plate 2400.

Figure 36:
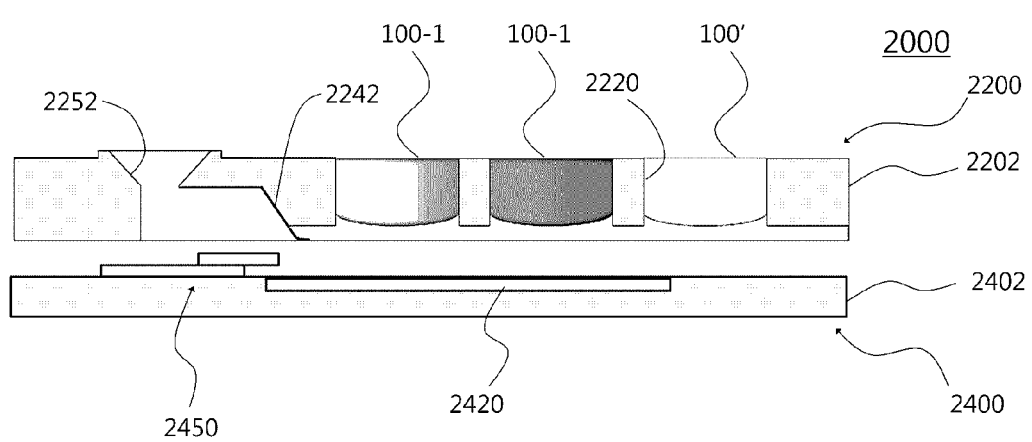
FIG. 36 is a side view of another example of a sliding type test kit according to an embodiment of the present disclosure.
Figure 37:
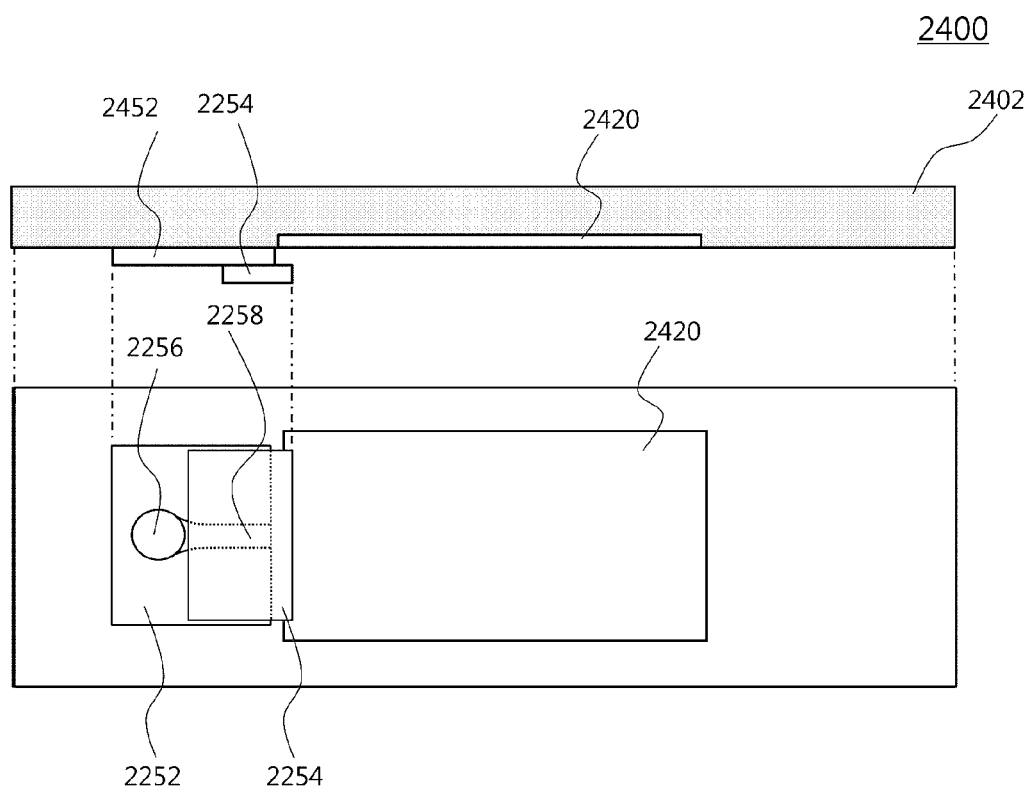
FIG. 37 is a view related to an example of a specimen plate of the sliding type test kit according to FIG. 36.

FIG. 36 is a side view of another example of a sliding type test kit 2000 according to an embodiment of the present disclosure, and FIG. 37 is a view related to an example of a specimen plate 2400 of the sliding type test kit 2000 according to FIG. 36.

Referring to FIGS. 36 and 37, it can be seen that, unlike the above description, the loading unit 2250 is disposed on the specimen plate 2400.

Here, an inlet 2252 through which a specimen T is inserted is provided in the patch plate 2200. A loading unit 2450 is provided on the specimen plate 2400 through the inlet 2252.

Specifically, the loading unit 2450 of the specimen plate 2400 may include an accommodator 2252. The accommodator 2252 accommodates the specimen T inserted through the inlet 2252.

The accommodator 2252 may include a receiving unit 2256 and a channel portion 2458. For example, the accommodator 2252 may be provided in the form of a film on which the receiving unit 2456 and the channel portion 2458 are formed. Here, the receiving unit 2456 may be a position on which an initially-inserted specimen T is received, and the channel portion 2458 may be a flow path from the receiving unit 2456 to the smearing unit 2240. As an example, the flow path may be a micro channel. The specimen T may be delivered to the smearing unit 2240 through the channel portion 2458.

The loading unit 2450 may further include a movement guide 2454. Here, the movement guide 2454 interacts with the channel portion 2458 and guides the capillary action so that the specimen T accommodated in the receiving unit 2456 is delivered to the smearing unit 2240 through the flow path.

The movement guide 2254 may be provided as a film that partially covers the accommodator 2252. Preferably, the movement guide 2454 covers at least a portion of the channel portion 2458 to limit a size of a flow path of the channel portion 2458 so that an environment in which induction of the capillary action is facilitated is created in the specimen T.

The movement guide 2454 may be disposed so that a portion thereof extends to an outer side of the accommodator 2252. Preferably, the movement guide 2454 may be disposed to extend from an end of the channel portion 2458, i.e., the other end of the receiving unit 2456, to the outer side of the accommodator 2252.

Accordingly, the specimen T may move along the channel portion 2258 and be spread, from an end of the channel portion 2258, in a direction perpendicular to the channel portion 2258 by the movement guide 2454 In this way, the specimen T spreads to the specimen region 2420 in a vertical direction from a sliding direction, so that the specimen T may be smeared by sliding operation afterwards.

It should be self-evident that, even when the sliding type test kit modified as above is used, a staining operation may be performed substantially similar to that performed by the sliding type test kit 2000 according to FIG. 30.

3.4. Modified Example of Sliding Type Test Kit

The structure of the sliding type test kit 2000 has been described above. However, the structure of the sliding type test kit 2000 may be modified in various ways. Particularly, the arrangement order of the loading unit 2250, the storage 2220, and the smearing unit 2240 may be modified in various ways to properly adjust a direction or the number of sliding operations.

Hereinafter, an example of various modified examples will be described. However, the example below does not limit various modified examples, and the sliding type test kit 2000 may also be provided in various forms other than the example which will be described below.

Figure 38:
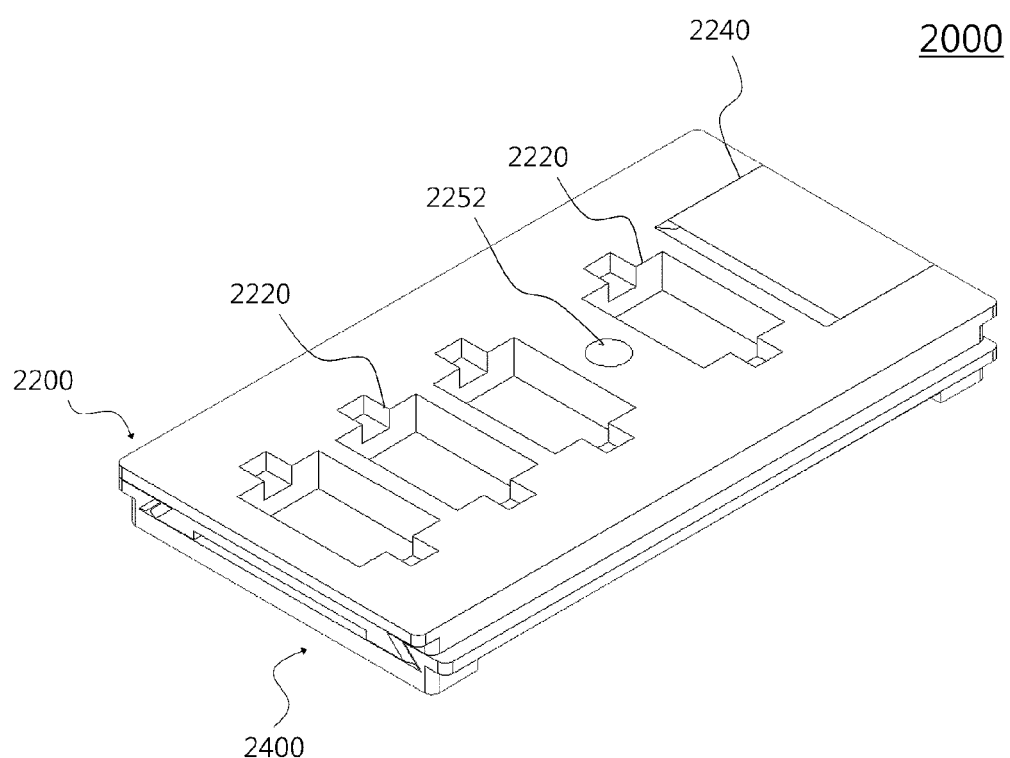
FIG. 38 is a perspective view of a modified example of a sliding type test kit according to an embodiment of the present disclosure.
Figure 39:
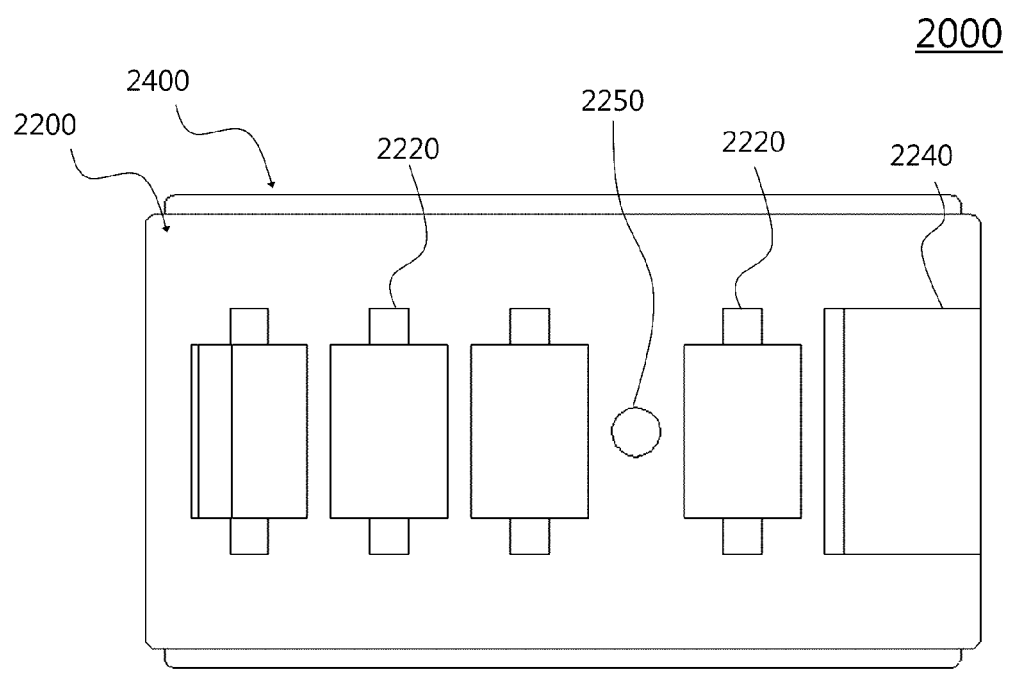
FIG. 39 is a plan view of the modified example of a sliding type test kit according to an embodiment of the present disclosure.
Figure 40:
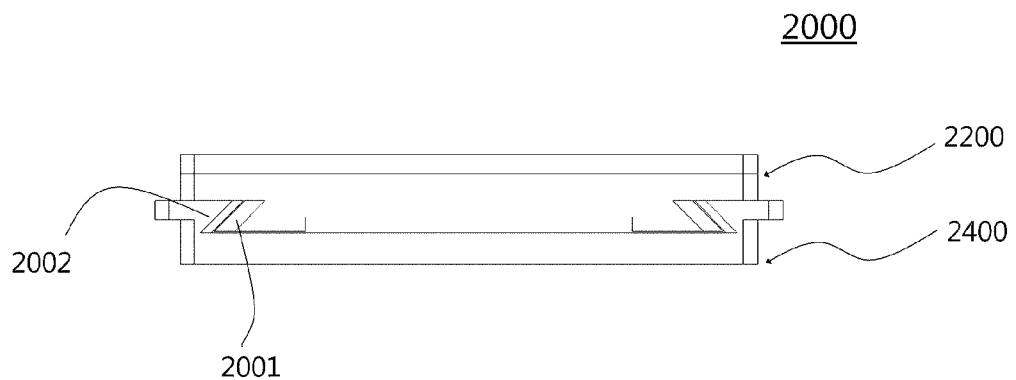
FIG. 40 is a side view of the modified example of a sliding type test kit according to an embodiment of the present disclosure.

FIG. 38 is a perspective view of a modified example of a sliding type test kit 2000 according to an embodiment of the present disclosure, FIG. 39 is a plan view of the modified example of the sliding type test kit 2000 according to an embodiment of the present disclosure, and FIG. 40 is a side view of the modified example of the sliding type test kit 2000 according to an embodiment of the present disclosure.

Referring to FIGS. 38 to 40, a sliding type test kit 2000 according to a modified example may have a patch plate 2200 and a specimen plate 2400, and as described above, the patch plate 2200 and the specimen plate 2400 may respectively include rectangular plate-shaped bodies 2202 and 2402, respectively.

Referring to FIG. 40, a protrusion 2001, a groove 2002, and the like may be formed at the patch plate 2200 and the specimen plate 2400 such that the patch plate 2200 and the specimen plate 2400 may be coupled to each other.

The patch plate 2200 may include a storage 2220 configured to store a contact-type patch, a loading unit 2250 into which a specimen T is inserted, and a smearing unit 2240 configured to smear the specimen T.

The specimen plate 2400 may include a specimen region 2420.

Here, a smearing unit 2240, a storage 2220, a loading unit 2250, and another storage 2220 may be sequentially disposed in that order from one side of an upper portion of the patch plate 2200.

Particularly, at least two storages 2220 may be disposed in the test kit 2000. One of the storages 2220 may be disposed between the loading unit 2250 and the smearing unit 2240, and the other storage 2220 may be disposed opposite the smearing unit 2240 while the loading unit 2250 is disposed therebetween.

Here, like the above-described storage, the storage 2220 disposed opposite the smearing unit 2240 may contain a contact-type patch.

The storage 2220 disposed between the loading unit 2250 and the smearing unit 2240 may contain a fixing patch, i.e., a patch used in fixation. A porous member (for example, sponge) holding a fixing agent such as alcohol may be used in place of the fixing patch. This is applicable to all of the above-described embodiments.

Alternatively, the storage 2220 disposed between the loading unit 2250 and the smearing unit 2240 may accommodate a fixing agent, e.g., alcohol such as ethanol or methanol. Here, the storage 2220 is formed so that an inner portion thereof is a space isolated from the outside, and particularly, a lower surface of the storage 2220 is configured so that a liquid-phase fixing agent accommodated in the inner portion of the storage 2220 may be discharged to the outside by a specific operation. For example, the lower surface of the storage 2220 may be formed of a membrane, and the corresponding membrane may be configured to be torn by an operation of sliding the two plates 2200 and 2400 or a stamping operation (for example, a protrusion is formed in the specimen plate 2400, and when the patch plate 2200 is pressed toward the specimen plate 2400, the membrane is torn by the protrusion such that the liquid-phase fixing agent comes out of the membrane).

Operation of the test kit 2000 having such a form is as follows.

First, a specimen T is inserted through the loading unit 2250. The specimen T is placed on the specimen region 2420 through the inlet 2252.

In this state, the two plates 2200 and 2400 are slid in one direction so that the specimen T is brought into contact with the film 2244 of the smearing unit 2240, and then the two plates 2200 and 2400 are slid in another direction so that the specimen T is smeared in the specimen region 2420.

Next, the two plates 2200 and 2400 are slid again in another direction so that the storage 2220 between the loading unit 2250 and the smearing unit 2240 is disposed on a region in which the specimen T is smeared.

In this state, when a fixing patch is contained in the storage 2220, the fixing patch is brought into contact with the specimen T by stamping so that the specimen T is fixed.

When a liquid-phase fixing agent, instead of the fixing patch, is accommodated in the storage 2220 the liquid-phase fixing agent may be made to come out and be applied on the specimen T by stamping operation so that the specimen T is fixed.

Here, the operation of fixing smeared blood using a fixing patch or a fixing agent may be performed after a predetermined amount of time after smearing. When a smeared specimen that is not sufficiently dried comes into contact with a fixing patch or a fixing agent is applied to the smeared specimen in such a state, the specimen may not be properly fixed, and a phenomenon in which blood (sample) spreads may occur. Particularly, even when a fixing patch is disposed in the vicinity of blood, instead of being brought into contact with the blood, before the blood is sufficiently dried, the phenomenon in which blood spreads due to vaporization of a fixing agent such as methanol may occur. Therefore, it may be preferable to perform sliding operation (or rotating operation) after a predetermined amount of time after the specimen T is smeared.

When the specimen T is fixed, the storage 2220 opposite the smearing unit 2240 is disposed against the fixed specimen T again so that staining is performed while a patch contained in each storage 2220 is brought into contact with the specimen T.

Unlike the other test kit 2000 described above, the test kit 2000 according to the present modified example allows fixation and staining to be performed just by sliding in one direction, after the smearing unit 2240 is first brought into contact with the specimen T. Thus, the test kit 2000 according to the present modified example has an advantage in that it is convenient for a user to use the test kit 2000.

An example in which, during smearing, a smearing unit moves (slides or rotates) in one direction to come into contact with a specimen so that the specimen is spread, and then the smearing unit is moved in another direction so that the specimen is smeared in a specimen region, has been described above. However, unlike the above-described example, during smearing, a former operation (operation in which the specimen and the smearing unit come into contact) and a latter operation (operation in which the specimen in contact is smeared) may be performed in the same direction. For this, a direction of the smearing film may be set to be the same as or opposite that in the above-described example, and a positional relationship between the smearing unit and the specimen region may be designed to be reverse.

3.5. Smearing Method

It has been described above that, in a smearing means using a test kit, a smearing film moves in a direction in which a specimen is dropped (forward direction) so that the specimen is spread in a longitudinal direction of a slide S, and then the smearing film moves in another direction (reverse direction) so that the specimen is smeared in specimen regions 1420 and 2420 of the slide S.

Figure 41:
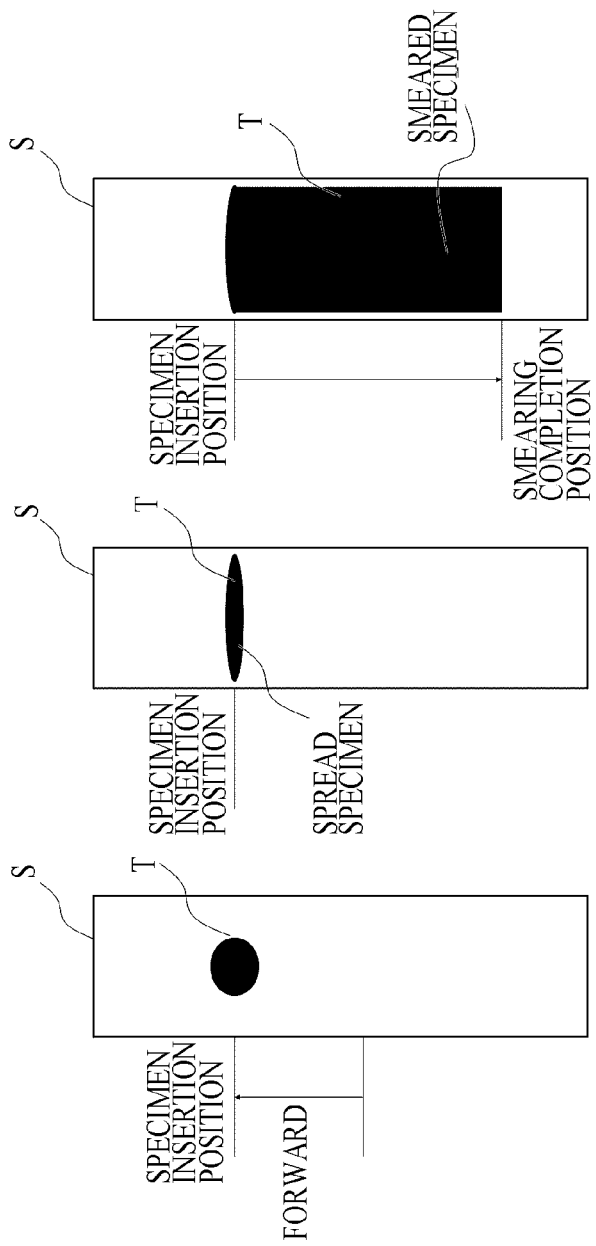
FIG. 41 is an example of a specimen smearing means according to an embodiment of the present disclosure.

Such a method is illustrated in FIG. 41. FIG. 41 is an example of a specimen smearing means according to an embodiment of the present disclosure. Although FIG. 41 has been described with reference to the sliding type test kit 2000, the description may also be applied to the rotating-type test kit 1000 when a sliding direction of the sliding type test kit 2000 is changed to a rotating direction.

However, such a smearing method (smearing method) may be modified in various ways. Modified examples of the smearing method will be described in detail below.

3.5.1. Smearing Means

Instead of a smearing film moving in a forward direction up to a specimen T, coming into contact with the specimen T so that the specimen is spread in a width direction of the smearing film (that is, a width direction of a slide S), and then moving in a reverse direction so that the specimen T is smeared in a specimen region, when moving in the forward direction toward the specimen T, the smearing film may move past the specimen T by a predetermined distance (up to a turning position) and then move in the reverse direction.

Figure 42:
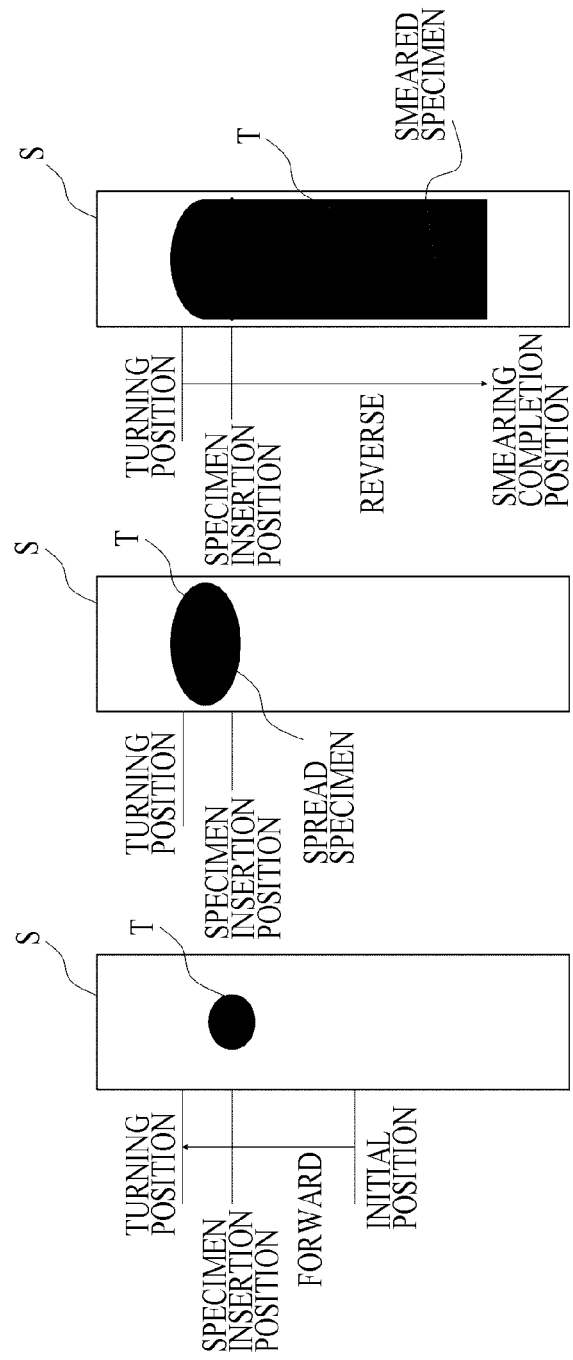
FIG. 42 is another example of a specimen smearing means according to an embodiment of the present disclosure.

FIG. 42 is another example of a specimen smearing means according to an embodiment of the present disclosure.

Referring to FIG. 42, for example, a smearing film may move from an initial position to a specimen insertion (injection) position and then, instead of stopping at the specimen insertion position, move to a turning position, which is opposite the initial position with the specimen insertion position disposed between the turning position and the initial position, while sweeping the specimen T. When, unlike the means in FIG. 41, the turning position is behind the specimen insertion position, the specimen T may be naturally spread in the width direction of the smearing film by the smearing film being moved while sweeping the specimen T, instead of the specimen being spread in the width direction of the smearing film due to the capillary action while the smearing film is stopped at the specimen insertion position.

Then, as the smearing film moves again in the reverse direction from the turning position, the specimen T may be smeared.

Here, a distance from the specimen insertion position to the turning position may be approximately 1/5 of a distance from the specimen insertion position to a smearing completion position.

3.5.2. Smearing Film

Although description has been given above mainly on the basis of a specimen-friendly smearing film, smearing films may be classified into specimen-friendly films and non-specimen-friendly films in accordance with properties of surfaces thereof.

For example, when a specimen T is blood, a hydrophilic smearing film may be used. That is, a surface of a smearing film may be coated to be hydrophilic, or a smearing film itself may be manufactured with a hydrophilic material.

When a smearing film that is friendly to a specimen T is used as above, during a smearing operation, the specimen T may be spread in the width direction of the film just by contact between the specimen and the smearing film, without moving the smearing film to sweep the specimen T.

When the smearing film moves in a reverse direction, the specimen T may follow the smearing film and be smeared in a specimen region.

However, in this case, when a failure occurs in adjusting an amount of inserted specimen, an angle formed between the smearing film and the slide and a movement speed of the smearing film may be required to be adjusted finely for the specimen T to be smeared in a monolayer.

However, when it is easy to adjust the angle and the speed, there is an advantage in that monolayer smearing (thin smearing) and multi-layer smearing (thick smearing) may be freely adjusted for For example, screening for cancer mostly requires monolayer smearing whereas an examination for malaria sometimes requires multi-layer smearing, and such cases may be handled accordingly.

Unlike the above, a surface of a smearing film may be non-specimen (sample)-friendly.

For example, when a specimen T is blood, a hydrophobic smearing film may be used. That is, a surface of a smearing film may be coated to be hydrophobic, or a smearing film itself may be manufactured with a hydrophobic material.

When a smearing film that is not friendly to a specimen T is used as above, during a smearing operation, it may be advantageous for the smearing film to move while sweeping the specimen T such that, due to a force of the smearing film, the specimen T is spread in the width direction of the smearing film. A means shown in FIG. 41 is also applicable depending on surface properties of a slide and an angle of the smearing film or the like.

When a non-specimen (sample)-friendly smearing film is used, since a force in which the specimen T is adhered to the smearing film somewhat weakens, there is an advantage in that thin smearing is slightly more facilitated in comparison to when using a specimen-friendly film.

3.5.3. Smearing Speed and Smearing Angle

During smearing using a smearing film, a smearing speed and an angle between the smearing film and a slide may be important.

The smaller the angle, the capillary action is more pronounced such that a specimen T tends to be well-adhered to the film. Conversely, the larger the angle, the capillary action is less pronounced such that a force with which the specimen T is adhered to the film weakens.

Consequently, a smearing speed may be increased when the smearing angle is small, and conversely, the smearing speed may be decreased when the smearing angle is large.

When attempting to perform thin smearing, the angle may be enlarged or the smearing speed may be increased. When attempting to perform thick smearing, the angle may be reduced or the smearing speed may be decreased.

According to an example of the present disclosure, a proper smearing angle may be approximately 30 to 45°.

When the smearing speed is properly adjusted at the smearing angle in the above range, thin smearing and thick smearing may be simultaneously performed in one smearing. That is, when a smearing speed is set to be high in an early stage of smearing while the smearing speed is set to be low in a later stage of smearing, thin smearing may be performed on a front portion, and thick smearing may be performed on a rear portion. Of course, the opposite may also be performed.

The above description is merely illustrative of the technical spirit of the present disclosure, and one of ordinary skill in the art to which the present disclosure pertains should be able to make various changes and modifications within the scope not departing from essential features of the present disclosure. Therefore, the above-described embodiments of the present disclosure may be implemented separately from each other or in combination.

Therefore, the embodiments disclosed herein are for describing, instead of limiting, the technical spirit of the present disclosure, and the scope of the technical spirit of the present disclosure is not limited by such embodiments. The scope of the present disclosure should be interpreted by the claims below, and all technical spirits within the equivalent scope should be interpreted as belong to the scope of the present disclosure.

4. Diagnostic System

A test kit that stains a specimen T upon insertion of the specimen T has been described above. Hereinafter, a diagnostic system 4300 according to an embodiment of the present disclosure that uses the above-described test kit and automatically performs diagnosis of a specimen T will be described.

The diagnostic system 4300 according to an embodiment of the present disclosure may perform a diagnostic operation in which an image of a specimen T, which is stained through a process of smearing and/or staining the specimen T inserted into the test kit, is acquired, the acquired image is analyzed and diagnosed, and a result of diagnosis of a state of the specimen T is provided as feedback to a user of the diagnostic system 4300.

By using the diagnostic system 4300 capable of controlling the above-described test kit and diagnosing a state of the specimen T, the user may solve problems such as cumbersomeness of a specimen T diagnosis process due to the user directly and manually manipulating the test kit or inaccuracy of a result of diagnosis of the specimen T.

Here, test kits used by the diagnostic system 4300 include the above-described rotating-type test kit and/or sliding type test kit and/or modified examples thereof. Hereinafter, operation of the diagnostic system 4300 will be described in accordance with terminologies related to structures of the above-described test kits.

Figure 43:
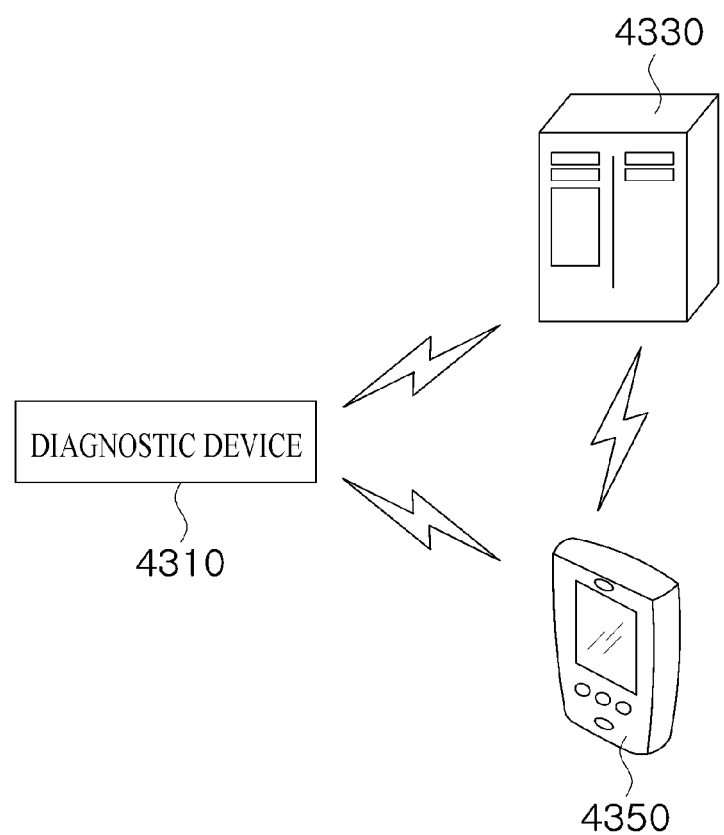
FIG. 43 is a view illustrating a configuration example of a diagnostic system according to an embodiment of the present disclosure.

FIG. 43 is a view illustrating a configuration example of the diagnostic system 4300 according to an embodiment of the present disclosure.

Referring to FIG. 43, for example, the diagnostic system 4300 may include a diagnostic device 4310, a server 4330, and/or a user terminal 4350. The elements of the system may be connected to transmit data resources and the like through wireless Internet or a network such as a wireless communication network.

The diagnostic device 4310 according to an embodiment of the present disclosure may perform a diagnostic operation including a staining operation in which a specimen T placed in a test kit is smeared and/or a smearing operation in which the specimen T is stained. The diagnostic device 4310 may exchange data acquired in a series of diagnostic operation processes with another external device. For example, the diagnostic device 4310 may transmit data acquired from the stained specimen T to the user terminal 4350 through a communication network or the like and receive feedback data therefrom, and may also exchange data with the server 4330.

The server 4330 according to an embodiment of the present disclosure may exchange data resources with external devices such as the diagnostic device 4310 and/or the user terminal 4350 connected to the server 4330 and may contain data resources. The server 4330 may be connected to the external devices to integrate information of the external devices and provide the integrated information so that a user of the diagnostic system 4300 can conveniently use the integrated information.

The user terminal 4350 according to an embodiment of the present disclosure may include any device capable of being connected to the server 4330 and/or the diagnostic device 4310. For example, the user terminal 4350 may include a mobile terminal, a computer, a laptop, a smartphone, a personal digital assistant (PDA), a smart band, a smart watch, or the like.

Hereinafter, the elements of the diagnostic device 4310 for performing the diagnostic operation of the diagnostic system 4300 and operations of the elements will be described in more detail.

4.1 Diagnostic Device

The diagnostic device 4310 according to an embodiment of the present disclosure may be a device configured to smear a specimen T placed in a test kit, stain the smeared specimen T, and acquire an image of the stained specimen T.

Figure 44:
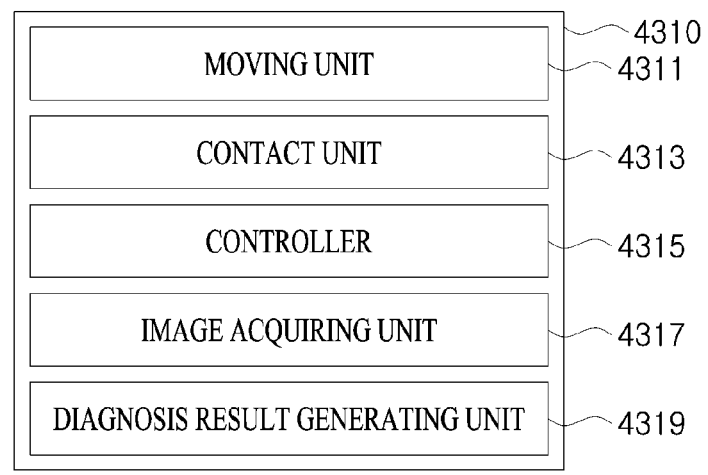
FIG. 44 is a block diagram of an example of elements constituting a diagnostic device according to an embodiment of the present disclosure.

FIG. 44 is a block diagram of an example of elements constituting the diagnostic device 4310 according to an embodiment of the present disclosure.

Referring to FIG. 44, for example, the diagnostic device 4310 may include a moving unit 4311 configured to perform a series of operations for moving a structure of a test kit, a contact unit 4313 configured to perform an operation in which a contact-type patch contained in a patch plate is brought into contact with the specimen T for staining the specimen T, an image acquiring unit 4317 a diagnosis result generator 4319 and/or other elements A space capable of providing a test kit to the diagnostic device 4310 may be formed in the diagnostic device 4310 according to an embodiment of the present disclosure. To facilitate description, a space in which a test kit may be provided will be referred to as a loading region 4610. The loading region 4610 may be formed in any shape as long as the loading region 4610 is a space capable of providing a test kit to the diagnostic device 4310. A user of the diagnostic device 4310 may provide a test kit to the diagnostic device 4310 through the loading region 4610. The shape of the loading region according to an embodiment of the present disclosure will be described in Section "4.3 Implementation of diagnostic system of present disclosure."

Figure 45:
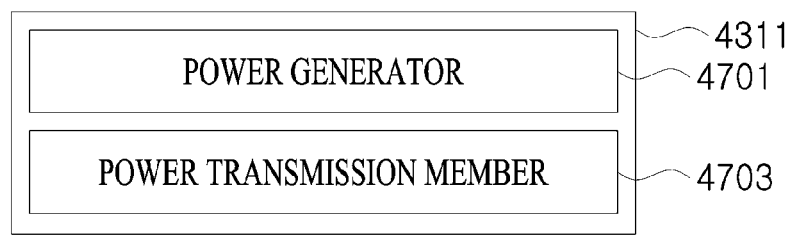
FIG. 45 is a perspective view of an example of a diagnostic device according to an embodiment of the present disclosure.

The moving unit 4311 according to an embodiment of the present disclosure may be formed of elements for moving a structure of a test kit. As shown in FIG. 45, the moving unit 4311 may include a power generator configured to generate power and power transmission members configured to transmit power generated by the power generator to the structure of the test kit.

Although the contact unit 4313 may be formed at an upper portion of the loading region 4610 on which a test kit is placed as shown in FIG. 45, embodiments are not limited thereto, and the contact unit 4313 may be present at any position, such as an inner portion of the diagnostic device 4310 or an outer surface of the diagnostic device 4310, at which an operation of bringing a contact-type patch contained in a test kit into contact with a specimen T may be performed.

Hereinafter, the elements that may constitute the diagnostic device 4310 will be described in more detail.

4.1.1 Moving Unit

The moving unit 4311 according to an embodiment of the present disclosure may move a structure of a test kit for operations of smearing and/or staining a specimen T placed in the test kit. For example, the moving unit may move a patch plate, a specimen plate, a smearing unit, a loading region 4610, and the like which constitute a structure of the above-described test kit. To facilitate description, an operation in which the moving unit 4311 moves a structure of a test kit will be referred to as a moving operation below.

FIG. 45 is a block diagram illustrating an example of the moving unit 4311 according to an embodiment of the present disclosure.

Referring to FIG. 45, the moving unit 4311 may include a power transmission member 4703 configured to transmit power to a test kit so that a moving operation is performed and/or a power generator 4701 configured to generate the power. There may be a plurality of power transmission members 4703 and/or a plurality of power generators 4701, and the power transmission member 4703 and/or the power generator 4701 may not be present according to circumstances.

The power generator 4701 may be provided in any shape as long as the power generator 4701 is capable of generating power for the moving operation of the moving unit 4311. The power transmission member 4703 may be provided in any shape as long as the power transmission member 4703 is capable of transmitting power to a test kit.

Here, the power transmission member 4703 may be implemented in the form in which a specimen plate and/or a patch plate of a test kit are individually movable or the form in which only one of a specimen plate and/or a patch plate is moved and the other plate is fixed.

The above-described predetermined power transmission member 4703 may be individually connected to a structure of a test kit placed on the loading region 4610. For example, the power transmission member may be implemented in the form including a first mounting portion on which a patch plate of a test kit placed on the loading region 4610 is mounted and a second mounting portion on which a specimen plate is mounted. The moving operation in which each plate is moved may be performed by power being transmitted to a specimen plate and/or a patch plate of a test kit through the first mounting portion and/or the second mounting portion.

The power transmission member 4703 and/or the power generator 4701 may be implemented in various different forms in accordance with various forms of the moving unit 4311. Hereinafter, various forms of the moving unit 4311 will be described.

The moving unit 4311 according to an embodiment of the present disclosure may have a mechanical form or may also have an electromagnetic form.

Here, the moving unit 4311 having a mechanical form may refer to a form of the moving unit 4311 including a predetermined configuration of the power transmission member 4703 that allows the power transmission member 4703 capable of transmitting power to a test kit and the power generator 4701 configured to generate mechanical power to be connected and/or come into contact with each other so that power generated by the power generator 4701 may be transmitted to a test kit in accordance with a mechanical connection means.

Here, the form of the power generator 4701 configured to generate mechanical power is not limited, and the power generator 4701 may be implemented in various forms. As an example, the power generator 4701 may be implemented in the form of a motor. The power generator 4701 may be a DC motor, an AC motor, a DC/AC motor, a brushless DC motor, a linear induction motor, a synchronous reluctance motor, a step motor, or the like capable of generating rotation power.

The power generator 4701 may also be implemented as a cylinder type power generator 4701 that uses a fluid or gas. The cylinder type power generator 4701 may generate power in the form of a pressure caused by a fluid and/or gas, transmit the generated power to a structure of a test kit, and perform the moving operation of the moving unit 4311.

The moving unit 4311 having an electromagnetic form may refer to a form in which the power generator 4701 generates power in the form of an electric force and/or a magnetic force, affects a test kit, and performs the moving operation.

For example, a power generator 4701 of the moving unit 4311 having an electromagnetic form may be a power generator 4701 that utilizes an electromagnet. The moving unit 4311 having an electromagnetic form may perform the moving operation by allowing a test kit to be affected by a magnetic force generated by the electromagnetic power generator 4701 so that a structure of the test kit is moved. The method of moving the structure of the test kit by a magnetic force may include a method in which the structure of the test kit is moved by adjusting a strength of a magnetic force generated by the electromagnetic power generator 4701, a method in which the electromagnetic power generator 4701 itself is moved so that the power transmission member 4703 affected thereby is moved, or the like.

Here, the structure of the test kit may be formed of a material such as a conductor capable of receiving power from the electromagnetic power generator 4701.

The form and/or the structure of the moving unit 4311 that performs the moving operation have been described above. A relative movement operation for performing smearing and staining operations during the moving operation by the moving unit 4311 and/or a moving operation for an image acquiring operation will be described in more detail below.

4.1.2 Contact Unit

The contact unit 4313 according to an embodiment of the present disclosure may move a structure of a test kit for a smeared specimen T to be stained. By moving the structure of the test kit, the contact unit 4313 may bring a contact-type patch contained in a patch plate into contact with the specimen T.

As described above, the contact-type patch may include a contact-type staining patch that comes into contact with a specimen T to stain the specimen T, and a contact-type staining supplementary patch such as a fixing patch that fixes the specimen T, a decolorizing patch and/or a mordanting patch, a buffering patch, a washing patch, and a composite patch. A plurality of contact-type patches may be sequentially contained in a patch plate.

Hereinafter, to facilitate description, the above-mentioned operation of the contact unit 4313 in which a structure of a test kit is moved for staining will be referred to as a contact operation.

Although it may seem to be more appropriate to name the contact unit 4313 a second moving unit 4311 since the contact unit 4313 performs a similar function as the moving unit 4311 in that the contact unit 4313 moves a structure of a test kit, the name of the contact unit 4313 will be kept since the contact unit 4313 is an element that has a special purpose: bringing a contact-type patch into contact with a specimen T.

Although the contact unit 4313 may solely perform the contact operation, the contact unit 4313 may also perform the contact operation in association with the above-described moving operation of the moving unit 4311.

Figure 46:
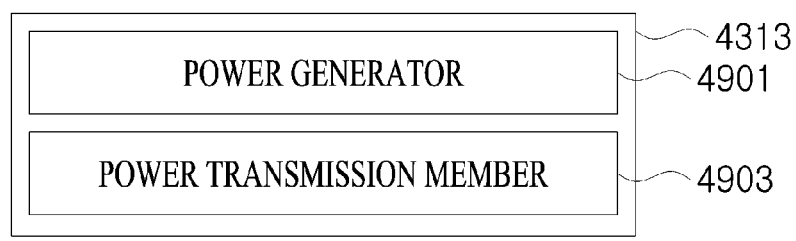
FIG. 46 is a block diagram illustrating an example of a contact unit (4313) according to an embodiment of the present disclosure.

FIG. 46 is a block diagram illustrating an example of the contact unit 4313 according to an embodiment of the present disclosure.

Referring to FIG. 46, like the above-described moving unit 4311, the contact unit 4313 may also include a power transmission member 4903 configured to move a structure of a test kit and/or a power generator 4901 configured to generate power. A plurality of power transmission members 4903 and/or a plurality of power generators 4901 may be present, and the power transmission member 4903 and/or the power generator 4901 may not be present according to circumstances.

Here, the power transmission members 4903 may serve to transmit power generated by the power generator 4901 to a structure of a test kit so that a contact-type patch contained in the test kit is moved to come into contact with a specimen T.

The power generator 4901 may be provided in any shape as long as the power generator 4901 is capable of generating power for the contact unit 4313 to perform the contact operation. The power transmission member 4903 may be provided in any shape as long as the power transmission member 4903 is capable of transmitting power to a test kit.

Like the above-described moving unit 4311, the contact unit 4313 may also be implemented in various forms. Accordingly, the power transmission member 4903 and/or the power generator 4901 may have various forms.

The contact unit 4313 according to an embodiment of the present disclosure may have a mechanical form or an electromagnetic form.

Here, the contact unit 4313 having a mechanical form may refer to a form of the contact unit 4313 in which mechanical power generated by the mechanical power generator 4901 is transmitted to a structure of a test kit through the power transmission member 4903 using a mechanical contact means so that the contact operation is performed.

The description of the mechanical power generator 4901 will be omitted since the description is the same as the description of the mechanical power generator 4701 of the moving unit 4311.

The power transmission member 4903 may transmit power generated by the mechanical power generator 4901 to a structure of a test kit. For example, the power transmission member may have a form capable of hitting a structure of a test kit by power generated by the power generator.

Here, an electromagnetic form may refer to a form in which power in the form of an electric force and/or a magnetic force is transmitted to a structure of a test kit so that the structure of the test kit is moved.

The form and/or the structure of the contact unit 4313 that performs the contact operation have been described above. A contact operation of the contact unit 4313 for a staining operation of the diagnostic device, which will be described below, will be described in more detail below.

4.1.3 Image Acquiring Unit

An image acquiring unit 4317 according to an embodiment of the present disclosure may generate an image of a stained specimen T.

The image acquiring unit 4317 according to an embodiment of the present disclosure may include means for acquiring an image of a stained specimen T. For example, the image acquiring unit 4317 may include an image generator such as an image sensor including a complementary metal-oxide semiconductor (CMOS) image sensor and a charge-coupled device (CCD) image sensor, a predetermined beam generator capable of generating a beam that transmits through a stained specimen T, and/or an optical system configured to form an image of the transmitted beam on the image generator. Elements of the image acquiring unit 4317 are not limited thereto, and any element capable of generating an image of a stained specimen T may be an element of the image acquiring unit 4317.

The optical system according to an embodiment of the present disclosure may be implemented with one or more lenses. Although it is preferable that the lenses be formed with glass, the material of the lenses is not limited, and the lenses may be implemented with any material that allows the lenses to perform an operation of forming an image of a beam on the above-described image generator.

In accordance with the above-described means of the image acquiring unit, the image acquiring unit 4317 may transmit a beam emitted from the beam generator through the optical system and/or a test kit in which a stained specimen T is placed, acquire the transmitted beam through the image generator, and generate an image.

An image of a stained specimen generated from the image acquiring unit 4317 may have various magnifications. For example, the generated image may have a magnification that enlarges the stained specimen or a magnification that shows the stained specimen in its exact size.

The image acquiring unit 4317 may have a predetermined power transmission member and/or power generator capable of moving a test kit in which a stained specimen is placed. In this way, acquisition of an image of a stained specimen can be facilitated.

4.1.4 Diagnosis Result Generator

A diagnosis result generator 4319 according to an embodiment of the present disclosure may analyze data generated in accordance with the diagnostic operation of the diagnostic system 4300 and diagnose a state of a specimen T. In the present embodiment, the diagnosis result generator 4319 may analyze an image acquired from a stained specimen T and diagnose a state of the specimen T.

The operation of the diagnosis result generator 4319 in which a state of a stained specimen T is diagnosed will be described below in Section "4.2.5. Diagnosis result generating operation."

4.1.5 Other Elements

Figure 47:
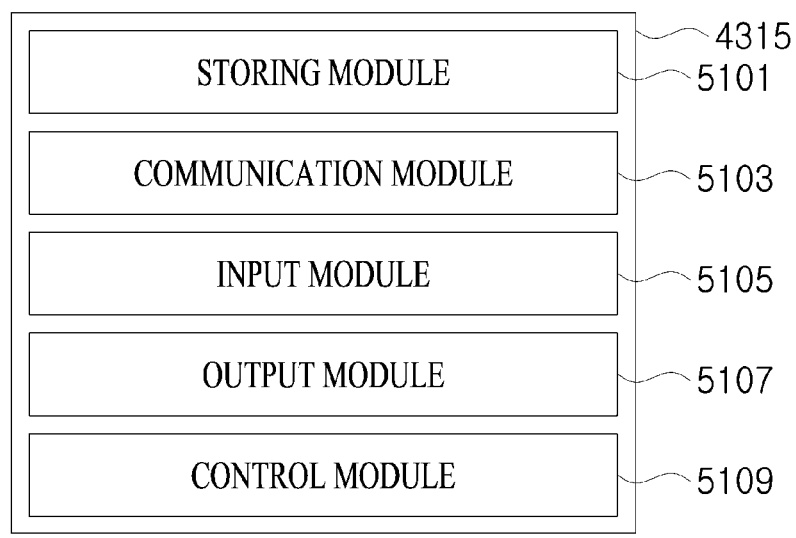
FIG. 47 is a block diagram illustrating other elements of a diagnostic device (4310) according to an embodiment of the present disclosure.

FIG. 47 is a block diagram related to other elements of a diagnostic device according to an embodiment of the present disclosure.

Devices illustrated in FIG. 47 are not essential, and other elements may have more or less elements.

Referring to FIG. 47, the other elements of the diagnostic device 4310 may include a containing module 5101 configured to store various data, a communication module 5103 configured to transmit and receive data to and from other devices, an input module 5105 configured to receive various inputs from a user, an output module 5107 configured to visualize data, and/or a control module 5109 configured to control operation of each element of the diagnostic device 4310.

The containing module 5101 may temporarily or semi-permanently contain data. An operating system (OS) for operating the diagnostic device 4310, firmware, middleware, and various programs for supporting the same may be contained in the containing module 5101, and data or the like received from other external devices such as the diagnosis result generator 4319 may be contained in the containing module 5101. Typical examples of the containing module 5101 may include a hard disk drive (HDD), a solid state drive (SSD), a flash memory, a read-only memory (ROM), a random access memory (RAM), cloud storage, or the like.

The communication module 5103 may perform communication with an external device. For example, the communication module 5103 may transmit and receive data to and from an external device. As an example, the communication module 5103 may transmit an image of a stained specimen T acquired by the diagnostic device 4310 to the diagnosis result generator 4319.

Such a communication module 5103 may communicate with an external device using a wired means and may communicate with an external device using a wireless means. For this, the communication module 5103 may include a wired communication module configured to connect to the Internet or the like through a local region network (LAN), a mobile communication module such as Long Term Evolution (LTE) configured to connect to a mobile communication network through a mobile communication base station and transmit and receive data, a short range communication module 5103 configured to use a wireless LAN (WLAN)-based communication means such as wireless fidelity (Wi-Fi) or a wireless personal region network (WPAN)-based communication means such as Bluetooth and ZigBee, a satellite communication module configured to use a global navigation satellite system (GNSS) such as a global positioning system (GPS) or a combination thereof.

The containing module 5101 may temporarily or semi-permanently contain data of a control device.

An OS for operating a local device, firmware, middleware, and various programs for supporting the same may be contained in the containing module 5101, and data or the like received from other external devices such as the server 4330 may be contained in the containing module 5101.

Typical examples of the containing module 5101 may include a HDD, a SSD, a flash memory, a ROM, a RAM, cloud storage, or the like.

The input module 5105 may receive an input related to operation of the diagnostic device 4310 from a user. For example, the input module 5105 may receive a user input related to an operation time from a user in order to set an operation time of the moving unit 4311 of the diagnostic device 4310.

The user input may be in various forms including a key input, a touch input, and a voice input. The input module 5105 is a concept that encompasses a key pad, a keyboard, or a mouse having conventional forms, as well as a touch sensor configured to sense a user's touch, a microphone configured to receive a voice signal, a camera configured to recognize a gesture or the like through image recognition, a proximity sensor including an illuminance sensor, an infrared sensor, or the like, which are configured to sense a user's approach, a motion sensor configured to recognize a user's movement using an acceleration sensor, a gyro sensor, or the like, and/or various input means configured to sense or receive various other forms of user inputs. Here, the touch sensor may be implemented as a piezoelectric or capacitive touch sensor configured to sense a touch through a touch panel or a touch film attached to a display panel, an optical touch sensor configured to sense a touch by an optical means, or the like.

The output module 5107 may output pieces of information related to the diagnostic device 4310. For example, the control device may output, through the output module 5107, whether operations of smearing and/or staining devices of the diagnostic device 4310 are being performed.

The output module 5107 may include a display configured to output an image, a speaker configured to output sound, a haptic device configured to generate vibration and/or output means of various other forms. Hereinafter, a display capable of visually delivering an image will be described as an example of the output module 5107 of an image processing device. However, an image is not necessarily output to a user through a display in the image processing device, and the image may be output to a user through any other above-described output means. The display is a concept that signifies an image display device in broad sense including all of a liquid crystal display (LCD), a light emitting diode (LED) display, an organic LED (OLED) display, a flat panel display (FPD), a transparent display, a curved display, a flexible display, a 3D display, a holographic display, a projector, and/or various other forms of devices capable of performing an image output function. Such a display may be in the form of a touch display that is integrally configured with the touch sensor of the input module 5105. In addition, instead of being implemented in the form of a device that outputs information to the outside by itself, the output module 5107 may also be implemented in the form of an output interface (universal serial bus (USB) port, a personal system 2 (PS/2) port, or the like) configured to connect an external output device to an image processing device.

The control module according to an embodiment of the present disclosure may control the overall operation of each element of the diagnostic device 4310. For example, the control module may give a start command so that an element of the above-described diagnostic device 4310 starts operation.

The control module may be implemented with a computer or a device similar thereto in accordance with hardware, software, or a combination thereof. In terms of hardware, the control module may be provided in the form of an electronic circuit such as a central processing unit (CPU) chip that processes an electrical signal and performs a control function, and in terms of software, the control module may be provided in the form of a program that operates the hardware of the control module.

The diagnostic operation of the diagnostic system 4300, in which a specimen T in a test kit of the diagnostic device 4310 is smeared, the smeared specimen T is stained, an image of the stained specimen T is generated, and a state of the specimen T is diagnosed, may be performed by operations of the above-described elements of the diagnostic device 4310. Unless particularly mentioned otherwise, it may be considered that operation of each element of the diagnostic device 4310 is controlled by the control module.

Although the moving unit 4311, the contact unit 4313, the image acquiring unit 4317, the diagnosis result generator 4319, and/or the other elements have been described above as elements included in the diagnostic device 4310, each of the elements may be implemented in the server 4330, the user terminal 4350, or the like in the diagnostic system. Each of the elements being implemented in an element of the diagnostic system other than the diagnostic device 4310 may signify that elements subordinate to each of the elements may be separately implemented in the diagnostic system.

For example, the image acquiring unit 4317 according to an embodiment of the present disclosure may be implemented in an element of the diagnostic system other than the diagnostic device 4310. As an example, the image acquiring unit 4317 may be implemented in the server 4330 and/or the user terminal 4350. From among the elements of the image acquiring unit 4317, the image generator such as an image sensor including a CCD image sensor and a CMOS image sensor may be implemented in the server 4330 and/or the user terminal 4350 of the diagnostic system, and the optical system and/or the predetermined beam generator may be implemented in the diagnostic device 4310.

For example, the diagnosis result generator 4319 according to an embodiment of the present disclosure may be implemented in an element of the diagnostic system other than the diagnostic device 4310. As an example, the diagnosis result generator 4319 may be implemented in the server 4330 and/or the user terminal 4350.

Although the diagnosis result generator 4319 may be implemented in the form of hardware that analyzes data, the diagnosis result generator 4319 may also be implemented in the form of software that is installed to perform diagnosis.

The diagnosis result generator 4319 may be solely provided inside or outside another external device. That is, the diagnosis result generator 4319 may be provided inside the diagnostic device 4310 and create a diagnosis result, may be present in the server 4330 in which pieces of information are integrated and create a diagnosis result of a specimen T on the basis of information collected by the server 4330, or may be installed in the user terminal 4350 that uses the diagnostic system 4300. That is, the diagnosis result generator 4319 may have any form as long as the diagnosis result generator 4319 is capable of analyzing data generated in accordance with the diagnostic operation of the diagnostic system 4300 and diagnosing a state of a specimen T.

The above-described elements of the diagnostic device 4310 may also not be implemented. When the elements are not implemented, the diagnostic operation to be performed by the elements, which will be described below, may be directly performed by a user.

The elements of the diagnostic device 4310 may be redundantly present in the diagnostic system. When an element is redundantly present, an element to perform a diagnostic operation of redundant elements may be selected from among the redundant elements in the system. Such selection may be made by a user or may be automatically made within the diagnostic system.

A diagnostic method in which the diagnostic system diagnoses a state of a specimen T will be described below.

4.2 Diagnostic Operation

A diagnostic system 4300 according to an embodiment of the present disclosure may perform a diagnostic operation in which a state of a specimen T is diagnosed.

Since, as described above, each element of the diagnostic system 4300 may be separately implemented in different elements of the diagnostic system 4300, a diagnostic operation, which will be described below, may be separately performed by a diagnostic device 4310, a server 4330, and/or a user terminal 4350 of the diagnostic system 4300.

The diagnostic operation of the diagnostic system 4300 according to an embodiment of the present disclosure may include a loading operation, a smearing operation, a staining operation, an image acquiring operation, and/or a diagnosis result generating operation. The above-listed operations included in the diagnostic operation may be performed by operations of the elements of the diagnostic system 4300.

For example, the loading operation, the smearing operation, and/or the image acquiring operation may be performed by an operation in which the moving unit 4311 moves a test kit in the loading region 4610 into the diagnostic system 4300 so that the test kit loaded in the loading region 4610 may be inserted into the diagnostic system 4300.

For example, the staining operation may be performed by the moving operation of the moving unit 4311 and/or the contact operation of the contact unit 4313 being performed in association with each other.

The diagnostic operation may vary in accordance with a type of a test kit used in the diagnostic system 4300. Consequently, there is a need for the diagnostic system 4300 to check a type of a test kit. Information on a type of a test kit may be acquired through a user input. Alternatively, information on a type of a test kit may be acquired through an identifier or the like that is identifiable by the diagnostic system 4300, such as a near-field communication (NFC), tag and an identification code included in a test kit.

Therefore, the operations included in the diagnostic operation will be described in correlation with the above-described operations of the elements of the diagnostic system 4300.

4.2.1 Loading Operation

A diagnostic device 4310 according to an embodiment of the present disclosure may perform a loading operation in which a test kit is prepared so that a diagnostic operation may be performed.

Here, a loading region moving unit configured to perform an operation of loading a test kit may be present. The loading region moving unit may perform the loading operation by moving a loading region 4610 so that the loading region 4610 in which a test kit is placed may be provided to a user and/or the diagnostic device 4310. For example, the loading region moving unit may include a predetermined power generator and/or power transmitter and perform the loading operation by transmitting power generated by the power generator to the loading region 4610 through the power transmitter and moving the loading region 4610.

When the loading region moving unit is not present in the diagnostic device 4310, the moving unit 4311 may perform the loading operation in which a test kit is provided to a user and/or the diagnostic system 4300.

For example, the moving unit 4311 may perform the loading operation, in which a test kit placed in the loading region 4610 is provided to the diagnostic device 4310, through the moving operation.

When the above-described loading region moving unit configured to generate power and transmit power and/or the moving unit are not present, a user may perform an operation to manually place a test kit in the loading region 4610 of the diagnostic device 4310.

4.2.2 Smearing Operation

A diagnostic system 4300 according to an embodiment of the present disclosure may perform a smearing operation in which a specimen T, which is placed in a test kit, is smeared.

Such a smearing operation may be performed mainly by the moving operation of the moving unit 4311 in which a structure of a test kit is moved and/or a control operation of the controller 4315 controlling the moving operation of the moving unit 4311.

As described above, in the smearing operation, a specimen comes into contact with a smearing film of a patch plate so that the specimen is naturally spread in the width direction of the smearing film, and a smearing unit of the patch plate passes a specimen region again while sweeping the specimen region so that the specimen is smeared in the specimen region.

A relative movement operation of the moving unit 4311 that enables the smearing operation of the diagnostic system 4300 will be described below.

The diagnostic system 4300 according to an embodiment of the present disclosure may perform a diagnostic operation by performing a moving operation of the moving unit 4311 in which plates in a test kit are moved relative to each other.

Here, the movement of the plates relative to each other may signify that directions in which a specimen plate and/or a patch plate of a test kit move are not the same. For example, the relative movement may signify that, when a specimen plate moves in one direction, a patch plate is moved in another direction which is opposite the one direction. The relative movement may also signify that one of a specimen plate and a patch plate of a test kit is fixed and the other one is moved. For example, the relative movement may signify that a patch plate is fixed, and a specimen plate is moved in one direction so that the patch plate is disposed in another direction, which is opposite the one direction, relative to the specimen plate. Although another direction with respect to the one direction of the relative movement has been described as a direction opposite the one direction, the other direction is not limited to the opposite direction, and any direction which is not the same as the one direction may be the other direction. The relative movement may signify that, even when plates move in the same direction, the plates move at different speeds.

Typical examples of such relative movement may include sliding and/or rotating of plates relative to each other.

The above-described operation of the moving operation of the moving unit 4311 in which plates in a test kit are moved relative to each other will be referred to below as relative movement operation.

Figure 48:
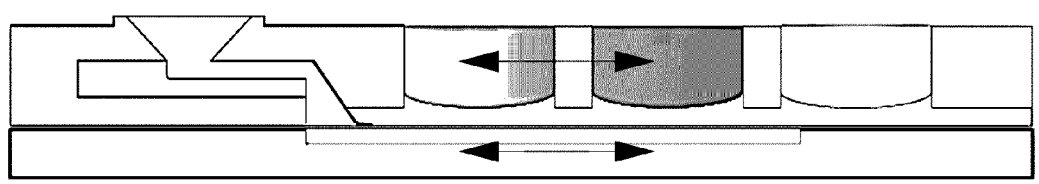
FIG. 48 is a conceptual diagram illustrating an example related to movement of a test kit in response to a relative movement operation of a moving unit according to an embodiment of the present disclosure.
Figure 49:
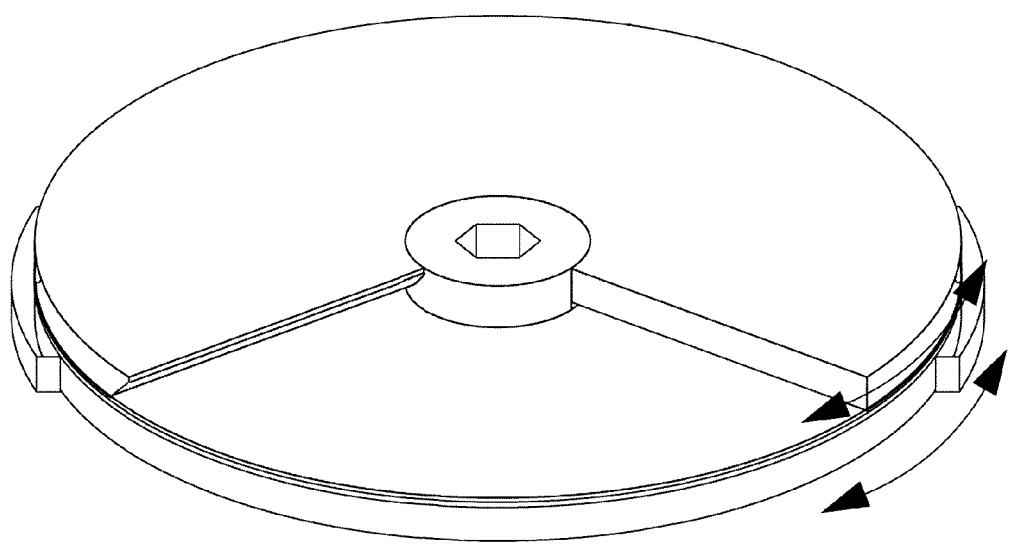
FIG. 49 is a conceptual diagram illustrating an example related to movement of a test kit in response to the relative movement operation of the moving unit according to an embodiment of the present disclosure.

FIG. 48 and/or FIG. 49 are conceptual diagrams illustrating an example related to movement of a test kit in response to a relative movement operation of the moving unit 4311 according to an embodiment of the present disclosure.

Referring to FIG. 48 and/or FIG. 49, a direction in which a specimen plate or a patch plate moves when the moving unit 4311 performs the relative movement operation according to an embodiment of the present disclosure can be seen. A specimen T placed on a specimen plate may be smeared by the relative movement of plates in a test kit relative to each other.

A patch plate and/or a specimen plate constituting a test kit may exhibit various forms of relative movement in accordance with various relative movement operations of the moving unit 4311.

For example, there may be a form of relative movement in accordance with a relative movement operation of the moving unit 4311 in which one element of a test kit is moved. Specifically, relative movement may be performed by the moving unit 4311 performing a moving operation in which a patch plate is moved in one direction while a specimen plate is fixed. Alternatively, relative movement may be performed by the moving unit 4311 moving a specimen plate in one direction while a patch plate is fixed.

In another example, there may be a form of relative movement in accordance with a relative movement operation of the moving unit 4311 in which a plurality of elements of a test kit are moved. That is, a relative movement operation may be performed by the moving unit 4311 performing a moving operation in which a plurality of elements of a test kit are moved. Here, in the form of relative movement, elements may simultaneously be moved, or each element may be sequentially moved. Specifically, a relative movement operation may be performed on a test kit by the moving unit 4311 performing a moving operation so that a specimen plate is moved in one direction and a patch plate is moved in another direction different from the one direction.

A relative movement operation may be performed by the moving unit 4311 performing a moving operation in which a specimen plate and/or a patch plate of a test kit are moved in the same direction while speeds at which the specimen plate and/or the patch plate are moved are different. However, in order to perform the smearing operation in which a specimen T is smeared, a relative movement operation has to be performed by the moving unit 4311 such that a movement speed of a patch plate in one direction is higher than a movement speed of a specimen plate in the one direction.

In accordance with the above-described relative movement operation, the diagnostic system 4300 may perform the smearing operation. As described above with respect to the smearing method of a test kit, the smearing operation may include an operation in which a specimen T is brought into contact with a smearing unit of a patch plate for the smearing operation to be performed (hereinafter referred to as a smearing first operation) and an operation in which the smearing unit is moved, relative to the specimen plate, toward a specimen region so that the specimen is smeared (hereinafter referred to as smearing second operation).

The smearing first operation and/or second operation performed by the diagnostic system 4300 will be described below.

4.2.2.1 Smearing First Operation

A diagnostic system 4300 according to an embodiment of the present disclosure may perform a smearing first operation in which, by a relative movement operation of the moving unit 4311, a smearing unit of a test kit is brought into contact with a specimen T.

The smearing first operation may be performed by the moving unit performing a relative movement operation in which the smearing unit of the test kit is moved in a direction in which the specimen is placed so that the smearing unit comes into contact with the specimen.

The moving unit may perform the smearing first operation by performing an operation in which the smearing unit is brought into contact with the specimen and then further performing an operation in which a structure of the test kit is moved. For example, after the smearing unit is in contact with the specimen, the moving unit may perform a moving operation in which the structure of the test kit is moved by a predetermined distance in a forward direction and/or a reverse direction of a direction in which the smearing unit has been moved in the direction in which the specimen is placed.

By the moving unit further performing a moving operation after the smearing unit is brought into contact with the specimen, the smearing unit of the test kit may come into contact with the specimen, and the spread of the specimen in a width direction of a smearing film may be effectively facilitated. This is because a predetermined process for facilitating the spread of the specimen after the smearing unit is brought into contact with the specimen is required since, while a specimen is able to be spread in a width direction of a smearing film just by the smearing film coming into contact with the specimen when the smearing film is specimen-friendly, it is difficult for a specimen to be spread in a width direction of a smearing film when the smearing film is non-specimen-friendly, as described above. Accordingly, for the predetermined process, after the smearing unit comes into contact with a specimen, a smearing film is moved before smearing of the specimen so that the specimen is spread in the width direction of the smearing film.

4.2.2.2 Smearing Second Operation

A diagnostic system 4300 according to an embodiment of the present disclosure may perform a smearing second operation in which, by a relative movement operation of the moving unit 4311, a smearing unit of a test kit is made to smear a specimen T in a specimen region. For example, after the smearing first operation, in order to smear a specimen T, the moving unit may perform the smearing second operation in which a structure of a test kit is relatively moved so that the smearing unit moves while sweeping the specimen region of a specimen plate in a reverse direction of the first operation.

Here, a controller 4315 according to an embodiment of the present disclosure may control a moving operation of the moving unit 4311 in performing the smearing second operation of the diagnostic system 4300.

For example, after an operation of smearing a specimen T, it is necessary to dry the smeared specimen T for staining the smeared specimen T. The controller 4315 may control a moving operation of the moving unit 4311 so that, during the drying time, the moving operation of the moving unit 4311 is not performed.

Also, as described above, either thick smearing or thin smearing may be performed in accordance with a type of a smearing film of a test kit and a smearing speed. To appropriately apply this to a diagnostic operation of the diagnostic system 4300, the controller 4315 may control a speed of a relative movement operation of the moving unit 4311.

Figure 50:
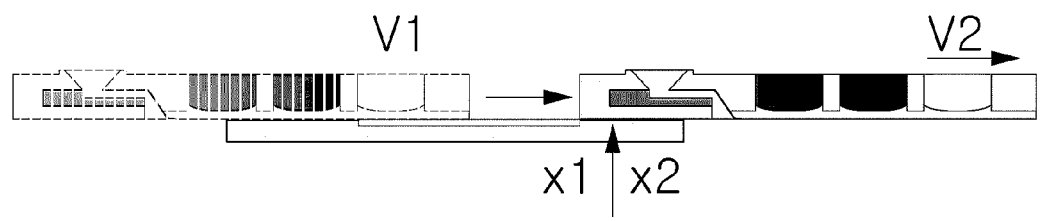
FIG. 50 is a conceptual diagram illustrating an example in which a controller (4315) controls a speed of a relative movement operation of a moving unit (4311) according to an embodiment of the present disclosure.

FIG. 50 is a conceptual diagram illustrating an example in which the controller 4315 controls a speed of a relative movement operation of the moving unit 4311 according to an embodiment of the present disclosure.

Referring to FIG. 50, the controller 4315 may control a speed of a relative movement speed of the moving unit 4311. For example, while the mover 4311 moves a structure of a test kit, the controller 4315 may assign different speeds at which plates are moved by the moving unit 4311 for each moving section. Specifically, for example, when the moving unit 4311 performs a relative movement operation in which a patch plate is moved in one direction while a specimen plate is fixed, the controller 4315 may control the moving unit 4311 to move the patch plate at a speed v1 when the patch plate is being moved in a section x1, and the controller may control the moving unit 4311 to move the patch plate at a speed v2 when the patch plate is being moved in a section x2.

Although the sections and/or speeds may be numerical values present in the diagnostic system 4300, the sections and/or speeds may also be numerical values set on the basis of data received through a user input or the like.

By the control operation of the controller 4315 in which a degree of smearing of the specimen T is made different for each section, the diagnostic system 4300 may perform different smearing operations for each section.

By making speeds at which the plates are moved by the moving unit 4311 to be different for each section, the controller 4315 may vary a degree of smearing of the specimen T. The diagnostic system 4300 may perform either of thick smearing or thin smearing for each section by adjusting the degree of smearing. When the smeared specimen T is stained and diagnosed afterwards, since different diagnostic means may be applied for each section, a user may perform diagnosis of a state of the specimen T in various ways.

4.2.3 Staining Operation

A diagnostic system 4300 according to an embodiment of the present disclosure may perform a staining operation in which a smeared specimen T in a test kit is stained. As described above, the staining operation may be performed by a contact unit performing a contact operation so that a contact-type patch comes into contact with a smeared specimen in a specimen region.

The staining operation according to an embodiment of the present disclosure may include an aligning operation in which plates in a test kit are aligned and/or a staining operation in which a specimen T placed in the test kit is stained.

The staining operation such as the above-described aligning operation and staining operation may be performed as the above-described contact operation of the contact unit 4313 in which a structure of a test kit is moved so that a contact-type patch contained in the test kit is brought into contact with a specimen T, the moving operation of the moving unit 4311, and/or the control operation of the controller 4315 are performed.

4.2.3.1 Adjusting Operation

A diagnostic system 4300 according to an embodiment of the present disclosure may perform an operation in which a position of a patch plate and/or a position of a specimen plate in a test kit are adjusted for the staining operation.

Referring to drawings in FIG. 35, the diagnostic system 4300 may perform an adjusting operation in which a plurality of storages 2220 contained in a patch plate of a test kit are sequentially placed at positions corresponding to the specimen region 2420. The positions corresponding to the specimen region may refer to positions right above a region of a specimen region of a specimen plate in which smearing is performed to be suitable for staining.

Such an adjusting operation may be performed as the moving operation of the moving unit and/or the control operation of the controller controlling the moving operation are performed. For example, the adjusting operation may be performed by the moving unit performing the operation in which a structure of a test kit is relatively moved and the controller controlling the relative movement operation so that storages may be placed at positions corresponding to a specimen region.

Through the adjusting operation, the diagnostic system 4300 may allow a contact-type patch to come into effective contact with a smeared specimen so that, in the staining operation which will be described below, staining of a smeared specimen is effectively performed.

4.2.3.2 Staining Operation

A diagnostic system 4300 according to an embodiment of the present disclosure may perform a staining operation in which a specimen T is stained.

As described above, the diagnostic system 4300 may perform the staining operation through the contact operation of the contact unit in which a contact-type patch contained in a patch plate of a test kit is brought into contact with a smeared specimen region.

Figure 51:
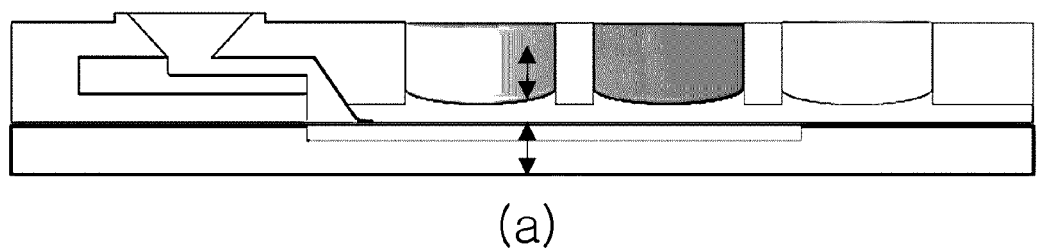
FIG. 51 is a conceptual diagram illustrating an example in which a structure of a test kit is moved by a contact operation of a contact unit according to an embodiment of the present disclosure.
Figure 51:
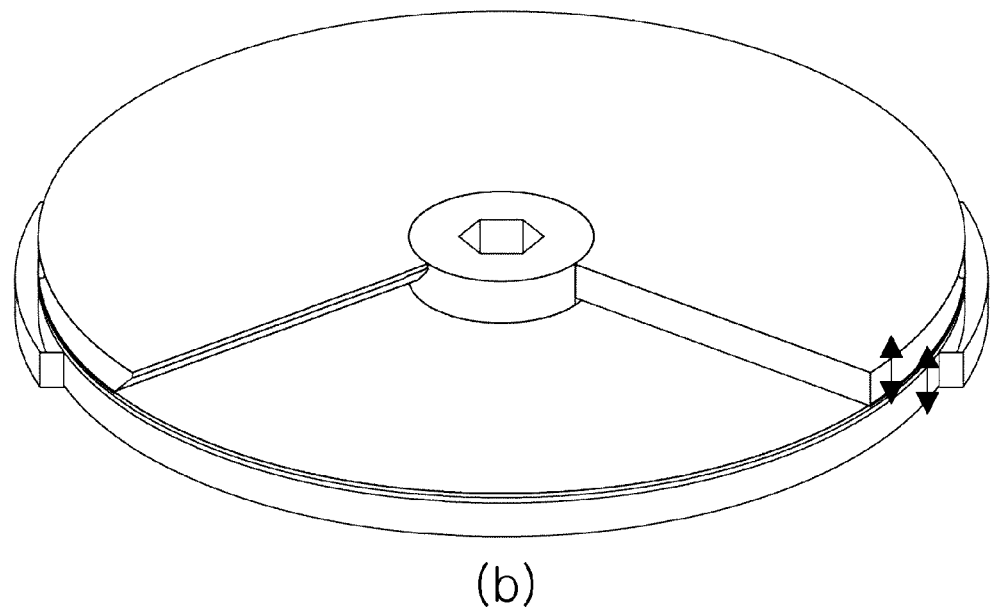

FIG. 51 and/or (a) and (b) of FIG. 52 are conceptual diagrams illustrating an example in which a structure of a test kit is moved by the contact operation of the contact unit 4313 according to an embodiment of the present disclosure.

Referring to FIG. 51, the contact unit 4313 may perform the staining operation through the contact operation in which plates of a test kit are moved. For example, by the contact unit 4313 performing the contact operation in which a patch plate and/or a specimen plate are vertically moved, the diagnostic system 4300 may perform the staining operation. That is, as the contact unit 4313 moves the patch plate and/or the specimen plate, a contact-type patch stored in the patch plate comes into contact with a smeared specimen T so that the staining operation may be performed.

As shown in (a) and (b) of FIG. 52, the contact unit 4313 may perform the staining operation by performing the contact operation in which a contact-type patch contained in a test kit is moved. For example, the contact unit 4313 may perform the contact operation for a contact-type patch stored in the patch plate to come into contact with a smeared specimen T on the specimen plate so that the specimen is stained.

FIG. 53 is a conceptual diagram illustrating an example in which a staining operation of the present disclosure is performed according to an embodiment of the present disclosure.

Referring to FIG. 53, the staining operation of the diagnostic system 4300 may be performed by the above-described contact operation of the contact unit 4313 and the moving operation of the moving unit 4311 being performed in association with each other. For example, the staining operation may be performed by the contact unit 4313 performing the contact operation while the moving unit 4311 performs the moving operation in which a plate in a test kit is moved in one direction.

Specifically, the staining operation may be performed by the moving unit 4311 performing an operation in which two plates are moved relative to each other so that a specimen region and storages are disposed opposite each other, and the contact unit 4313 sequentially performing, during the relative movement operation of them moving unit 4311, the contact operation at an outer surface of a patch plate so that a contact-type patch is moved to the specimen region.

For staining of a smeared specimen T in the staining operation of the diagnostic system 4300, at least a predetermined amount of staining time during which a contact-type patch is in contact with a smeared specimen T is required, and after the smeared specimen T is stained, time for drying the stained specimen T may be required.

That is, when, as described above, the moving unit 4311 continuously performs the moving operation while the contact unit 4313 performs the contact operation for a predetermined amount of time, the contact-type patch may be separated from the specimen T and the staining time may not be satisfied. When the moving unit 4311 and the contact unit 4313 continuously perform the operations, the drying time for the stained specimen T may not be satisfied. Accordingly, there is a need for the moving unit 4311 to not perform the moving operation while the contact unit 4313 performs the contact operation or the moving unit 4311 to perform the moving operation again.

For this, the controller 4315 may set time intervals between the contact operation of the contact unit 4313 and/or the moving operation of the moving unit 4311 in accordance with the staining time and the drying time.

FIG. 54 is a view illustrating an example in which a controller controls operations of elements of a diagnostic system in the staining operation according to an embodiment of the present disclosure.

Referring to FIG. 54, the controller 4315 may control a time interval between the contact operation of the contact unit 4313 and/or the moving operation of the moving unit 4311. Specifically, for example, referring to FIG. 54, the controller 4315 may control the contact operation of the contact unit 4313 to be performed for a predetermined time interval $\Delta t1$ and to not be performed for a predetermined time interval $\Delta t2$ in accordance with time intervals. In addition, for the moving unit 4311 to perform the moving operation after time for drying the specimen T after the specimen T is smeared on a specimen plate, the controller 4315 may set the moving operation of the moving unit 4311 to not be performed for the predetermined time interval $\Delta t1$ and to be performed for the predetermined time interval $\Delta t2$.

To (1) remove air bubbles from a contact surface, (2) allow a staining reagent of a contact-type patch to be transferred to a smeared specimen properly, or (3) complement the staining operation in other ways for an effective staining operation, the contact unit 4313 according to an embodiment of the present disclosure may perform an operation in which a contact-type patch, which is in contact with a specimen, is moved. For example, for an effective staining operation, the contact unit 4313 may perform a contact operation so that the contact-type patch in contact with the specimen is rolled while in contact with the specimen. The rolling may signify that the contact-type patch may vibrate in a longitudinal direction of a test kit and/or a direction perpendicular to the longitudinal direction while the contact-type patch is in contact with the specimen. Also, for example, for an effective staining operation, the contact unit 4313 may perform a contact operation so that a contact-type patch may move in a direction perpendicular to a wide surface of a test kit while the contact-type patch is in contact with the specimen.

Although operation time intervals related to the contact unit 4313 and the moving unit 4311 may be numerical values preset in the diagnostic system 4300, the operation time intervals may also be numerical values set on the basis of data received through a user input or the like.

4.2.4 Image Acquiring Operation

Hereinafter, an image acquiring operation of a diagnostic system 4300 that is performed to diagnose a state of a specimen T stained by the above-described smearing operation and/or staining operation will be described.

The diagnostic system 4300 according to an embodiment of the present disclosure may perform an operation of acquiring an image related to a stained specimen T in a test kit generated by the smearing operation and/or the staining operation.

Such an image acquiring operation may be performed by the image acquiring unit 4317 and/or the image acquiring unit 4317 performing operation in association with other elements.

When the image acquiring unit 4317 is present in an element of a system other than the diagnostic device 4310, an additional operation or the like may be performed for the image acquiring operation. For example, when the image acquiring operation is performed through the image acquiring unit 4317 implemented in another element of the diagnostic system, the diagnostic device 4310 may provide a test kit in the diagnostic device 4310 to another element of the diagnostic system so that the other element of the diagnostic system can perform the image acquiring operation capable of acquiring an image of a stained specimen T.

The image acquiring operation will be described below.

4.2.4.1 Movement of Test Kit

A diagnostic system 4300 according to an embodiment of the present disclosure may move a structure of a test kit and acquire an image when acquiring an image of a stained specimen placed in the test kit.

FIG. 55 is a view illustrating a process in which a structure of a test kit is moved so that an image is acquired according to an embodiment of the present disclosure.

Referring to FIG. 55, the moving unit 4311 may perform a moving operation so that a specimen region of a specimen plate is exposed to the image acquiring unit 4317. For example, the moving unit 4311 may perform a moving operation in which a patch plate and/or a specimen plate are moved relative to each other so that a specimen region of the specimen plate is exposed to the image acquiring unit 4317.

When an observation hole is provided in an upper portion of a patch plate, the moving unit 4311 may perform a moving operation so that a specimen region is disposed at a position at which the specimen region is exposed through the observation hole.

To facilitate generation of an image of a test kit, the diagnostic device 4310 may move the test kit to another space in the diagnostic device 4310 for the image to be generated.

FIG. 56 is a view illustrating a process in which a test kit is moved to another space so that an image is acquired according to an embodiment of the present disclosure.

Referring to FIG. 56, the moving unit 4311 may move a test kit to another space in the diagnostic system 4300. In this case, the moving unit 4311 may move a specimen plate and a patch plate together to another space or move only a specimen plate in a test kit to another space.

When a test kit is moved to another space in the diagnostic device 4310 for the image acquiring operation to be performed, the moving operation of the moving unit 4311 in which a structure of a test kit is moved for the above-described image acquisition may be performed in association with the image acquiring operation. For example, the moving unit may perform a moving operation so that a specimen region of a specimen plate is exposed after a test kit is moved to another space.

The image acquiring operation according to an embodiment of the present disclosure may be performed even in a state in which a test kit has not been moved. For example, by forming a structure so that a test kit may be placed between optical systems of the image acquiring unit 4317 or irradiating a test kit with a beam using a reflector such as a mirror, the image acquiring operation may be performed even without moving the test kit.

4.2.4.2 Combination of Image Frames

A diagnostic system 4300 according to an embodiment of the present disclosure may perform an image acquiring operation in which an image of a stained specimen T is acquired after the above-described operation in which a structure of a test kit and/or the test kit is moved.

FIG. 57 is a view illustrating an example of acquiring an image according to an embodiment of the present disclosure.

Referring to FIG. 57, a diagnostic system 4300 may acquire an image of a stained specimen T by acquiring a plurality of image frames of the stained specimen T and combining the acquired image frames. This is because an image with higher quality may be acquired when acquiring an image by combining a plurality of frames in comparison to when acquiring an image with a single frame in a low-illuminance situation or a limited space within the diagnostic system 4300.

Accordingly, for this, an operation in which a test kit and/or the image acquiring unit 4317 is moved may be performed while the diagnostic system 4300 performs an operation of acquiring an image.

For example, a movement member connected to the image acquiring unit 4317 may be separately provided for acquiring a plurality of frame images and moving the image acquiring unit 4317 including an image generator, an optical system, and/or a beam generator, or a moving operation of the moving unit 4311 in which a test kit is moved may be performed.

Captures 1 to 9 illustrated in FIG. 57 are merely examples of acquiring a plurality of frames, and a means in which the image acquiring unit 4317 captures an image of a stained specimen is not limited to the number of captures or directions of the captures illustrated in FIG. 57.

4.2.5 Diagnosis Result Generating Operation

A diagnostic system 4300 may perform an operation in which an image of a stained specimen is analyzed and a diagnosis result is generated.

A diagnosis result according to an embodiment of the present disclosure may be generated by analyzing an image of a stained specimen and diagnosing a state of the specimen through the above-described diagnosis result generator 4319.

A method of analyzing an image of a stained specimen during the diagnosis result generating operation according to an embodiment of the present disclosure may preferably be implemented by an image processing technique. For example, the diagnosis result generating operation may be a method of sensing data for each pixel of an image of a stained specimen and analyzing the sensed data to automatically diagnose the specimen in accordance with an algorithm preset in the diagnosis result generator 4319. Here, the algorithm may be an algorithm that compares the image of the stained specimen with a pre-contained diagnosis result image of the stained specimen. However, the method of analyzing an image is not limited to the above means as long as the method may be performed to analyze a diagnosis result.

The diagnosis result generating operation according to an embodiment of the present disclosure may also analyze an image of a stained specimen, diagnose a state of the specimen, and generate a diagnosis result without operation of a hardware or software element such as the diagnosis result generator 4319. For example, the diagnosis result generating operation may also be a method in which an image of a stained specimen is analyzed by a manager, a state of the specimen is diagnosed, and a diagnosis result is given as feedback in the diagnostic system.

Since a generated diagnosis result is eventually contained in the diagnostic system 4300, the diagnosis result generator 4319 may form big data. Accordingly, the diagnosis result generator 4319 according to an embodiment of the present disclosure may perform a diagnosis result generating operation on the basis of the big data. For example, by analyzing an image of a stained specimen and generating a diagnosis result through a predetermined algorithm in accordance with the big data generated by the diagnosis result generator 4319, a rate of misdiagnosis may be lowered in a diagnosis result, and the diagnosis result generated by the diagnosis result generator 4319 may also be verified in accordance with a predetermined algorithm according to the big data.

By the diagnosis result generator 4319 performing the diagnostic operation on the basis of the above-described big data, the diagnostic system 4300 may learn to generate an accurate diagnosis result by itself according to the present disclosure.

Each of the above-described diagnostic operations of the diagnostic system 4300 according to an embodiment of the present disclosure may be individually performed.

According to an embodiment of the present disclosure, "each of the diagnostic operations being able to be individually performed" may signify that each of the above-described diagnostic operations may be separately performed in each element of the diagnostic system 4300 or may signify that some of the above-described diagnostic operations may not be performed.

As a specific example, when, from among the diagnostic operations, a smearing operation and a staining operation are individually performed, the smearing operation may be performed by a first diagnostic device of the diagnostic system 4300 while the staining operation is performed by a second diagnostic device, only the smearing operation may be performed in the diagnostic device 4310 of the diagnostic system 4300 while the staining operation is not performed, or only the staining operation may be performed in the diagnostic device 4310 of the diagnostic system 4300 while the smearing operation is not performed.

Each of the diagnostic operations according to an embodiment of the present disclosure may be performed several times in the diagnostic system 4300.

According to an embodiment of the present disclosure, "each of the diagnostic operations being able to be performed several times" may signify that each of the diagnostic operations may be performed several times in one or more of one element and/or another element.

As a specific example, when, from among the diagnostic operations, the staining operation is performed several times, the staining operation may be performed several times in the diagnostic device 4310 of the diagnostic system 4300, the staining operation may be performed several times in a plurality of diagnostic devices 4310 in of the diagnostic system 4300, or the staining operation may be performed several times in the diagnostic device 4310 of the diagnostic system 4300 and/or the user terminal 4350.

The above-described elements of the diagnostic device 4310 according to an embodiment of the present disclosure may be implemented in a diagnostic system in accordance with the above-described types in which each of the diagnostic operations is performed. For example, when, from among the diagnostic operations, the smearing operation and the staining operation are individually performed, and the smearing operation is performed by the first diagnostic device of the diagnostic system 4300 while the staining operation is performed by the second diagnostic device, only a first moving unit may be implemented in the first diagnostic device, and a second moving unit and a contact unit may be implemented in the second diagnostic device.

4.3 Implementation of Diagnostic System of Present Disclosure

A user of a test kit according to an embodiment of the present disclosure may inject a specimen into a specimen region of a specimen plate through a specimen injection portion formed in a patch plate of the test kit. For diagnosis of a state of the specimen placed on the specimen plate of the test kit, the user may use the diagnostic system 4300, which is the present disclosure.

A method in which a user uses the diagnostic system 4300 implemented by the present disclosure will be described below.

FIG. 58 is a view illustrating a side view of a diagnostic device implemented by the present disclosure according to an embodiment of the present disclosure.

Referring to FIG. 58, a diagnostic device 4310 implemented by the present disclosure may include a moving unit 4311, a contact unit 4313, and an image acquiring unit 4317. In addition to the moving unit 4311, the contact unit 4313, and the image acquiring unit 4317, the diagnostic device 4310 may also include a loading region formed inside a body of the diagnostic device for a user of the diagnostic system to place a test kit.

FIG. 59 illustrates the loading region of the diagnostic device 4310 implemented by the present disclosure according to an embodiment of the present disclosure. Referring to FIG. 59, a loading region 4610 may be withdrawn from inside the body to the outside by a user for the user to place a test kit in the loading region from the outside of the diagnostic device 4310. Here, the loading region 4610 may be moved to the outside and/or the inside by the moving operation of the above-described loading region moving unit and/or the moving unit.

FIG. 60 is a view illustrating a moving unit implemented by the present disclosure according to an embodiment of the present disclosure.

Referring to FIG. 60, it may be seen that a moving unit 4311 according to an embodiment of the present disclosure has been implemented in a mechanical form. The moving unit 4311 may include a power transmission member 4703 (hereinafter referred to as a first power transmission member) configured to transmit power to a test kit, a power generator 4701 configured to generate power, and/or a power transmission member 4703 (hereinafter referred to as a second power transmission member) connected to the power generator 4701 and the first power transmission member to be engaged therewith so that power is transmitted to the power generator 4701 and the first power transmission member.

Here, the second power transmission member may be implemented in the form of a belt that connects a driving shaft of the power generator 4701 and a driven shaft of the first power transmission member as shown in FIG. 60 so that the second power transmission member transmits a rotational force of a motor. However, the shape of the second power transmission member is not limited to the present implementation. For example, the second power transmission member may also be implemented in the form of a bar connected to the driving shaft of the power generator 4701 or may be in the form in which the second power transmission member transmits power to the first power transmission member.

FIG. 61 is a view illustrating a moving operation that a moving unit implemented by the present disclosure performs according to an embodiment of the present disclosure.

Referring to FIG. 61, a moving operation performed by the moving unit 4311 implemented by the present disclosure will be described. A moving operation in which a structure of a test kit is moved may be performed by the moving unit 4311 transmitting rotational power generated by the power generator 4701 to the second power transmission member, the second power transmission member transmitting the received power to the first power transmission member, and the first power transmission member transmitting the power to the structure of the test kit in the form of a rack gear. In the implemented present disclosure, the first power transmission member may include a first mounting portion on which a patch plate of a test kit is mounted and a second mounting portion on which a specimen plate is mounted.

In an implementation of the present disclosure, by the above-described moving operation of the moving unit 4311, the diagnostic device 4310 may perform a smearing operation so that a specimen placed in a specimen region of a specimen plate of a test kit is smeared in the specimen region in a longitudinal direction of the specimen plate. Referring to FIG. 61, the mover 4311 of the diagnostic device 4310 may be an element that performs the smearing operation. The mover 4311 may perform the smearing operation by transmitting power generated by the power generator to a test kit through the second power transmission member connected to the first mounting portion on which a specimen plate is mounted and the second mounting portion on which a patch plate is mounted of the test kit and moving the specimen plate and/or the patch plate relative to each other. The smearing operation may include a smearing first operation and a smearing second operation. Through the above-described relative movement operation, the moving unit 4311 may perform the smearing first operation that allows a smearing unit of the patch plate to come into contact with a specimen in the specimen plate and the smearing second operation in which the smearing unit in contact with the specimen is moved to sweep the specimen region in the longitudinal direction of the plates. After the smearing second operation, an operation in which a fixing solution is applied on a smeared specimen or a fixing patch is brought into contact with the smeared specimen so that the smeared specimen is fixed may be performed.

FIG. 62 is a view illustrating a contact unit implemented by the present disclosure according to an embodiment of the present disclosure.

Referring to FIG. 62, it can be recognized that a contact unit 4313 implemented by the present disclosure is a contact unit 4313 having a mechanical form. The contact unit 4313 of the present disclosure may include a power transmission member 4903 configured to transmit power to a structure of a test kit and a power generator 4901 configured to generate power.

The power transmission member 4903 and the power generator 4901 may be connected to be engaged with each other to transmit the power generated by the power generator 4901 to the structure of the test kit instantly. For example, as shown in FIG. 62, the power transmission member 4903 and the power generator 4901 may be implemented to be engaged in the form of a rack gear so that the power transmission member 4903 may transmit mechanical type rotational power generated by the power generator 4901. In this way, a contact operation, in which power of the power generator 4901 is transmitted to a structure of a test kit upon contact therewith, and the structure of the test kit is moved in accordance of the received power so that a contact-type patch contained in the test kit comes into contact with the specimen T, may be performed.

In an implementation of the present disclosure, after the smearing operation is performed, the diagnostic device 4310 may perform the staining operation for staining a smeared specimen in a specimen region.

FIG. 63 is a view illustrating a contact operation that a contact unit of a diagnostic device performs according to an embodiment of the present disclosure.

Referring to FIGS. 61 and 63, the staining operation may be performed by the above-described operations of the moving unit 4311 and/or the contact unit 4313. For the staining operation, the moving unit 4311 may move a patch plate and/or a specimen plate relative to each other by transmitting power to the first mounting portion and/or the second mounting portion connected to the patch plate and/or the specimen plate so that a contact-type patch stored in the patch plate may be present on a specimen region. Here, for a plurality of contact-type patches to be sequentially brought into contact with a specimen on the specimen plate so that the specimen is stained, the moving unit 4311 may sequentially move an upper surface of a space, in which a contact-type patch is contained, to a position right below the power transmission member 4903 of the contact unit 4313, relative to the specimen plate. While the moving unit 4311 makes the patch plate and/or the specimen plate move relatively to each other, the contact unit 4313 may perform a contact operation in which, as shown in FIG. 63, the power transmission member 4903 is moved and the upper surface of the space in which the contact-type patch is contained is hit so that the contact-type patch may come into contact with the specimen on the specimen plate. While the staining operation of the diagnostic device 4310 is performed, the controller may control operations of the moving unit 4311 and the contact unit 4313 in consideration of time during which staining is performed by the contact-type patch coming into contact with the specimen and time during which drying is performed after staining.

In an implementation of the present disclosure, after the specimen is stained, the diagnostic device 4310 may perform an operation in which an image of the stained specimen is generated. To facilitate generation of an image of the stained specimen, a test kit of the stained specimen may be moved to another space within the diagnostic device 4310. The operation in which the test kit is moved may be performed by the moving unit 4311 or a predetermined power transmitter constituting the image acquiring unit 4317. After the test kit is moved, light output from a light source may be focused on the test kit through an optical system, and the light may be received by an image sensor so that an enlarged image of a stained specimen may be generated. Here, while the moving unit 4311 and/or the predetermined power transmitter constituting the image acquiring unit 4317 moves a test kit in which a stained specimen is placed as shown in FIG. 57, the image acquiring unit 4317 implemented in the present disclosure may capture a plurality of images and generate an enlarged image of the stained specimen. The diagnostic device 4310 may adjust magnification of the stained specimen by electronically controlling a lens thickness of the optical system of the image acquiring unit 4317.

The enlarged image of the stained specimen may be analyzed by the diagnosis result generator 4317 of the server 4330, and a diagnosis result of the specimen may be generated. Such a diagnosis result of the specimen may be transmitted to the diagnostic device 4310 through a network such as a predetermined communication network and output through an output module of the diagnostic device 4310 so that the diagnosis result is provided to a user.

4.4 Diagnostic Method

A series of process related to the above-described diagnostic system 4300 and/or a diagnostic operation performed by the diagnostic system 4300 will be described below.

FIG. 64 is a flowchart illustrating a diagnostic method according to an embodiment of the present disclosure.

Referring to FIG. 64, a diagnostic method may include a loading operation in which a test kit is provided to a diagnostic device 4310, a smearing operation in which a specimen T in a test kit is smeared, a staining operation in which the specimen T is stained, an image acquiring operation in which an image of the stained specimen T is acquired, and a diagnosis result generating operation in which a state of the specimen T is diagnosed from the image. Although all of Steps S6310 to S6390 may be performed, it is not always necessary to perform all of Steps S6310 to S6390, and only at least one of the Steps S6310 to S6390 may be performed.

Each step will be described in detail below.

In a loading operation step S6310 in which a test kit is provided to the diagnostic device 4310, the control module 5109 may grasp a state of the test kit in the loading region 4610 and provide the grasped state as feedback to a user. For example, whether a test kit is present in the loading region 4610 may be detected, and a detected result may be provided as feedback to the user. When the test kit is not placed at a proper position, the fact that the test kit is not placed at a proper position may be provided as feedback to the user.

In a smearing operation step S6330 in which a specimen T in the test kit is smeared, the specimen T placed on a specimen plate of the test kit may be smeared on a specimen region of the specimen plate in accordance with operation of a moving unit 4311 and/or a controller 4315 configured to control the same of the diagnostic device 4310.

An operation of the diagnostic system 4300 in which the stained specimen is fixed may be performed after the smearing operation step S6330 according to an embodiment of the present disclosure or before a staining operation step S6350, which will be described below. In the fixing operation, preferably, fixation using chemical means may be performed. For example, as described above, the fixing operation may be an operation in which a fixing patch, which includes a fixing agent configured to generate a chemical change so that a specimen is fixed, is brought into contact with the smeared specimen, or an operation in which a fixing solution including a fixing agent is applied to the smeared specimen.

Although the above-described fixing operation may be performed by moving operations of a moving unit and/or a contact unit of the diagnostic system, the fixing operation may also be performed by a user of the diagnostic system. The fixing operation between the smearing operation step S6330 and the staining operation step S6350 may also be omitted.

In the staining operation step S6350 in which the specimen T is stained, staining of the smeared specimen T on the specimen plate of the test kit may be performed in accordance with operations of the moving unit 4311, the contact unit 4313, and/or the controller 4315 configured to control the same of the diagnostic device 4310.

In an image acquiring operation step S6370 in which an image of the stained specimen T is acquired, a process of acquiring a plurality of frame images of the stained specimen T may be a process in which, in addition to a scanning means, a plurality of frame images of the stained specimen T are acquired, and the acquired plurality of frame images may also be synthesized to acquire an image of the stained specimen T.

In a diagnosis result generating operation step S6390 in which a state of the specimen T is diagnosed, the diagnosis result generator 4319 of the diagnostic system 4300 may analyze the image of the stained specimen T and generate a diagnosis result related to a state of the specimen T.

In the diagnosis result generating operation step according to an embodiment of the present disclosure, the smearing operation and/or the staining operation of the diagnostic system 4300 may be individually performed or may not be performed. As an example thereof, the diagnostic system 4300 may include only the moving unit 4311 and thus perform only the smearing operation, include the moving unit 4311 and the contact unit 4313 and thus perform only the staining operation, include only the contact unit while relative movement is performed by a user and thus perform only the staining operation, or include a plurality of moving units 4311 and/or contact unit 4313 and thus individually perform the smearing operation and the staining operation.

The generated diagnosis result of the specimen T may be contained in the diagnosis result generator 4319 or transmitted to another external device and contained therein. The diagnosis result may be given as feedback by means of being output so that a user may view the diagnosis result through the diagnostic device 4310, the server 4330, and/or the user terminal 4350 of the diagnostic system 4300.

In a writing method and/or a browsing method according to the present disclosure described above, steps that constitute each embodiment are not essential, and accordingly, each embodiment may selectively include the above-described steps. It is not always necessary for the steps constituting each embodiment to be performed in accordance with the above-described order, and a step described later may also be performed prior to a step described earlier. Also, any one step may be repeatedly performed while each step is performed.

Although configurations and features of the present disclosure have been described above on the basis of embodiments according to the present disclosure, the present disclosure is not limited thereto, and it should be apparent to those of ordinary skill in the art to which the present disclosure pertains that various changes or modifications may be made within the spirit and scope of the present disclosure. Therefore, it should be noted that such changes or modifications belong to the scope of the appended claims.

The invention claimed is:

1. A diagnostic device using a test kit comprising a specimen plate having a specimen region in which a specimen is smeared and a patch plate configured to store a contact-type patch, which comes into contact with the specimen to stain the specimen, the diagnostic device comprising:
a body having a loading region in which the test kit is placed;
a moving unit configured to move the patch plate and the specimen plate of the test kit relative to each other so that the specimen placed in the test kit is smeared on the specimen region; and
a contact unit configured to move a structure of the test kit such that the contact-type patch comes into contact with the smeared specimen so that the smeared specimen is stained.

2. The diagnostic device of claim 1, further comprising an image acquisition module configured to acquire an image of the stained specimen.

3. The diagnostic device of claim 2, further comprising a diagnostic module configured to diagnose a state of the specimen on the basis of the acquired image of the stained specimen.

4. The diagnostic device of claim 1, wherein:
the relative movement of the diagnostic device has a form such that the patch plate is moved in one direction and the specimen plate is fixed or moved; and
when the specimen plate is moved in the one direction, a movement speed of the patch plate is higher than a movement speed of the specimen plate.

5. The diagnostic device of claim 1, wherein:
the loading region is formed inside the body; and
the diagnostic device further comprises a loading region moving unit configured to move the loading region,
wherein the loading region moving unit moves the loading region to allow a user to place the test kit in the loading region.

6. The diagnostic device of claim 1, wherein the moving unit includes a power generator configured to generate power and a power transmission member configured to transmit the power to the structure of the test kit.

7. The diagnostic device of claim 6, wherein:
the power generator and the power transmission member are engaged with each other; and
the moving unit transmits the power to the specimen plate and the patch plate through the power transmission member.

8. The diagnostic device of claim 1, wherein the contact unit comprises a power generator configured to generate power and a power transmission member configured to transmit the power to the structure of the test kit.

9. The diagnostic device of claim 8, wherein:
the power generator and the power transmission member are engaged with each other; and the contact unit transmits the power to the contact-type patch stored in the patch plate through the power transmission member.

10. The diagnostic device of claim 1, wherein the moving unit:
does not allow the relative movement of the test kit when the contact-type patch is in contact with the specimen region; and
allows the relative movement of the test kit when the contact-type patch is not in contact with the specimen region.

11. The diagnostic device of claim 2, wherein the image of the stained specimen is generated after one or more of the test kit having the stained specimen placed therein and the structure of the test kit are moved.

12. A diagnostic device using a test kit including a specimen plate having a specimen region in which a specimen is smeared and a patch plate configured to store a contact-type staining patch, which comes into contact with the specimen to stain the specimen, the diagnostic device comprising:
a moving unit configured to move a structure of the test kit,
wherein the moving unit transmits power to one or more of the specimen plate and the patch plate through a power transmission member, and moves the specimen plate and the patch plate relative to each other such that a smearing unit of the patch plate moves in one direction along a longitudinal direction of the test kit so that the specimen is smeared in the specimen region.

13. The diagnostic device of claim 12, wherein:
the patch plate includes a smearing unit; and
the smearing unit comes into contact with the specimen and spreads the specimen.

14. The diagnostic device of claim 13, wherein:
to bring the smearing unit in contact with the specimen, the moving unit moves the specimen plate and the patch plate relative to each other; and
when the smearing unit is in contact with the specimen, the moving unit further moves the specimen plate and the patch plate relative to each other so that the smearing unit is moved in the one direction or another direction different from the one direction.

15. The diagnostic device of claim 14, wherein:
the moving unit controls a relative movement speed of the specimen plate and the patch plate; and
the control of the relative movement speed includes controlling speeds of one or more of the specimen plate and the patch plate.

16. A diagnostic device using a test kit including a specimen plate having a specimen region in which a specimen is smeared and a patch plate configured to store a contact-type patch, which comes into contact with the specimen to stain the specimen, the diagnostic device comprising:
a moving unit configured to move the specimen plate and the patch plate relative to each other so that the specimen is smeared in the specimen region; and
a contact unit configured to stain the smeared specimen, wherein:
the contact unit transmits power to a structure of the test kit through a power transmission member and moves one or more of the specimen plate and the patch plate for the contact-type patch to come into contact with the specimen region in which the specimen is smeared.

17. The diagnostic device of claim 16, wherein the moving unit moves the specimen plate and the patch plate relative to each other so that the patch plate and the specimen plate are aligned and moves the patch plate and the specimen plate relative to each other so that the contact-type patch of the patch plate is placed in the specimen region of the specimen plate.

18. The diagnostic device of claim 17, wherein, when there are a plurality of contact-type patches, the contact unit transmits power to the structure of the test kit such that the plurality of contact-type patches come into contact with the specimen region sequentially.

19. The diagnostic device of claim 18, wherein the contact unit transmits power to the plurality of contact-type patches stored in the patch plate in the structure of the test kit.

20. The diagnostic device of claim 17, wherein the contact unit transmits power to the structure of the test kit for a predetermined amount of time so that the contact-type patch comes into contact with the specimen region for the predetermined amount of time.

* * * * *